US006197948B1

(12) United States Patent
Zhu et al.

(10) Patent No.: US 6,197,948 B1
(45) Date of Patent: Mar. 6, 2001

(54) GRAPEVINE LEAFROLL VIRUS (TYPE 2) PROTEINS AND THEIR USES

(75) Inventors: Hai-Ying Zhu; Kai-Shu Ling; Dennis Gonsalves, all of Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/080,983

(22) Filed: May 19, 1998

Related U.S. Application Data

(60) Provisional application No. 60/047,194, filed on May 20, 1997.

(51) Int. Cl.[7] ........................... C12N 15/33; C12N 15/40; C12N 15/52
(52) U.S. Cl. ..................................... 536/23.72; 435/320.1
(58) Field of Search ............................... 435/69.1, 320.1, 435/410, 414, 419, 468, 469, 470; 536/23.72; 800/278, 279, 280, 288, 293, 294, 295, 301, 317.3

(56) References Cited

U.S. PATENT DOCUMENTS

| | | | |
|---|---|---|---|
| 4,358,535 | 11/1982 | Falkow et al. | 435/5 |
| 4,480,040 | 10/1984 | Owens et al. | 435/6 |
| 5,043,272 | 8/1991 | Hartley | 435/91.1 |
| 5,104,792 | 4/1992 | Silver et al. | 435/6 |
| 5,106,727 | 4/1992 | Hartley et al. | 435/6 |
| 5,196,305 | 3/1993 | Findlay et al. | 435/6 |
| 5,288,611 | 2/1994 | Kohne | 435/6 |
| 5,322,770 | 6/1994 | Gelfand | 435/6 |
| 5,328,825 | 7/1994 | Warren, III et al. | 435/6 |

FOREIGN PATENT DOCUMENTS

WO 97/22700   6/1997   (WO) ............................. C12N/15/40

OTHER PUBLICATIONS

Boston et al, Plant Mol. Biol., vol. 32, pp. 191–222, 1996.*
Stam et al, Ann. Bot., vol. 79, pp. 3–12, 1997.*
Nejidat et al, Physiol. Plant., vol. 80, pp. 662–668, 1990.*
Ling, "Coat Protein Gene Identification, Genome Organization and PCR Detection of Grapevine Leafroll Associated Closterovirus–3 and Study Towards Transgenic Grapevines (Vitis)," *The American Chemical Society*, 125:138016 (abstract).
Gugerli et al., "Identification Immuno–Chimique du 6[e] Virus Associé á la Maladie de L'Enroulement de la Vigne et Amélioration des Techniques de Diagnostic Pour la Sélection Sanitaire en Viticulture," *Revue Suisse Vitic. Arboric. Hortic.*, 29:137–141 (1997).
Gugerli et al., "L'Enroulement de la Vigne: Mise en Évidence de Particules Virales et Dévelopement d'une Méthode Immuno–Enzymatique Pour le Diagnostic Rapide," *Revue Suisse Vitic. Arboric. Hortic.*, 16:299–304 (1984).
Boscia et al., "Nomenclature of Grapevine Leafroll–Associated Putative Closteroviruses," *Vitis*, 34:171–175 (1995).

Goszczynski et al., "Production and Use of Antisera Specific to Grapevine Leafroll–Associated Viruses Following Electrophoretic Separation of Their Proteins and Transfer to Nitrocellulose," *African Plant Protection*, 1:1–8 (1995).
Goszczynski et al., "Grapevine Leafroll–Associated Virus 2 (GLRaV–2)–Mechanical Transmission, Purification, Production and Properties of Antisera, Detection by ELISA," *S. Afr. J. Enol. Vitic.*, 17:15–26 (1996).
Goszczynski et al., "Detection of Two Strains of Grapevine Leafroll–Associated Virus 2," *Vitis*, 35:133–135 (1996).
Zhu et al., "Nucleotide Sequence and Genome Organization of Grapevine Leafroll–Associated Virus–2 Are Similar to Beet Yellows Virus, The Closterovirus Type Member," *Journal of General Virology*, 79:1289–1298 (1998).
Zimmermann et al., "Characterization and Serological Detection of Four Closterovirus–like Particles Associated with Leafroll Disease on Grapevine," *J. Phytopathology*, 130:205–218 (1990).
Ghanem et al., "Physico–Chemical and Molecular Chraacterizatioin of Grapevine Leafroll–Associated Virus 2," 12th Meeting of the International Council for the Study of Viruses and Virus–Like Diseases of the Grapevine, Sep.–Oct., 1997.
Gugerli et al., "Grapevine Leafroll Associated Virus II Analyzed by Monoclonal Antibodies," 11th Meeting of the International Council for the Study of Viruses and Virus–Like Diseases of the Grapevine.
Zhu et al., "Production and Application of An Antibody to the Grapevine Leafroll Associated Closterovirus 2 Coat Protein Expressed in *Escherichia Coli*," 12th Meeting of the International Council for the Study of Viruses and Virus–Like Diseases of the Grapevine, Sep.–Oct., 1997 Abstract.
Zhu et al., "Nucleotide Sequence and Genome Organization of Grapevine Leafroll Associated Closterovirus 2," 12th Meeting of the International Council for the Study of Viruses and Virus–Like Diseases of the Grapevine, Sep.–Oct., 1997 Abstract.
Cabndresse et al., "Virus Taxonomy–Classification and Nomenclature. Part II. The Viruses–Closterovirus," *Archives of Virology*, S10:461–464 (1995).

(List continued on next page.)

*Primary Examiner*—David T. Fox
*Assistant Examiner*—Ashwin D. Mehta
(74) *Attorney, Agent, or Firm*—Clark & Elbing LLP

(57) ABSTRACT

The present invention relates to isolated proteins or polypeptides of grapevine leafroll virus (type 2). The encoding DNA molecules either alone in isolated form or in an expression system, a host cell, or a transgenic grape plant are also disclosed. Other aspects of the present invention relates to a method of imparting grapevine leafroll resistance to grape and tobacco plants by transforming them with the DNA molecules of the present invention, a method of imparting beet yellows virus resistance to a beet plant, a method of imparting tristeza virus resistance to a citrus plant, and a method of detecting the presence of a grapevine leafroll virus, such as GRLaV-2, in a sample.

7 Claims, 15 Drawing Sheets

OTHER PUBLICATIONS

Dolja et al., "Molecular Biology and Evolution of Closteroviruses: Sophisticated Build–Up of Large RNA Genomes," *Annu. Rev. Phytopathol.*, 32:261–285 (1994).

Ling et al., "Identification of Coat Protein Gene and Partial Genome Organization of Grapevine Leafroll–Associated Closterovirus Type III," *Phytopathology*, 84:1372 (1994) Abstract.

Habili et al., "Natural Spread and Molecular Analysis of Grapevine Leafroll–Associated Virus 3 in Australia," *Phytopatholoy*, 85:1418–1422 (1995).

Ling et al., "Partial Genome Organization of Grapevine Leafroll–Associated Closterovirus 3," *Phytopathology*, 85:1152 (1995) Abstract.

Karasev et al., "Screening of the Closterovirus Genome by Degenerate Primer–Mediated Polymerase Chain Reaction," *Journal of General Virology*, 75:1415–1422 (1994).

Minafra et al., "Detection of Grapevine Closterovirus A in Infected Grapevine Tissue by Reverse Transcription–Polymerase Chain Reaction," *Vitis*, 31:221–227 (1992).

Minafra et al., "Sensitive Detection of Grapevine Virus A, B, or Leafroll–Associated III From Viruliferous Mealybugs and Infected Tissue by cDNA Amplification," *Journal of Virological Methods*, 47:175–188 (1994).

Saldarelli et al., "Detection of Grapevine Leafroll–Associated Closterovirus III By Molecular Hybridization," *Plant Pathology*, 43:91–96 (1994).

Genbank Sequence for Grapevine Leafroll Associated Virus RNA6 Gene.

Genbank Sequence for Grapevine Leafroll Associated Virus Type III p20 Protein.

Wetzel et al., "A Highly Sensitive Immunocapture Polymerase Chain Reaction Method for Plum Pox Potyvirus Detection," *Journal of Virological Methods*, 39:27–37 (1992).

Krastanova et al., "Transformation of Grapevine Rootstocks With the Coat Protein Gene of Grapevine Fanleaf Nepovirus," *Plant Cell Reports*, 14:550–554 (1995).

Schell et al., "Transformation of 'Nova' Tangelo With the Coat Protein Gene of Citrus Tristeza Closterovirus," *Phytopathology*, 84:1076 (1994) Abstract.

Beachy et al., "Coat Protein–Mediated Resistance Against Virus Infection," *Annu. Rev. Phytopathol.*, 28:451–474 (1990).

Le Gall et al., "Agrobacterium–Mediated Genetic Transformation of Grapevine Somatic Embryos and Regeneration of Transgenic Plants Expressing the Coat Protein of Grapevine Chrome Mosaic Nepovirus (GCMV)," *Plant Science*, 102:161–170 (1994).

* cited by examiner

```
GLRaV2-PRO₁   SRVIYPDGRCYLAHMRYLCAFYCRPFRESDYALGMWPTVARLRACVEKNFGVEACGIALRGYYTSRNVYHCDYDSAYVKYFRNLSGRIG/G
GLRaV2-PRO₂   TRIRYPNGFCYLAHCRYACAFLLRGFDPKRFDIGAFPTAAKLRNRMVSELGERSLGLNLYGAYTSRGVPHCDYDAKFIKDLRLMSAVIA/G
BYV-P-PRO     LQYRPGEGLCYLAHAALCCALQKRTFREEDFFVGMYPTKFVFAKRLTEKLGPSALKHPVRGRQVSRSLFHCDVASAFSSPPFYSLPRFIG/G
Consensus     .......G.CYLAH....CA...R.P.......G..PT............G.........G...SR...HCD...............I./G
```

FIG. 3A

```
                          MT I                          MT Ia                  MT II
GLRaV2-MTR    MSEATQNSLTRFYPQFELKFSHSSHSDHPAAAASRLLENETLVRLCGNSVSDIGGCPLFHLHSKTQRRVHVCRPVLDGKDAQRRVVRDLQ
BYV-MTR       MGEAVQSGLTRAYPQFNLSPTHSVYSDHPAAAGSRLLENETLASMAKSSFSDIGGCPLFHIK-RGSTDYHVCRPIYDMKDAQRRVSRELQ
                                  MT IIa        MT III
GLRaV2-MTR    YSNVRLG-DDDKILEGPRNIDICHYPLGACDHESSAMMMVQVYDASLYEICGAMIKKKSRITYLTMVTPGEPLDGRECVYMESLDCEIEV
BYV-MTR       ARGLVENLSREQLVEAQARVSVCPHTLGNCNVKSDVLIMVQVYDASLNEIASAMVLKESKVAYLTMVTPGELLDEREAFAIDALGCDVVV
                     MT IV
GLRaV2-MTR    DVHADVVMYKFGSSCYSHKRLSIIKDIMTTPYLTLGGFLFSVEMYEVRMGVNYFKITKSEVSPSISCTKLLRYRRANSDVVKVKLPRFD
BYV-MTR       DTRRDMVQYKFGSSCYCHKLSNIKSIMLTPAFTFSGNLFSVEMYENRMGVNYYKITRSAYSPEIRGVKTLRYRRACTEVVQVKLPRFD
```

FIG. 3B

```
                 HEL I                      HEL Ia
GLRaV2-Hel    FVFTNSSVDILLYEAPPGGGKTTTLIDSFLKVFKKGEVSTMILTANKSSQVEILKKVEKEVSNIECQKRKDKRSPKKSIYTIDAYLMHHR
BYV-Hel       FTFTNLSANVLLYEAPPGGGKTTTLIKVFCETFSK--VNSLILTANKSSREEILAKVNRIVLD-EGDTPLQTRDR---ILTIDSYLMNNR
                 HEL II                   HEL III                       HEL IV
GLRaV2-Hel    GCDADVLFIDECFMVHAGSVLACIEFTRCHKVMIFGDSRQIHYIERNELDKCLYGDLDRFVDLQCRVYGNISYRCPWDVCAWLSTVYGNL
BYV-Hel       GLTCKVLYLDECFMVHAGAAVACIEFTKCDSAILFGDSRQIRYGRCSELDTAVLSDLNRFVDDESRVYGEVSYRCPWDVCAWLSTFYPKT
                                                                                    HEL V
GLRaV2-Hel    IATVKGESEGKSSMRINEINSVDDLVPDVGSTFLCMLQSEKLEISKHF---IRKGLTKLNVLTVHEAQGETYARVNLVRLKFQEDEPFKS
BYV-Hel       VATTNLVSAGQSSMQVREIESVDDVEYSSEFVYLTMLQSEKKDLLKSFGKRSRSSVEKPTVLTVHEAQGETYRKVNLVRTKFQEDDPFRS
                 HEL VI
GLRaV2-Hel    IRHITVALSRHTDSLTYNVLAARRGDATCDAIQKAAELVNKFRVFPTSFGGS
BYV-Hel       ENHITVALSRHVESLTYSVLSSKRDDAIAQAIVKAKQLVDAYRVYPTSFGGS
```

FIG. 3C

```
                 RdRP I                    RdRP II                     RdRP III
GLRaV2-RdRP   ICRFKLMVKRDAKVKLDSSCLTKHSAAQNIMFHRKSINAIFSPIFNEVKNRIMCCLKPNIKFPTEMTNRDFASVVSNMLGDDDVYHIGEV
BYV-RdRP      ITTFKLMVKRDAKVKLDSSCLVKHPPAQNIMFHRKAVNAIFSPCFDEFKNRVITCTNSNIVFPTEMTNSTLASIAKEMLGSEHVYNVGEI
                 RdRP IV                                   RdRP V
GLRaV2-RdRP   DFSKYDKSQDAFVKAFEEVMYKELGVDEELLAIWMCGERLSIANTLDGQLSFTIENQRKSGASNTWIGNSLVTLGILSLYYDVRNFEALY
BYV-RdRP      DFSKFDKSQDAFIKSFERTLYSAFGPDEDLLDVWMQGEYTSNATTLDGQLSFSVDNQRKSGASNTWIGNSIETLGILSMFYYTNRFKALF
                 RdRP VI                  RdRP VII           RdRP VIII
GLRaV2-RdRP   ISGDDSLIFSRSEISNYADDICTDMGFETKFMSPSVPYFCSKFVVMCGHKTFFVPDPYKLFVKLGAVKEDVSMDFLFETFTSFKDLTSDF
BYV-RdRP      VSGDDSLIFSESPIRNSADAMCTELGFETKFLTPSVPYFCSKFFVMTGHDVFFVPDPYKLLVKLGASKDEVDDEFLFEVFTSFRDLTKDL

GLRaV2-RdRP   NDERLIQKLAELVALKYEVQTGNTTLAL
BYV-RdRP      VDERVIELLTHLVHSKYGYESGDTYAAL
```

FIG. 3D

```
GLRaV-2     CAUGAUAAGCAGCGUGUUUAGCGUAGUUCGGUCGCAGGCGAUUCCGCGUAGA
BYV         CACGACCCGCAGCGGGUUUAGCUCGAUUCGCUCGCAGGCGAUUCCUAAGAGG
BYSV        CACGAUAACAGCGCGUUUAGCGUAGUUAGGUCGCAGGCCAUCCCUAAAAGG
CTV         CACGAACCGGCUCGCGUUCGGCGUAGUAAGGUCACAAGCAAUUCCUCCAAGA
Consensus   CA.GA.......CG.GUU..GC....U....UC.CA.GC.AU.CC....AG.
```

FIG. 4A

```
GLRaV-2     H D K Q R V S V V R S Q A I P R R
BYV         H D P Q R V S S I R S Q A I P K R
BYSV        H D E Q R V S V V R S Q A I P K R
CTV         H E P A R V G V V R S Q A I P P R
Consensus   H . . . R V . . . R S Q A I P . R
```

FIG. 4B

```
GLRaV2-HSP70   MVVFGLDFGTTFSTVCVYKDGRVFSFKQNNSAYIPTYLYFSDGNMMFRGYEAESLMSNLKVKGSFYRDLKRWGCDSSNLDAVLDRLKP
BYV-HSP70      MVVFGLDFGTTFSSVCAYVGEELYLFKQRDSAYIPTYVFHSDIQEVAFGDAEVLSNDLSVRGGFYRDLKRWIGCDENYRDVLEKLKP
                                                                                          B
GLRaV2-HSP70   HYSVRLJVKIGSGLNEIVSIGNFGGTVKSPAHLPGLIAFIKAVISCAEGAFACICTGVICSVPANYDSVQRNFTDQCVSLSGYQCVYMIN
BYV-HSP70      HYKTELIKVAQSSKSTVKLDCYSGIVPQNATLPGLIATFVKALISTASEAFKQCQIGVICSVPANYNCLQRSFTESCVNLSGYPCVYMVN
                                    C                                D
GLRaV2-HSP70   EPSAAALSACNSIGKKSANLAVYDFCGGIFDVSIISYRNNIFVVRASGCDINLGGRDVDRAFLIHLFSLJSLEPLJTLDISNLRESLSKT
BYV-HSP70      EPSAAALSACSRIKGATSPVILVYDFCGGIFDVSVISAINNIFVVRASGDMLGGRDIDKAFVEHLYNKAQLPVNYKDIISFLRESLSRK
                                                                             E
GLRaV2-HSP70   DAEIVYTLRGVDGRKEDVRMKNILIASMLPYVNRTLKITLESTLKSYAKSMESARVKCDLVLIGGSSYLPGLADVLIAKEQSVDRITRVS
BYV-HSP70      VSFLNFPVVSEQGVRVDVLNVNSELAEVAAPFVERTIKIVKEVYEKYCSSVRLEPNVKAKLLMVGGSSYLPGLLSRLSSIPFVDECIVLP
                    F                                                        G
GLRaV2-HSP70   DERAAVAVGCALYSSCLSGSGLLJIDCAAHTVAIADRSCHQIICAPAGAPIPFSGSMPLYLARVMKNSQREVAVFEGEXYVKCPANRKIC
BYV-HSP70      DARAAVAGGCALYSACLRNDSPMLJVDCAAHNLSISSKYCESIVCPAGSPIPFTGVRFVNMIGSNASAVYSAALFEEDFVKCRINKRIF
                                                       G
GLRaV2-HSP70   GANIRFFDIGVIGDSYAPVIFYMDFSILSSVGAVSFVVRGPEGKQVSLIGTPAYNFSSVALGSRSVRELHISLNNKVFLGLILHRKADRRI
BYV-HSP70      FGDVVLQNMGVIGSAIRIVPLJTLEINVSSVGTISFSLWGPTGVKKLLIGQNAVAYDFSSYQLGERVVADLHKHNSDKVKLIHALITYQPFQRK
                                    H
GLRaV2-HSP70   LFTKDEAIRYADSI--DIADVLKEYKSYAASALPPEDVELLGKSVQKVLRGSRLEEIPL.
BYV-HSP70      KLTDGDKALFLKRLJTADYRREARKFSSYDDAVL---NSSELJGRTIPKILRGSRVEKLD-V
```

```
GLRaV2-HSp90  MS-------NYSWESLFKKFYGEADWKKYLSRSIAAHSSEIKTLPDIRLYGGRVVKKSEFESALP
BYV-HSP90     MTTRFSTPANYYWGELFRRFFGGQEWKNLMSEAASVSRPRYSS--DFRFSDGVILSRKTFGESTG
BYSV-HSP90    MSRR-PTFAGYSWGSLFKRHYGEPEWKSYLTETSMKYKPLKSE--SITFYDGSSLTSAELRPARS
CTV-HSP90     MSSH------HVWGSLFRKFYGEAIWKEYLSESTRNFDERNVSL-DHTLSSGVVVRRQSLLNAPQ
Consensus     M..........W..LF....G...WK........................G.............

GLRaV2-HSp90  NSFEQE--LGLFILSEREVGWS-KLCGITVEEAAYDLTNPKAYKFTAETCSPDVKGEGQKYSMED
BYV-HSP90     ESFVREFSL-LLTFPKTYE--VCKLCGVAMELALNGMNRLSDYN-VSEFNIVDVKTVGCKFNIQS
BYSV-HSP90    GT--AEYEIALLIFSDSITKWSEKL-ERSIYRGLNQINNHSIYA-ETELEVTDVKTIGCKFTISA
CTV-HSP90     GTFENE--LALLYNSVVINDFVE-LTGMPLKSLMTGIEDRKV---PDELISVDPHEVGCRFTLND
Consensus     .....E....L.............L..................E....D....G........

GLRaV2-HSp90  VMNFMRLSNLDVNDKMLTEQCWSLSNSCGELINPDDKGRFVALTFKDRDTADDTGAANVECRVGD
BYV-HSP90     VTEFVKKINGNVAEPSLVEHCWSLSNSCGELINPKDTKRFVSLIFKGKDLAESTDEAIVSSSYLD
BYSV-HSP90    VESFM----GGRASAAQVEHCWSLSNSCGELINPNDTARFIQLVFKDKAVTEQAQ-VNTSGSVSD
CTV-HSP90     VESYLMSRGEDFADLAAVEHSWCLSNSCGRLLSSTEIDAYKTLVFT-KNF--DSNVSGVTTKLET
Consensus     V................E..W.LSNSCG.L..........L.F....................

GLRaV2-HSp90  YLVYAMSLFEQRTQKSQSGNISLYEKYCEYIRTYLGSTDLFFTAPDRIPLLTGILYDFCKEYNVF
BYV-HSP90     YLSHCLNLYETCNLSSNSGKKSLYDEFLKHVIDYLENSDLEYRSPSDNPLVAGILYDMCFEYNTL
BYSV-HSP90    YLVYCLQLYDNSKKKSNAGRTQLMESYVSFIRDFFQHSDLYYRSPLDNPLLTGVLYDLCIEHNVL
CTV-HSP90     YLSYCISLYKKHCMKDD-DYFNLILPMFNCLMKVLASLGLFYEKHADNPLLTGMLIEFCLENKVY
Consensus     YL.....L................L................L........PL..G.L....

I
                                                       _____
GLRaV2-HSp90  YSSYKRNVDNFRFFLANYMPLISDVFVFQWVKPAPDV----RLLFELSAAELTLEVPTLSLIDSQ
BYV-HSP90     KSTYLKNIESFDCFLSLYLPLLSEVFSMNWERPAPDV----RLLFELDAAELLLKVPTINMHDST
BYSV-HSP90    RGSYLKNLDNFRLFKQTYLPMIDDIFDYSWELYAPDE----RLLFPIDPYEIIKEVPTMSVIDAN
CTV-HSP90     YSTFKVNLDNVRLFKSKVLPVVLTV----WDISEPDDPMDERVLIPFDPTDFVLDLPKLNIHDTM
Consensus     ......N......F.....P.........W....PD.....R.L............P.....D..

I                                II
              _____                    _____
GLRaV2-HSp90  VVVGHILRYVESYTSDPAIDALEDKLEAILKSSNPRLSTAQLWVGFFCYYGEFRTAQSRVVQRPG
BYV-HSP90     FLYKNKLRYLESYFEDDSNELIKVKVDSLLTRDNPELKLAQRWVGFHCYYGVFRTAQTRKVKRDA
BYSV-HSP90    VVLSNKLVYLDSYLENNSILALEKKIISILCRDNEGIDEGALWAAFFCYYGTYRTARQRVVKRPD
CTV-HSP90     VVVGNQIRQLEYVVESDALDDLSQHVDLRLAADNPDLRVGLRWAGMFVYYGVYRCVVDRAVERPT
Consensus     ....................L...N........W.....YYG..R....R.V.R..

II
                                   _____
GLRaV2-HSp90  VYKTPDSV------GGFEINMKDVEKFFDKLQRELPNVSLRRQFNGARAHEAFKIFKNGNISFRP
BYV-HSP90     EYKLPPAL------GEFVINMSGVEEFFEELQKKMPSISVRRRFCGSLSHEAFSVFKRFGVGFPP
BYSV-HSP90    TYELDGIF------SKPIV-MSGVELFFDELQKRVPDVSLRRRFNGAKAGEAITVFKKLGISFPP
CTV-HSP90     LFRLPQKLLSQDDGESCSLHMGSVEALFNLVQKVNKDINVRRQFMGRHSEVALRLYRNLGLRFPP
Consensus     ................M..VE..F...Q........RR.F.G.....A..........F.P II
                   _____
GLRaV2-HSp90  ISRLNVPREFWYLNIDYFRHANRSGLTEEEILILNNISVDVRKLCAERACN-------TLPSAKR
BYV-HSP90     ITRLNVPVKYSYLNVDYYRHVKRVGLTQDELTILSNIEFDVAEMCCEREVALQAR--RAQRGEKP
BYSV-HSP90    ITRLNAPSKYSYLNIDYFKQANSLGLTEPEKIILCNIAKDVDMMCAQRISSVKA--------KP
CTV-HSP90     ISSVRLPAHHGYLYVDFYKRVPDGAVTADELESLRQLRSSVDVMCKDRVSITPPPFNRLRRGSSR
Consensus     I.....P....YL..D..........T..E...L......V...C..R...............

GLRaV2-HSp90  FSKNHKSNIQSSRQERRIKDPLVVLKDTLYEFQHKRAGWGSRSTRDLGSRADHAKGSG.
BYV-HSP90     FQGWKGTKNEISPHARSSIRVKKNNDSLLNILWKDVGARSQRRLNPLHRK--------H
BYSV-HSP90    IAQRNG--EAINSAKIRTLPTNTLVRALEKCLLNQAPSWWNTTLTNLR
CTV-HSP90     TFRGRGARGASSRHMSRDVATSGFNLPYHGRLY-----------------------STS
Consensus     ............................................................
```

| | | |
|---|---|---|
| GLRaV2 3'-UTR | TTAAGCTGTGTTACTGAGTAATTAAACCAACAAGTGTTGGTGTAATGTGTATGTTGATGTGTAGA | 135 |
| BYS 3'-UTR | TTAAGTCGTCACAGAGTGACAACGGCACCAAGTGCTTAGTGCTTAGTGCTATGTAAATTACGAA | 95 |
| BYSV 3'-UTR | TTAAGCCCTCACAGAGCGAGAACGTTGGCAAGACCAATTAGTGTGTAGTGTAGTATAATTA | 181 |
| CTV 3'-UTR | CTAAGCTCCCACAGAGTGGTAGTGGTCTCAAGTGAGGCTTAACGTATGCGTGAACCAAAGA | 208 |
| Consensus | .TAAG.....AC.GAG..........CAAG.G...T................A | |

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 15500 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
TAAACATTGC GAGAGAACCC CATTAGCGTC TCCGGGGTGA ACTTGGGAAG GTCTGCCGCC        60

GCTCAGGTTA TTTATTTCGG CAGTTTCACG CAGCCCTTCG CGTTGTATCC GCGCCAAGAG       120

AGCGCGATCG TAAAAACGCA ACTTCCACCG GTCAGTGTAG TGAAGGTGGA GTGCGTAGCT       180

GCGGAGGTAG CTCCCGACAG GGGCGTGGTC GACAAGAAAC CTACGTCTGT TGGCGTTCCC       240

CCGCAGCGCG GTGTGCTTTC TTTTCCGACG GTGGTTCGGA ACCGCGGCGA CGTGATAATC       300

ACAGGGGTGG TGCATGAAGC CCTGAAGAAA ATTAAAGACG GGCTCTTACG CTTCCGCGTA       360

GGCGGTGACA TGCGTTTTTC GAGATTTTTC TCATCGAACT ACGGCTGCAG ATTCGTCGCG       420

AGCGTGCGTA CGAACACTAC AGTTTGGCTA AATTGCACGA AAGCGAGTGG TGAGAAATTC       480

TCACTCGCCG CCGCGTGCAC GGCGGATTAC GTGGCGATGC TGCGTTATGT GTGTGGCGGG       540

AAATTTCCAC TCGTCCTCAT GAGTAGAGTT ATTTACCCGG ATGGGCGCTG TTACTTGGCC       600

CATATGAGGT ATTTGTGCGC CTTTTACTGT CGCCCGTTTA GAGAGTCGGA TTATGCCCTC       660

GGAATGTGGC CTACGGTGGC GCGTCTCAGG GCATGCGTTG AGAAGAACTT CGGTGTCGAA       720

GCTTGTGGCA TAGCTCTTCG TGGCTATTAC ACCTCTCGCA ATGTTTATCA CTGTGATTAT       780
```

-continued

```
GACTCTGCTT ATGTAAAATA TTTTAGAAAC CTTTCCGGCC GCATTGGCGG TGGTTCGTTC      840

GATCCGACAT CTTTAACCTC CGTAATAACG GTGAAGATTA GCGGTCTTCC AGGTGGTCTT      900

CCTAAAAATA TAGCGTTTGG TGCCTTCCTG TGCGATATAC GTTACGTCGA ACCGGTAGAC      960

TCGGCGGCA TTCAATCGAG CGTTAAGACG AAACGTGAAG ATGCGCACCG AACCGTAGAG      1020

GAACGGGCGG CCGGCGGATC CGTCGAGCAA CCGCGACAAA AGAGGATAGA TGAGAAAGGT     1080

TGCGGCAGAG TTCCTAGTGG AGGTTTTTCG CATCTCCTGG TCGGCAACCT TAACGAAGTT     1140

AGGAGGAAGG TAGCTGCCGG ACTTCTACGC TTTCGCGTTG GCGGTGATAT GGATTTTCAT     1200

CGCTCGTTCT CCACCCAAGC GGGCCACCGC TTGCTGGTGT GGCGCCGCTC GAGCCGGAGC     1260

GTGTGCCTTG AACTTTACTC ACCATCTAAA AACTTTTTGC GTTACGATGT CTTGCCCTGT     1320

TCTGGAGACT ATGCAGCGAT GTTTTCTTTC GCGGCGGGCG GCCGTTTCCC TTTAGTTTTG     1380

ATGACTAGAA TTAGATACCC GAACGGGTTT TGTTACTTGG CTCACTGCCG GTACGCGTGC     1440

GCGTTTCTCT TAAGGGGTTT TGATCCGAAG CGTTTCGACA TCGGTGCTTT CCCCACCGCG     1500

GCCAAGCTCA GAAACCGTAT GGTTTCGGAG CTTGGTGAAA GAAGTTTAGG TTTGAACTTG     1560

TACGGCGCAT ATACGTCACG CGGCGTCTTT CACTGCGATT ATGACGCTAA GTTTATAAAG     1620

GATTTGCGTC TTATGTCAGC AGTTATAGCT GGAAAGGACG GGGTGGAAGA GGTGGTACCT     1680

TCTGACATAA CTCCTGCCAT GAAGCAGAAA ACGATCGAAG CCGTGTATGA TAGATTATAT     1740

GGCGGCACTG ACTCGTTGCT GAAACTGAGC ATCGAGAAAG ACTTAATCGA TTTCAAAAAT     1800

GACGTGCAGA GTTTGAAGAA AGATCGGCCG ATTGTCAAAG TGCCCTTTTA CATGTCGGAA     1860

GCAACACAGA ATTCGCTGAC GCGTTTCTAC CCTCAGTTCG AACTTAAGTT TTCGCACTCC     1920

TCGCATTCAG ATCATCCCGC CGCCGCCGCT TCTAGACTGC TGGAAAATGA AACGTTAGTG     1980

CGCTTATGTG GTAATAGCGT TTCAGATATT GGAGGTTGTC CTCTTTTCCA TTTGCATTCC     2040

AAGACGCAAA GACGGGTTCA CGTATGTAGG CCTGTGTTGG ATGGCAAGGA TGCGCAGCGT     2100

CGCGTGGTGC GTGATTTGCA GTATTCCAAC GTGCGTTTGG GAGACGATGA TAAAATTTTG     2160

GAAGGGCCAC GCAATATCGA CATTTGCCAC TATCCTCTGG GCGCGTGTGA CCACGAAAGT     2220

AGTGCTATGA TGATGGTGCA GGTGTATGAC GCGTCCCTTT ATGAGATATG TGGCGCCATG     2280

ATCAAGAAGA AAAGCCGCAT AACGTACTTA ACCATGGTCA CGCCCGGCGA GTTTCTTGAC     2340

GGACGCGAAT GCGTCTACAT GGAGTCGTTA GACTGTGAGA TTGAAGTTGA TGTGCACGCG     2400

GACGTCGTAA TGTACAAATT CGGTAGTTCT TGCTATTCGC ACAAGCTTTC AATCATCAAG     2460

GACATCATGA CCACTCCGTA CTTGACACTA GGTGGTTTTC TATTCAGCGT GGAGATGTAT     2520

GAGGTGCGTA TGGGCGTGAA TTACTTCAAG ATTACGAAGT CCGAAGTATC GCCTAGCATT     2580

AGCTGCACCA AGCTCCTGAG ATACCGAAGA GCTAATAGTG ACGTGGTTAA AGTTAAACTT     2640

CCACGTTTCG ATAAGAAACG TCGCATGTGT CTGCCTGGGT ATGACACCAT ATACCTAGAT     2700

TCGAAGTTTG TGAGTCGCGT TTTCGATTAT GTCGTGTGTA ATTGCTCTGC CGTGAACTCA     2760

AAAACTTTCG AGTGGGTGTG GAGTTTCATT AAGTCTAGTA AGTCGAGGGT GATTATTAGC     2820

GGTAAAATAA TTCACAAGGA TGTGAATTTG GACCTCAAGT ACGTCGAGAG TTTCGCCGCG     2880

GTTATGTTGG CCTCTGGCGT GCGCAGTAGA CTAGCGTCCG AGTACCTTGC TAAGAACCTT     2940

AGTCATTTTT CGGGAGATTG CTCCTTTATT GAAGCCACGT CTTTCGTGTT GCGTGAGAAA     3000

ATCAGAAACA TGACTCTGAA TTTTAACGAA AGACTTTTAC AGTTAGTGAA GCGCGTTGCC     3060

TTTGCGACCT TGGACGTGAG TTTTCTAGAT TTAGATTCAA CTCTTGAATC AATAACTGAT     3120

TTTGCCGAGT GTAAGGTAGC GATTGAACTC GACGAGTTGG GTTGCTTGAG AGCGGAGGCC     3180
```

```
GAGAATGAAA AAATCAGGAA TCTGGCGGGA GATTCGATTG CGGCTAAACT CGCGAGCGAG    3240

ATAGTGGTCG ATATTGACTC TAAGCCTTCA CCGAAGCAGG TGGGTAATTC GTCATCCGAA    3300

AACGCCGATA AGCGGGAAGT TCAGAGGCCC GGTTTGCGTG GTGGTTCTAG AAACGGGGTT    3360

GTTGGGGAGT TCCTTCACTT CGTCGTGGAT TCTGCCTTGC GTCTTTTCAA ATACGCGACG    3420

GATCAACAAC GGATCAAGTC TTACGTGCGT TTCTTGGACT CGGCGGTCTC ATTCTTGGAT    3480

TACAACTACG ATAATCTATC GTTTATACTG CGAGTGCTTT CGGAAGGTTA TTCGTGTATG    3540

TTCGCGTTTT TGGCGAATCG CGGCGACTTA TCTAGTCGTG TCCGTAGCGC GGTGTGTGCT    3600

GTGAAAGAAG TTGCTACCTC ATGCGCGAAC GCGAGCGTTT CTAAAGCCAA GGTTATGATT    3660

ACCTTCGCAG CGGCCGTGTG TGCTATGATG TTTAATAGCT GCGGTTTTTC AGGCGACGGT    3720

CGGGAGTATA AATCGTATAT ACATCGTTAC ACGCAAGTAT TGTTTGACAC TATCTTTTTT    3780

GAGGACAGCA GTTACCTACC CATAGAAGTT CTGAGTTCGG CGATATGCGG TGCTATCGTC    3840

ACACTTTTCT CCTCGGGCTC GTCCATAAGT TTAAACGCCT TCTTACTTCA AATTACCAAA    3900

GGATTCTCCC TAGAGGTTGT CGTCCGGAAT GTTGTGCGAG TCACGCATGG TTTGAGCACC    3960

ACAGCGACCG ACGGCGTCAT ACGTGGGGTT TTCTCCCAAA TTGTGTCTCA CTTACTTGTT    4020

GGAAATACGG GTAATGTGGC TTACCAGTCA GCTTTCATTG CCGGGGTGGT GCCTCTTTTA    4080

GTTAAAAAGT GTGTGAGCTT AATCTTCATC TTGCGTGAAG ATACTTATTC CGGTTTTATT    4140

AAGCACGGAA TCAGTGAATT CTCTTTCCTT AGTAGTATTC TGAAGTTCTT GAAGGGTAAG    4200

CTTGTGGACG AGTTGAAATC GATTATTCAA GGGGTTTTTG ATTCCAACAA GCACGTGTTT    4260

AAAGAAGCTA CTCAGGAAGC GATTCGTACG ACGGTCATGC AAGTGCCTGT CGCTGTAGTG    4320

GATGCCCTTA AGAGCGCCGC GGGAAAAATT TATAACAATT TTACTAGTCG ACGTACCTTT    4380

GGTAAGGATG AAGGCTCCTC TAGCGACGGC GCATGTGAAG AGTATTTCTC ATGCGACGAA    4440

GGTGAAGGTC CGGGTCTGAA AGGGGGTTCC AGCTATGGCT TCTCAATTTT AGCGTTCTTT    4500

TCACGCATTA TGTGGGGAGC TCGTCGGCTT ATTGTTAAGG TGAAGCATGA GTGTTTTGGG    4560

AAACTTTTTG AATTTCTATC GCTCAAGCTT CACGAATTCA GGACTCGCGT TTTTGGGAAG    4620

AATAGAACGG ACGTGGGAGT TTACGATTTT TTGCCCACGG GCATCGTGGA AACGCTCTCA    4680

TCGATAGAAG AGTGCGACCA AATTGAAGAA CTTCTCGGCG ACGACCTGAA AGGTGACAAG    4740

GATGCTTCGT TGACCGATAT GAATTACTTT GAGTTCTCAG AAGACTTCTT AGCCTCTATC    4800

GAGGAGCCGC CTTTCGCTGG ATTGCGAGGA GGTAGCAAGA ACATCGCGAT TTTGGCGATT    4860

TTGGAATACG CGCATAATTT GTTTCGCATT GTCGCAAGCA AGTGTTCGAA ACGACCTTTA    4920

TTTCTTGCTT TCGCCGAACT CTCAAGCGCC CTTATCGAGA AATTTAAGGA GGTTTTCCCT    4980

CGTAAGAGCC AGCTCGTCGC TATCGTGCGC GAGTATACTC AGAGATTCCT CCGAAGTCGC    5040

ATGCGTGCGT TGGGTTTGAA TAACGAGTTC GTGGTAAAAT CTTTCGCCGA TTTGCTACCC    5100

GCATTAATGA AGCGGAAGGT TTCAGGTTCG TTCTTAGCTA GTGTTTATCG CCCACTTAGA    5160

GGTTTCTCAT ATATGTGTGT TTCAGCGGAG CGACGTGAAA AGTTTTTTGC TCTCGTGTGT    5220

TTAATCGGGT TAAGTCTCCC TTTCTTCGTG CGCATCGTAG GAGCGAAAGC GTGCGAAGAA    5280

CTCGTGTCCT CAGCGCGTCG CTTTTATGAG CGTATTAAAA TTTTTCTAAG GCAGAAGTAT    5340

GTCTCTCTTT CTAATTTCTT TTGTCACTTG TTTAGCTCTG ACGTTGATGA CAGTTCCGCA    5400

TCTGCAGGGT TGAAAGGTGG TGCGTCGCGA ATGACGCTCT TCCACCTTCT GGTTCGCCTT    5460

GCTAGTGCCC TCCTATCGTT AGGGTGGGAA GGGTTAAAGC TACTCTTATC GCACCACAAC    5520
```

-continued

| | |
|---|---|
| TTGTTATTTT TGTGTTTTGC ATTGGTTGAC GATGTGAACG TCCTTATCAA AGTTCTTGGG | 5580 |
| GGTCTTTCTT TCTTTGTGCA ACCAATCTTT TCCTTGTTTG CGGCGATGCT TCTACAACCG | 5640 |
| GACAGGTTTG TGGAGTATTC CGAGAAACTT GTTACAGCGT TTGAATTTTT CTTAAAATGT | 5700 |
| TCGCCTCGCG CGCCTGCACT ACTCAAAGGG TTTTTTGAGT GCGTGGCGAA CAGCACTGTG | 5760 |
| TCAAAAACCG TTCGAAGACT TCTTCGCTGT TTCGTGAAGA TGCTCAAACT TCGAAAAGGG | 5820 |
| CGAGGGTTGC GTGCGGATGG TAGGGGTCTC CATCGGCAGA AAGCCGTACC CGTCATACCT | 5880 |
| TCTAATCGGG TCGTGACCGA CGGGGTTGAA AGACTTTCGG TAAAGATGCA AGGAGTTGAA | 5940 |
| GCGTTGCGTA CCGAATTGAG AATCTTAGAA GATTTAGATT CTGCCGTGAT CGAAAAACTC | 6000 |
| AATAGACGCA GAAATCGTGA CACTAATGAC GACGAATTTA CGCGCCCTGC TCATGAGCAG | 6060 |
| ATGCAAGAAG TCACCACTTT CTGTTCGAAA GCCAACTCTG CTGGTTTGGC CCTGGAAAGG | 6120 |
| GCAGTGCTTG TGGAAGACGC TATAAAGTCG GAGAAACTTT CTAAGACGGT TAATGAGATG | 6180 |
| GTGAGGAAAG GGAGTACCAC CAGCGAAGAA GTGGCCGTCG CTTTGTCGGA CGATGAAGCC | 6240 |
| GTGGAAGAAA TCTCTGTTGC TGACGAGCGA GACGATTCGC CTAAGACAGT CAGGATAAGC | 6300 |
| GAATACCTAA ATAGGTTAAA CTCAAGCTTC GAATTCCCGA AGCCTATTGT TGTGGACGAC | 6360 |
| AACAAGGATA CCGGGGGTCT AACGAACGCC GTGAGGGAGT TTTATTATAT GCAAGAACTT | 6420 |
| GCTCTTTTCG AAATCCACAG CAAACTGTGC ACCTACTACG ATCAACTGCG CATAGTCAAC | 6480 |
| TTCGATCGTT CCGTAGCACC ATGCAGCGAA GATGCTCAGC TGTACGTACG GAAGAACGGC | 6540 |
| TCAACGATAG TGCAGGGTAA AGAGGTACGT TTGCACATTA AGGATTTCCA CGATCACGAT | 6600 |
| TTCCTGTTTG ACGGAAAAAT TTCTATTAAC AAGCGGCGGC GAGGCGGAAA TGTTTTATAT | 6660 |
| CACGACAACC TCGCGTTCTT GGCGAGTAAT TTGTTCTTAG CCGGCTACCC CTTTTCAAGG | 6720 |
| AGCTTCGTCT TCACGAATTC GTCGGTCGAT ATTCTCCTCT ACGAAGCTCC ACCCGGAGGT | 6780 |
| GGTAAGACGA CGACGCTGAT TGACTCGTTC TTGAAGGTCT TCAAGAAAGG TGAGGTTTCC | 6840 |
| ACCATGATCT TAACCGCCAA CAAAAGTTCG CAGGTTGAGA TCCTAAAGAA AGTGGAGAAG | 6900 |
| GAAGTGTCTA ACATTGAATG CCAGAAACGT AAAGACAAAA GATCTCCGAA AAAGAGCATT | 6960 |
| TACACCATCG ACGCTTATTT AATGCATCAC CGTGGTTGTG ATGCAGACGT TCTTTTCATC | 7020 |
| GATGAGTGTT TCATGGTTCA TGCGGGTAGC GTACTAGCTT GCATTGAGTT CACGAGGTGT | 7080 |
| CATAAAGTAA TGATCTTCGG GGATAGCCGG CAGATTCACT ACATTGAAAG GAACGAATTG | 7140 |
| GACAAGTGTT TGTATGGGGA TCTCGACAGG TTCGTGGACC TGCAGTGTCG GGTTTATGGT | 7200 |
| AATATTTCGT ACCGTTGTCC ATGGGATGTG TGCGCTTGGT TAAGCACAGT GTATGGCAAC | 7260 |
| CTAATCGCCA CCGTGAAGGG TGAAAGCGAA GGTAAGAGCA GCATGCGCAT TAACGAAATT | 7320 |
| AATTCAGTCG ACGATTTAGT CCCCGACGTG GGTTCCACGT TTCTGTGTAT GCTTCAGTCG | 7380 |
| GAGAAGTTGG AAAATCAGCAA GCACTTTATT CGCAAGGGTT TGACTAAACT TAACGTTCTA | 7440 |
| ACGGTGCATG AGGCGCAAGG TGAGACGTAT GCGCGTGTGA ACCTTGTGCG ACTTAAGTTT | 7500 |
| CAGGAGGATG AACCCTTTAA ATCTATCAGG CACATAACCG TCGCTCTTTC TCGTCACACC | 7560 |
| GACAGCTTAA CTTATAACGT CTTAGCTGCT CGTCGAGGTG ACGCCACTTG CGATGCCATC | 7620 |
| CAGAAGGCTG CGGAATTGGT GAACAAGTTT CGCGTTTTTC CTACATCTTT TGGTGGTAGT | 7680 |
| GTTATCAATC TCAACGTGAA GAAGGACGTG GAAGATAACA GTAGGTGCAA GGCTTCGTCG | 7740 |
| GCACCATTGA GCGTAATCAA CGACTTTTTG AACGAAGTTA ATCCCGGTAC TGCGGTGATT | 7800 |
| GATTTTGGTG ATTTGTCCGC GGACTTCAGT ACTGGGCCTT TTGAGTGCGG TGCCAGCGGT | 7860 |
| ATTGTGGTGC GGGACAACAT CTCCTCCAGC AACATCACTG ATCACGATAA GCAGCGTGTT | 7920 |

-continued

```
TAGCGTAGTT CGGTCGCAGG CGATTCCGCG TAGAAAACCT TCTCTACAAG AAAATTTGTA   7980

TTCGTTTGAA GCGCGGAATT ATAACTTCTC GACTTGCGAC CGTAACACAT CTGCTTCAAT   8040

GTTCGGAGAG GCTATGGCGA TGAACTGTCT TCGTCGTTGC TTCGACCTAG ATGCCTTTTC   8100

GTCCCTGCGT GATGATGTGA TTAGTATCAC ACGTTCAGGC ATCGAACAAT GGCTGGAGAA   8160

ACGTACTCCT AGTCAGATTA AAGCATTAAT GAAGGATGTT GAATCGCCTT TGGAAATTGA   8220

CGATGAAATT TGTCGTTTTA AGTTGATGGT GAAGCGTGAC GCTAAGGTGA AGTTAGACTC   8280

TTCTTGTTTA ACTAAACACA GCGCCGCTCA AAATATCATG TTTCATCGCA AGAGCATTAA   8340

TGCTATCTTC TCTCCTATCT TTAATGAGGT GAAAAACCGA ATAATGTGCT GTCTTAAGCC   8400

TAACATAAAG TTTTTTACGG AGATGACTAA CAGGGATTTT GCTTCTGTTG TCAGCAACAT   8460

GCTTGGTGAC GACGATGTGT ACCATATAGG TGAAGTTGAT TTCTCAAAGT ACGACAAGTC   8520

TCAAGATGCT TTCGTGAAGG CTTTTGAAGA AGTAATGTAT AAGGAACTCG GTGTTGATGA   8580

AGAGTTGCTG GCTATCTGGA TGTGCGGCGA GCGGTTATCG ATAGCTAACA CTCTCGATGG   8640

TCAGTTGTCC TTCACGATCG AGAATCAAAG GAAGTCGGGA GCTTCGAACA CTTGGATTGG   8700

TAACTCTCTC GTCACTTTGG GTATTTTAAG TCTTTACTAC GACGTTAGAA ATTTCGAGGC   8760

GTTGTACATC TCGGGCGATG ATTCTTTAAT TTTTTCTCGC AGCGAGATTT CGAATTATGC   8820

CGACGACATA TGCACTGACA TGGGTTTTGA GACAAAATTT ATGTCCCCAA GTGTCCCGTA   8880

CTTTTGTTCT AAATTTGTTG TTATGTGTGG TCATAAGACG TTTTTTGTTC CCGACCCGTA   8940

CAAGCTTTTT GTCAAGTTGG GAGCAGTCAA AGAGGATGTT TCAATGGATT TCCTTTTCGA   9000

GACTTTTACC TCCTTTAAAG ACTTAACCTC CGATTTTAAC GACGAGCGCT TAATTCAAAA   9060

GCTCGCTGAA CTTGTGGCTT TAAAATATGA GGTTCAAACC GGCAACACCA CCTTGGCGTT   9120

AAGTGTGATA CATTGTTTGC GTTCGAATTT CCTCTCGTTT AGCAAGTTAT ATCCTCGCGT   9180

GAAGGGATGG CAGGTTTTTT ACACGTCGGT TAAGAAAGCG CTTCTCAAGA GTGGGTGTTC   9240

TCTCTTCGAC AGTTTCATGA CCCCTTTTGG TCAGGCTGTC ATGGTTTGGG ATGATGAGTA   9300

GCGCTAACTT GTGCGCAGTT TCTTTGTTCG TGACATACAC CTTGTGTGTC ACCGTGCGTT   9360

TATAATGAAT CAGGTTTTGC AGTTTGAATG TTTGTTTCTG CTGAATCTCG CGGTTTTTGC   9420

TGTGACTTTC ATTTTCATTC TTCTGGTCTT CCGCGTGATT AAGTCTTTTC GCCAGAAGGG   9480

TCACGAAGCA CCTGTTCCCG TTGTTCGTGG CGGGGGTTTT TCAACCGTAG TGTAGTCAAA   9540

AGACGCGCAT ATGGTAGTTT TCGGTTTGGA CTTTGGCACC ACATTCTCTA CGGTGTGTGT   9600

GTACAAGGAT GGACGAGTTT TTTCATTCAA GCAGAATAAT TCGGCGTACA TCCCCACTTA   9660

CCTCTATCTC TTCTCCGATT CTAACCACAT GACTTTTGGT TACGAGGCCG AATCACTGAT   9720

GAGTAATCTG AAAGTTAAAG GTTCGTTTTA TAGAGATTTA AAACGTTGGG TGGGTTGCGA   9780

TTCGAGTAAC CTCGACGCGT ACCTTGACCG TTTAAAACCT CATTACTCGG TCCGCTTGGT   9840

TAAGATCGGC TCTGGCTTGA ACGAAACTGT TTCAATTGGA AACTTCGGGG GCACTGTTAA   9900

GTCTGAGGCT CATCTGCCAG GGTTGATAGC TCTCTTTATT AAGGCTGTCA TTAGTTGCGC   9960

GGAGGGCGCG TTTGCGTGCA CTTGCACCGG GGTTATTTGT TCAGTACCTG CCAATTATGA  10020

TAGCGTTCAA AGGAATTTCA CTGATCAGTG TGTTTCACTC AGCGGTTATC AGTGCGTATA  10080

TATGATCAAT GAACCTTCAG CGGCTGCGCT ATCTGCGTGT AATTCGATTG GAAAGAAGTC  10140

CGCAAATTTG GCTGTTTACG ATTTCGGTGG TGGGACCTTC GACGTGTCTA TCATTTCATA  10200

CCGCAACAAT ACTTTTGTTG TGCGAGCTTC TGGAGGCGAT CTAAATCTCG GTGGAAGGGA  10260
```

```
TGTTGATCGT GCGTTTCTCA CGCACCTCTT CTCTTTAACA TCGCTGGAAC CTGACCTCAC   10320

TTTGGATATC TCGAATCTGA AGAATCTTT  ATCAAAAACG GACGCAGAGA TAGTTTACAC   10380

TTTGAGAGGT GTCGATGGAA GAAAAGAAGA CGTTAGAGTA AACAAAAACA TTCTTACGTC   10440

GGTGATGCTC CCCTACGTGA ACAGAACGCT TAAGATATTA GAGTCAACCT TAAAATCGTA   10500

TGCTAAGAGT ATGAATGAGA GTGCGCGAGT TAAGTGCGAT TTAGTGCTGA TAGGAGGATC   10560

TTCATATCTT CCTGGCCTGG CAGACGTACT AACGAAGCAT CAGAGCGTTG ATCGTATCTT   10620

AAGAGTTTCG GATCCTCGGG CTGCCGTGGC CGTCGGTTGC GCATTATATT CTTCATGCCT   10680

CTCAGGATCT GGGGGGTTGC TACTGATCGA CTGTGCAGCT CACACTGTCG CTATAGCGGA   10740

CAGAAGTTGT CATCAAATCA TTTGCGCTCC AGCGGGGGCA CCGATCCCCT TTTCAGGAAG   10800

CATGCCTTTG TACTTAGCCA GGGTCAACAA GAACTCGCAG CGTGAAGTCG CCGTGTTTGA   10860

AGGGGAGTAC GTTAAGTGCC CTAAGAACAG AAAGATCTGT GGAGCAAATA TAAGATTTTT   10920

TGATATAGGA GTGACGGGTG ATTCGTACGC ACCCGTTACC TTCTATATGG ATTTCTCCAT   10980

TTCAAGCGTA GGAGCCGTTT CATTCGTGGT GAGAGGTCCT GAGGGTAAGC AAGTGTCACT   11040

CACTGGAACT CCAGCGTATA ACTTTTCGTC TGTGGCTCTC GGATCACGCA GTGTCCGAGA   11100

ATTGCATATT AGTTTAAATA ATAAAGTTTT TCTCGGTTTG CTTCTACATA GAAAGGCGGA   11160

TCGACGAATA CTTTTCACTA AGGATGAAGC GATTCGATAC GCCGATTCAA TTGATATCGC   11220

GGATGTGCTA AAGGAATATA AAGTTACGC  GGCCAGTGCC TTACCACCAG ACGAGGATGT   11280

CGAATTACTC CTGGGAAAGT CTGTTCAAAA AGTTTTACGG GGAAGCAGAC TGGAAGAAAT   11340

ACCTCTCTAG GAGCATAGCA GCACACTCAA GTGAAATTAA AACTCTACCA GACATTCGAT   11400

TGTACGGCGG TAGGGTTGTA AAGAAGTCCG AATTCGAATC AGCACTTCCT AATTCTTTTG   11460

AACAGGAATT AGGACTGTTC ATACTGAGCG AACGGGAAGT GGGATGGAGC AAATTATGCG   11520

GAATAACGGT GGAAGAAGCA GCATACGATC TTACGAATCC CAAGGCTTAT AAATTCACTG   11580

CCGAGACATG TAGCCCGGAT GTAAAAGGTG AAGGACAAAA ATACTCTATG AAGACGTGA    11640

TGAATTTCAT GCGTTTATCA AATCTGGATG TTAACGACAA GATGCTGACG GAACAGTGTT   11700

GGTCGCTGTC CAATTCATGC GGTGAATTGA TCAACCCAGA CGACAAAGGG CGATTCGTGG   11760

CTCTCACCTT TAAGGACAGA GACACAGCTG ATGACACGGG TGCCGCCAAC GTGGAATGTC   11820

GCGTGGGCGA CTATCTAGTT TACGCTATGT CCCTGTTTGA GCAGAGGACC CAAAAATCGC   11880

AGTCTGGCAA CATCTCTCTG TACGAAAAGT ACTGTGAATA CATCAGGACC TACTTAGGGA   11940

GTACAGACCT GTTCTTCACA GCGCCGGACA GGATTCCGTT ACTTACGGGC ATCCTATACG   12000

ATTTTTGTAA GGAATACAAC GTTTTCTACT CGTCATATAA GAGAAACGTC GATAATTTCA   12060

GATTCTTCTT GGCGAATTAT ATGCCTTTGA TATCTGACGT CTTTGTCTTC CAGTGGGTAA   12120

AACCCGCGCC GGATGTTCGG CTGCTTTTTG AGTTAAGTGC AGCGGAACTA ACGCTGGAGG   12180

TTCCCACACT GAGTTTGATA GATTCTCAAG TTGTGGTAGG TCATATCTTA AGATACGTAG   12240

AATCCTACAC ATCAGATCCA GCCATCGACG CGTTAGAAGA CAAACTGGAA GCGATACTGA   12300

AAAGTAGCAA TCCCCGTCTA TCGACAGCGC AACTATGGGT TGGTTTCTTT TGTTACTATG   12360

GTGAGTTTCG TACGGCTCAA AGTAGAGTAG TGCAAAGACC AGGCGTATAC AAAACACCTG   12420

ACTCAGTGGG TGGATTTGAA ATAAACATGA AAGATGTTGA GAAATTCTTC GATAAACTTC   12480

AGAGAGAATT GCCTAATGTA TCTTTGCGGC GTCAGTTTAA CGGAGCTAGA GCGCATGAGG   12540

CTTTCAAAAT ATTTAAAAAC GGAAATATAA GTTTCAGACC TATATCGCGT TTAAACGTGC   12600

CTAGAGAGTT CTGGTATCTG AACATAGACT ACTTCAGGCA CGCGAATAGG TCCGGGTTAA   12660
```

-continued

```
CCGAAGAAGA AATACTCATC CTAAACAACA TAAGCGTTGA TGTTAGGAAG TTATGCGCTG   12720

AGAGAGCGTG CAATACCCTA CCTAGCGCGA AGCGCTTTAG TAAAAATCAT AAGAGTAATA   12780

TACAATCATC ACGCCAAGAG CGGAGGATTA AAGACCCATT GGTAGTCCTG AAAGACACTT   12840

TATATGAGTT CCAACACAAG CGTGCCGGTT GGGGGTCTCG AAGCACTCGA GACCTCGGGA   12900

GTCGTGCTGA CCACGCGAAA GGAAGCGGTT GATAAGTTTT TTAATGAACT AAAAAACGAA   12960

AATTACTCAT CAGTTGACAG CAGCCGATTA AGCGATTCGG AAGTAAAAGA AGTGTTAGAG   13020

AAAAGTAAAG AAAGTTTCAA AAGCGAACTG GCCTCCACTG ACGAGCACTT CGTCTACCAC   13080

ATTATATTTT TCTTAATCCG ATGTGCTAAG ATATCGACAA GTGAAAAGGT GAAGTACGTT   13140

GGTAGTCATA CGTACGTGGT CGACGGAAAA ACGTACACCG TTCTTGACGC TTGGGTATTC   13200

AACATGATGA AAAGTCTCAC GAAGAAGTAC AAACGAGTGA ATGGTCTGCG TGCGTTCTGT   13260

TGCGCGTGCG AAGATCTATA TCTAACCGTC GCACCAATAA TGTCAGAACG CTTTAAGACT   13320

AAAGCCGTAG GGATGAAAGG TTTGCCTGTT GGAAAGGAAT ACTTAGGCGC CGACTTTCTT   13380

TCGGAACTA GCAAACTGAT GAGCGATCAC GACAGGGCGG TCTCCATCGT TGCAGCAAAA   13440

AACGCTGTCG ATCGTAGCGC TTTCACGGGT GGGGAGAGAA AGATAGTTAG TTTGTATGAT   13500

CTAGGGAGGT ACTAAGCACG GTGTGCTATA GTGCGTGCTA TAATAATAAA CACTAGTGCT   13560

TAAGTCGCGC AGAAGAAAAC GCTATGGAGT TGATGTCCGA CAGCAACCTT AGCAACCTGG   13620

TGATAACCGA CGCCTCTAGT CTAAATGGTG TCGACAAGAA GCTTTTATCT GCTGAAGTTG   13680

AAAAAATGTT GGTGCAGAAA GGGGCTCCTA ACGAGGGTAT AGAAGTGGTG TTCGGTCTAC   13740

TCCTTTACGC ACTCGCGGCA AGAACCACGT CTCCTAAGGT TCAGCGCGCA GATTCAGACG   13800

TTATATTTTC AAATAGTTTC GGAGAGAGGA ATGTGGTAGT AACAGAGGGT GACCTTAAGA   13860

AGGTACTCGA CGGGTGTGCG CCTCTCACTA GGTTCACTAA TAAACTTAGA ACGTTCGGTC   13920

GTACTTTCAC TGAGGCTTAC GTTGACTTTT GTATCGCGTA TAAGCACAAA TTACCCCAAC   13980

TCAACGCCGC GGCGGAATTG GGGATTCCAG CTGAAGATTC GTACTTAGCT GCAGATTTTC   14040

TGGGTACTTG CCCGAAGCTC TCTGAATTAC AGCAAAGTAG GAAGATGTTC GCGAGTATGT   14100

ACGCTCTAAA AACTGAAGGT GGAGTGGTAA ATACACCAGT GAGCAATCTG CGTCAGCTAG   14160

GTAGAAGGGA AGTTATGTAA TGGAAGATTA CGAAGAAAAA TCCGAATCGC TCATACTGCT   14220

ACGCACGAAT CTGAACACTA TGCTTTTAGT GGTCAAGTCC GATGCTAGTG TAGAGCTGCC   14280

TAAACTACTA ATTTGCGGTT ACTTACGAGT GTCAGGACGT GGGGAGGTGA CGTGTTGCAA   14340

CCGTGAGGAA TTAACAAGAG ATTTTGAGGG CAATCATCAT ACGGTGATCC GTTCTAGAAT   14400

CATACAATAT GACAGCGAGT CTGCTTTTGA GGAATTCAAC AACTCTGATT GCGTAGTGAA   14460

GTTTTTCCTA GAGACTGGTA GTGTCTTTTG GTTTTTCCTT CGAAGTGAAA CCAAAGGTAG   14520

AGCGGTGCGA CATTTGCGCA CCTTCTTCGA AGCTAACAAT TTCTTCTTTG GATCGCATTG   14580

CGGTACCATG GAGTATTGTT TGAAGCAGGT ACTAACTGAA ACTGAATCTA TAATCGATTC   14640

TTTTTGCGAA GAAAGAAATC GTTAAGATGA GGGTTATAGT GTCTCCTTAT GAAGCTGAAG   14700

ACATTCTGAA AAGATCGACT GACATGTTAC GAAACATAGA CAGTGGGGTC TTGAGCACTA   14760

AAGAATGTAT CAAGGCATTC TCGACGATAA CGCGAGACCT ACATTGTGCG AAGGCTTCCT   14820

ACCAGTGGGG TGTTGACACT GGGTTATATC AGCGTAATTG CGCTGAAAAA CGTTTAATTG   14880

ACACGGTGGA GTCAAACATA CGGTTGGCTC AACCTCTCGT GCGTGAAAAA GTGGCGGTTC   14940

ATTTTTGTAA GGATGAACCA AAAGAGCTAG TAGCATTCAT CACGCGAAAG TACGTGGAAC   15000
```

```
TCACGGGCGT GGGAGTGAGA GAAGCGGTGA AGAGGGAAAT GCGCTCTCTT ACCAAAACAG      15060

TTTTAAATAA AATGTCTTTG GAAATGGCGT TTTACATGTC ACCACGAGCG TGGAAAAACG      15120

CTGAATGGTT AGAACTAAAA TTTTCACCTG TGAAAATCTT TAGAGATCTG CTATTAGACG      15180

TGGAAACGCT CAACGAATTG TGCGCCGAAG ATGATGTTCA CGTCGACAAA GTAAATGAGA      15240

ATGGGGACGA AAATCACGAC CTCGAACTCC AAGACGAATG TTAAACATTG GTTAAGTTTA      15300

ACGAAAATGA TTAGTAAATA ATAAATCGAA CGTGGGTGTA TCTACCTGAC GTATCAACTT      15360

AAGCTGTTAC TGAGTAATTA AACCAACAAG TGTTGGTGTA ATGTGTATGT TGATGTAGAG      15420

AAAAATCCGT TTGTAGAACG GTGTTTTTCT CTTCTTTATT TTTAAAAAAA AAATAAAAAA      15480

AAAAAAAAAA AAGCGGCCGC                                                  15500
```

(2) INFORMATION FOR SEQ ID NO:2:

(i) SEQUENCE CHARACTERISTICS:
        (A) LENGTH: 7920 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
ACATTGCGAG AGAACCCCAT TAGCGTCTCC GGGGTGAACT TGGGAAGGTC TGCCGCCGCT        60

CAGGTTATTT ATTTCGGCAG TTTCACGCAG CCCTTCGCGT TGTATCCGCG CCAAGAGAGC       120

GCGATCGTAA AAACGCAACT TCCACCGGTC AGTGTAGTGA AGGTGGAGTG CGTAGCTGCG       180

GAGGTAGCTC CCGACAGGGG CGTGGTCGAC AAGAAACCTA CGTCTGTTGG CGTTCCCCCG       240

CAGCGCGGTG TGCTTTCTTT TCCGACGGTG GTTCGGAACC GCGGCGACGT GATAATCACA       300

GGGGTGGTGC ATGAAGCCCT GAAGAAAATT AAAGACGGGC TCTTACGCTT CCGCGTAGGC       360

GGTGACATGC GTTTTTCGAG ATTTTTCTCA TCGAACTACG GCTGCAGATT CGTCGCGAGC       420

GTGCGTACGA ACACTACAGT TTGGCTAAAT TGCACGAAAG CGAGTGGTGA GAAATTCTCA       480

CTCGCCGCCG CGTGCACGGC GGATTACGTG GCGATGCTGC GTTATGTGTG TGGCGGGAAA       540

TTTCCACTCG TCCTCATGAG TAGAGTTATT TACCCGGATG GGCGCTGTTA CTTGGCCCAT       600

ATGAGGTATT TGTGCGCCTT TTACTGTCGC CCGTTTAGAG AGTCGGATTA TGCCCTCGGA       660

ATGTGGCCTA CGGTGGCGCG TCTCAGGGCA TGCGTTGAGA AGAACTTCGG TGTCGAAGCT       720

TGTGGCATAG CTCTTCGTGG CTATTACACC TCTCGCAATG TTTATCACTG TGATTATGAC       780

TCTGCTTATG TAAAATATTT TAGAAACCTT TCCGGCCGCA TTGGCGGTGG TTCGTTCGAT       840

CCGACATCTT TAACCTCCGT AATAACGGTG AAGATTAGCG GTCTTCCAGG TGGTCTTCCT       900

AAAAATATAG CGTTTGGTGC CTTCCTGTGC GATATACGTT ACGTCGAACC GGTAGACTCG       960

GGCGGCATTC AATCGAGCGT TAAGACGAAA CGTGAAGATG CGCACCGAAC CGTAGAGGAA      1020

CGGGCGGCCG GCGGATCCGT CGAGCAACCG CGACAAAAGA GGATAGATGA GAAAGGTTGC      1080

GGCAGAGTTC CTAGTGGAGG TTTTTCGCAT CTCCTGGTCG GCAACCTTAA CGAAGTTAGG      1140

AGGAAGGTAG CTGCCGGACT TCTACGCTTT CGCGTTGGCG GTGATATGGA TTTTCATCGC      1200

TCGTTCTCCA CCCAAGCGGG CCACCGCTTG CTGGTGTGGC GCCGCTCGAG CCGGAGCGTG      1260

TGCCTTGAAC TTTACTCACC ATCTAAAAAC TTTTTGCGTT ACGATGTCTT GCCCTGTTCT      1320

GGAGACTATG CAGCGATGTT TTCTTTCGCG GCGGGCGGCC GTTTCCCTTT AGTTTTGATG      1380

ACTAGAATTA GATACCCGAA CGGGTTTTGT TACTTGGCTC ACTGCCGGTA CGCGTGCGCG      1440
```

-continued

```
TTTCTCTTAA GGGGTTTTGA TCCGAAGCGT TTCGACATCG GTGCTTTCCC CACCGCGGCC    1500

AAGCTCAGAA ACCGTATGGT TTCGGAGCTT GGTGAAAGAA GTTTAGGTTT GAACTTGTAC    1560

GGCGCATATA CGTCACGCGG CGTCTTTCAC TGCGATTATG ACGCTAAGTT TATAAAGGAT    1620

TTGCGTCTTA TGTCAGCAGT TATAGCTGGA AAGGACGGGG TGGAAGAGGT GGTACCTTCT    1680

GACATAACTC CTGCCATGAA GCAGAAAACG ATCAAGCCG  TGTATGATAG ATTATATGGC    1740

GGCACTGACT CGTTGCTGAA ACTGAGCATC GAGAAAGACT TAATCGATTT CAAAAATGAC    1800

GTGCAGAGTT TGAAGAAAGA TCGGCCGATT GTCAAAGTGC CCTTTTACAT GTCGGAAGCA    1860

ACACAGAATT CGCTGACGCG TTTCTACCCT CAGTTCGAAC TTAAGTTTTC GCACTCCTCG    1920

CATTCAGATC ATCCCGCCGC CGCCGCTTCT AGACTGCTGG AAAATGAAAC GTTAGTGCGC    1980

TTATGTGGTA ATAGCGTTTC AGATATTGGA GGTTGTCCTC TTTTCCATTT GCATTCCAAG    2040

ACGCAAAGAC GGGTTCACGT ATGTAGGCCT GTGTTGGATG GCAAGGATGC GCAGCGTCGC    2100

GTGGTGCGTG ATTTGCAGTA TTCCAACGTG CGTTTGGGAG ACGATGATAA AATTTTGGAA    2160

GGGCCACGCA ATATCGACAT TTGCCACTAT CCTCTGGGCG CGTGTGACCA CGAAAGTAGT    2220

GCTATGATGA TGGTGCAGGT GTATGACGCG TCCCTTTATG AGATATGTGG CGCCATGATC    2280

AAGAAGAAAA GCCGCATAAC GTACTTAACC ATGGTCACGC CCGGCGAGTT TCTTGACGGA    2340

CGCGAATGCG TCTACATGGA GTCGTTAGAC TGTGAGATTG AAGTTGATGT GCACGCGGAC    2400

GTCGTAATGT ACAAATTCGG TAGTTCTTGC TATTCGCACA AGCTTTCAAT CATCAAGGAC    2460

ATCATGACCA CTCCGTACTT GACACTAGGT GGTTTTCTAT TCAGCGTGGA GATGTATGAG    2520

GTGCGTATGG GCGTGAATTA CTTCAAGATT ACGAAGTCCG AAGTATCGCC TAGCATTAGC    2580

TGCACCAAGC TCCTGAGATA CCGAAGAGCT AATAGTGACG TGGTTAAAGT TAAACTTCCA    2640

CGTTTCGATA AGAAACGTCG CATGTGTCTG CCTGGGTATG ACACCATATA CCTAGATTCG    2700

AAGTTTGTGA GTCGCGTTTT CGATTATGTC GTGTGTAATT GCTCTGCCGT GAACTCAAAA    2760

ACTTTCGAGT GGGTGTGGAG TTTCATTAAG TCTAGTAAGT CGAGGGTGAT TATTAGCGGT    2820

AAAATAATTC ACAAGGATGT GAATTTGGAC CTCAAGTACG TCGAGAGTTT CGCCGCGGTT    2880

ATGTTGGCCT CTGGCGTGCG CAGTAGACTA GCGTCCGAGT ACCTTGCTAA GAACCTTAGT    2940

CATTTTTCGG GAGATTGCTC CTTTATTGAA GCCACGTCTT TCGTGTTGCG TGAGAAAATC    3000

AGAAACATGA CTCTGAATTT TAACGAAAGA CTTTTACAGT TAGTGAAGCG CGTTGCCTTT    3060

GCGACCTTGG ACGTGAGTTT TCTAGATTTA GATTCAACTC TTGAATCAAT AACTGATTTT    3120

GCCGAGTGTA AGGTAGCGAT TGAACTCGAC GAGTTGGGTT GCTTGAGAGC GGAGGCCGAG    3180

AATGAAAAAA TCAGGAATCT GGCGGGAGAT TCGATTGCGG CTAAACTCGC GAGCGAGATA    3240

GTGGTCGATA TTGACTCTAA GCCTTCACCG AAGCAGGTGG GTAATTCGTC ATCCGAAAAC    3300

GCCGATAAGC GGGAAGTTCA GAGGCCCGGT TTGCGTGGTG GTTCTAGAAA CGGGGTTGTT    3360

GGGGAGTTCC TTCACTTCGT CGTGGATTCT GCCTTGCGTC TTTTCAAATA CGCGACGGAT    3420

CAACAACGGA TCAAGTCTTA CGTGCGTTTC TTGGACTCGG CGGTCTCATT CTTGGATTAC    3480

AACTACGATA ATCTATCGTT TATACTGCGA GTGCTTTCGG AAGGTTATTC GTGTATGTTC    3540

GCGTTTTTGG CGAATCGCGG CGACTTATCT AGTCGTGTCC GTAGCGCGGT GTGTGCTGTG    3600

AAAGAAGTTG CTACCTCATG CGCGAACGCG AGCGTTTCTA AAGCCAAGGT TATGATTACC    3660

TTCGCAGCGG CCGTGTGTGC TATGATGTTT AATAGCTGCG GTTTTCAGG  CGACGGTCGG    3720

GAGTATAAAT CGTATATACA TCGTTACACG CAAGTATTGT TTGACACTAT CTTTTTTGAG    3780

GACAGCAGTT ACCTACCCAT AGAAGTTCTG AGTTCGGCGA TATGCGGTGC TATCGTCACA    3840
```

-continued

```
CTTTTCTCCT CGGGCTCGTC CATAAGTTTA AACGCCTTCT TACTTCAAAT TACCAAAGGA    3900

TTCTCCCTAG AGGTTGTCGT CCGGAATGTT GTGCGAGTCA CGCATGGTTT GAGCACCACA    3960

GCGACCGACG GCGTCATACG TGGGGTTTTC TCCCAAATTG TGTCTCACTT ACTTGTTGGA    4020

AATACGGGTA ATGTGGCTTA CCAGTCAGCT TTCATTGCCG GGGTGGTGCC TCTTTTAGTT    4080

AAAAAGTGTG TGAGCTTAAT CTTCATCTTG CGTGAAGATA CTTATTCCGG TTTTATTAAG    4140

CACGGAATCA GTGAATTCTC TTTCCTTAGT AGTATTCTGA AGTTCTTGAA GGGTAAGCTT    4200

GTGGACGAGT TGAAATCGAT TATTCAAGGG GTTTTTGATT CCAACAAGCA CGTGTTTAAA    4260

GAAGCTACTC AGGAAGCGAT TCGTACGACG GTCATGCAAG TGCCTGTCGC TGTAGTGGAT    4320

GCCCTTAAGA GCGCCGCGGG AAAAATTTAT AACAATTTTA CTAGTCGACG TACCTTTGGT    4380

AAGGATGAAG CTCCTCTAG CGACGGCGCA TGTGAAGAGT ATTTCTCATG CGACGAAGGT     4440

GAAGGTCCGG GTCTGAAAGG GGGTTCCAGC TATGGCTTCT CAATTTTAGC GTTCTTTTCA    4500

CGCATTATGT GGGGAGCTCG TCGGCTTATT GTTAAGGTGA AGCATGAGTG TTTTGGGAAA    4560

CTTTTTGAAT TTCTATCGCT CAAGCTTCAC GAATTCAGGA CTCGCGTTTT TGGGAAGAAT    4620

AGAACGGACG TGGGAGTTTA CGATTTTTTG CCCACGGGCA TCGTGGAAAC GCTCTCATCG    4680

ATAGAAGAGT GCGACCAAAT TGAAGAACTT CTCGGCGACG ACCTGAAAGG TGACAAGGAT    4740

GCTTCGTTGA CCGATATGAA TTACTTTGAG TTCTCAGAAG ACTTCTTAGC CTCTATCGAG    4800

GAGCCGCCTT TCGCTGGATT GCGAGGAGGT AGCAAGAACA TCGCGATTTT GGCGATTTTG    4860

GAATACGCGC ATAATTTGTT TCGCATTGTC GCAAGCAAGT GTTCGAAACG ACCTTTATTT    4920

CTTGCTTTCG CCGAACTCTC AAGCGCCCTT ATCGAGAAAT TTAAGGAGGT TTTCCCTCGT    4980

AAGAGCCAGC TCGTCGCTAT CGTGCGCGAG TATACTCAGA GATTCCTCCG AAGTCGCATG    5040

CGTGCGTTGG GTTTGAATAA CGAGTTCGTG GTAAAATCTT TCGCCGATTT GCTACCCGCA    5100

TTAATGAAGC GGAAGGTTTC AGGTTCGTTC TTAGCTAGTG TTTATCGCCC ACTTAGAGGT    5160

TTCTCATATA TGTGTGTTTC AGCGGAGCGA CGTGAAAAGT TTTTTGCTCT CGTGTGTTTA    5220

ATCGGGTTAA GTCTCCCTTT CTTCGTGCGC ATCGTAGGAG CGAAAGCGTG CGAAGAACTC    5280

GTGTCCTCAG CGCGTCGCTT TTATGAGCGT ATTAAAATTT TTCTAAGGCA GAAGTATGTC    5340

TCTCTTTCTA ATTTCTTTTG TCACTTGTTT AGCTCTGACG TTGATGACAG TTCCGCATCT    5400

GCAGGGTTGA AAGGTGGTGC GTCGCGAATG ACGCTCTTCC ACCTTCTGGT TCGCCTTGCT    5460

AGTGCCCTCC TATCGTTAGG GTGGGAAGGG TTAAAGCTAC TCTTATCGCA CCACAACTTG    5520

TTATTTTGT GTTTTGCATT GGTTGACGAT GTGAACGTCC TTATCAAAGT TCTTGGGGGT     5580

CTTTCTTTCT TTGTGCAACC AATCTTTTCC TTGTTTGCGG CGATGCTTCT ACAACCGGAC    5640

AGGTTTGTGG AGTATTCCGA GAAACTTGTT ACAGCGTTTG AATTTTTCTT AAAATGTTCG    5700

CCTCGCGCGC CTGCACTACT CAAAGGGTTT TTTGAGTGCG TGGCGAACAG CACTGTGTCA    5760

AAAACCGTTC GAAGACTTCT TCGCTGTTTC GTGAAGATGC TCAAACTTCG AAAAGGGCGA    5820

GGGTTGCGTG CGGATGGTAG GGGTCTCCAT CGGCAGAAAG CCGTACCCGT CATACCTTCT    5880

AATCGGGTCG TGACCGACGG GGTTGAAAGA CTTTCGGTAA AGATGCAAGG AGTTGAAGCG    5940

TTGCGTACCG AATTGAGAAT CTTAGAAGAT TTAGATTCTG CCGTGATCGA AAACTCAATA    6000

AGACGCAGAA ATCGTGACAC TAATGACGAC GAATTTACGC GCCCTGCTCA TGAGCAGATG    6060

CAAGAAGTCA CCACTTTCTG TTCGAAAGCC AACTCTGCTG GTTGGCCCT GGAAAGGGCA     6120

GTGCTTGTGG AAGACGCTAT AAAGTCGGAG AAACTTTCTA AGACGGTTAA TGAGATGGTG    6180
```

-continued

```
AGGAAAGGGA GTACCACCAG CGAAGAAGTG GCCGTCGCTT TGTCGGACGA TGAAGCCGTG  6240

GAAGAAATCT CTGTTGCTGA CGAGCGAGAC GATTCGCCTA AGACAGTCAG GATAAGCGAA  6300

TACCTAAATA GGTTAAACTC AAGCTTCGAA TTCCCGAAGC CTATTGTTGT GGACGACAAC  6360

AAGGATACCG GGGGTCTAAC GAACGCCGTG AGGGAGTTTT ATTATATGCA AGAACTTGCT  6420

CTTTTCGAAA TCCACAGCAA ACTGTGCACC TACTACGATC AACTGCGCAT AGTCAACTTC  6480

GATCGTTCCG TAGCACCATG CAGCGAAGAT GCTCAGCTGT ACGTACGGAA GAACGGCTCA  6540

ACGATAGTGC AGGGTAAAGA GGTACGTTTG CACATTAAGG ATTTCCACGA TCACGATTTC  6600

CTGTTTGACG GAAAAATTTC TATTAACAAG CGGCGGCGAG GCGGAAATGT TTTATATCAC  6660

GACAACCTCG CGTTCTTGGC GAGTAATTTG TTCTTAGCCG GCTACCCCTT TTCAAGGAGC  6720

TTCGTCTTCA CGAATTCGTC GGTCGATATT CTCCTCTACG AAGCTCCACC CGGAGGTGGT  6780

AAGACGACGA CGCTGATTGA CTCGTTCTTG AAGGTCTTCA AGAAAGGTGA GGTTTCCACC  6840

ATGATCTTAA CCGCCAACAA AAGTTCGCAG GTTGAGATCC TAAAGAAAGT GGAGAAGGAA  6900

GTGTCTAACA TTGAATGCCA GAAACGTAAA GACAAAAGAT CTCCGAAAAA GAGCATTTAC  6960

ACCATCGACG CTTATTTAAT GCATCACCGT GGTTGTGATG CAGACGTTCT TTTCATCGAT  7020

GAGTGTTTCA TGGTTCATGC GGGTAGCGTA CTAGCTTGCA TTGAGTTCAC GAGGTGTCAT  7080

AAAGTAATGA TCTTCGGGGA TAGCCGGCAG ATTCACTACA TTGAAAGGAA CGAATTGGAC  7140

AAGTGTTTGT ATGGGGATCT CGACAGGTTC GTGGACCTGC AGTGTCGGGT TTATGGTAAT  7200

ATTTCGTACC GTTGTCCATG GGATGTGTGC GCTTGGTTAA GCACAGTGTA TGGCAACCTA  7260

ATCGCCACCG TGAAGGGTGA AAGCGAAGGT AAGAGCAGCA TGCGCATTAA CGAAATTAAT  7320

TCAGTCGACG ATTTAGTCCC CGACGTGGGT TCCACGTTTC TGTGTATGCT TCAGTCGGAG  7380

AAGTTGGAAA TCAGCAAGCA CTTTATTCGC AAGGGTTTGA CTAAACTTAA CGTTCTAACG  7440

GTGCATGAGG CGCAAGGTGA GACGTATGCG CGTGTGAACC TTGTGCGACT TAAGTTTCAG  7500

GAGGATGAAC CCTTTAAATC TATCAGGCAC ATAACCGTCG CTCTTTCTCG TCACACCGAC  7560

AGCTTAACTT ATAACGTCTT AGCTGCTCGT CGAGGTGACG CCACTTGCGA TGCCATCCAG  7620

AAGGCTGCGG AATTGGTGAA CAAGTTTCGC GTTTTTCCTA CATCTTTTGG TGGTAGTGTT  7680

ATCAATCTCA ACGTGAAGAA GGACGTGGAA GATAACAGTA GGTGCAAGGC TTCGTCGGCA  7740

CCATTGAGCG TAATCAACGA CTTTTTGAAC GAAGTTAATC CCGGTACTGC GGTGATTGAT  7800

TTTGGTGATT TGTCCGCGGA CTTCAGTACT GGGCCTTTTG AGTGCGGTGC CAGCGGTATT  7860

GTGGTGCGGG ACAACATCTC CTCCAGCAAC ATCACTGATC ACGATAAGCA GCGTGTTTAG  7920
```

(2) INFORMATION FOR SEQ ID NO:3:

(i) SEQUENCE CHARACTERISTICS:
        (A) LENGTH: 2639 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Thr Leu Arg Glu Asn Pro Ile Ser Val Ser Gly Val Asn Leu Gly Arg
1               5                   10                  15

Ser Ala Ala Ala Gln Val Ile Tyr Phe Gly Ser Phe Thr Gln Pro Phe
                20                  25                  30

Ala Leu Tyr Pro Arg Gln Glu Ser Ala Ile Val Lys Thr Gln Leu Pro
            35                  40                  45
```

```
Pro Val Ser Val Val Lys Val Glu Cys Val Ala Ala Glu Val Ala Pro
 50                  55                  60

Asp Arg Gly Val Val Asp Lys Lys Pro Thr Ser Val Gly Val Pro Pro
 65                  70                  75                  80

Gln Arg Gly Val Leu Ser Phe Pro Thr Val Val Arg Asn Arg Gly Asp
                 85                  90                  95

Val Ile Ile Thr Gly Val Val His Glu Ala Leu Lys Lys Ile Lys Asp
            100                 105                 110

Gly Leu Leu Arg Phe Arg Val Gly Gly Asp Met Arg Phe Ser Arg Phe
            115                 120                 125

Phe Ser Ser Asn Tyr Gly Cys Arg Phe Val Ala Ser Val Arg Thr Asn
130                 135                 140

Thr Thr Val Trp Leu Asn Cys Thr Lys Ala Ser Gly Glu Lys Phe Ser
145                 150                 155                 160

Leu Ala Ala Ala Cys Thr Ala Asp Tyr Val Ala Met Leu Arg Tyr Val
                165                 170                 175

Cys Gly Gly Lys Phe Pro Leu Val Leu Met Ser Arg Val Ile Tyr Pro
            180                 185                 190

Asp Gly Arg Cys Tyr Leu Ala His Met Arg Tyr Leu Cys Ala Phe Tyr
            195                 200                 205

Cys Arg Pro Phe Arg Glu Ser Asp Tyr Ala Leu Gly Met Trp Pro Thr
210                 215                 220

Val Ala Arg Leu Arg Ala Cys Val Glu Lys Asn Phe Gly Val Glu Ala
225                 230                 235                 240

Cys Gly Ile Ala Leu Arg Gly Tyr Tyr Thr Ser Arg Asn Val Tyr His
                245                 250                 255

Cys Asp Tyr Asp Ser Ala Tyr Val Lys Tyr Phe Arg Asn Leu Ser Gly
            260                 265                 270

Arg Ile Gly Gly Ser Phe Asp Pro Thr Ser Leu Thr Ser Val Ile
            275                 280                 285

Thr Val Lys Ile Ser Gly Leu Pro Gly Gly Leu Pro Lys Asn Ile Ala
290                 295                 300

Phe Gly Ala Phe Leu Cys Asp Ile Arg Tyr Val Glu Pro Val Asp Ser
305                 310                 315                 320

Gly Gly Ile Gln Ser Ser Val Lys Thr Lys Arg Glu Asp Ala His Arg
                325                 330                 335

Thr Val Glu Glu Arg Ala Ala Gly Gly Ser Val Glu Gln Pro Arg Gln
            340                 345                 350

Lys Arg Ile Asp Glu Lys Gly Cys Gly Arg Val Pro Ser Gly Gly Phe
            355                 360                 365

Ser His Leu Leu Val Gly Asn Leu Asn Glu Val Arg Arg Lys Val Ala
370                 375                 380

Ala Gly Leu Leu Arg Phe Arg Val Gly Gly Asp Met Asp Phe His Arg
385                 390                 395                 400

Ser Phe Ser Thr Gln Ala Gly His Arg Leu Leu Val Trp Arg Arg Ser
                405                 410                 415

Ser Arg Ser Val Cys Leu Glu Leu Tyr Ser Pro Ser Lys Asn Phe Leu
            420                 425                 430

Arg Tyr Asp Val Leu Pro Cys Ser Gly Asp Tyr Ala Ala Met Phe Ser
            435                 440                 445

Phe Ala Ala Gly Gly Arg Phe Pro Leu Val Leu Met Thr Arg Ile Arg
450                 455                 460
```

```
Tyr Pro Asn Gly Phe Cys Tyr Leu Ala His Cys Arg Tyr Ala Cys Ala
465                 470                 475                 480

Phe Leu Leu Arg Gly Phe Asp Pro Lys Arg Phe Asp Ile Gly Ala Phe
            485                 490                 495

Pro Thr Ala Ala Lys Leu Arg Asn Arg Met Val Ser Glu Leu Gly Glu
            500                 505                 510

Arg Ser Leu Gly Leu Asn Leu Tyr Gly Ala Tyr Thr Ser Arg Gly Val
            515                 520                 525

Phe His Cys Asp Tyr Asp Ala Lys Phe Ile Lys Asp Leu Arg Leu Met
            530                 535                 540

Ser Ala Val Ile Ala Gly Lys Asp Gly Val Glu Glu Val Val Pro Ser
545                 550                 555                 560

Asp Ile Thr Pro Ala Met Lys Gln Lys Thr Ile Glu Ala Val Tyr Asp
                565                 570                 575

Arg Leu Tyr Gly Gly Thr Asp Ser Leu Leu Lys Leu Ser Ile Glu Lys
            580                 585                 590

Asp Leu Ile Asp Phe Lys Asn Asp Val Gln Ser Leu Lys Lys Asp Arg
            595                 600                 605

Pro Ile Val Lys Val Pro Phe Tyr Met Ser Glu Ala Thr Gln Asn Ser
            610                 615                 620

Leu Thr Arg Phe Tyr Pro Gln Phe Glu Leu Lys Phe Ser His Ser Ser
625                 630                 635                 640

His Ser Asp His Pro Ala Ala Ala Ser Arg Leu Leu Glu Asn Glu
                645                 650                 655

Thr Leu Val Arg Leu Cys Gly Asn Ser Val Ser Asp Ile Gly Gly Cys
            660                 665                 670

Pro Leu Phe His Leu His Ser Lys Thr Gln Arg Arg Val His Val Cys
            675                 680                 685

Arg Pro Val Leu Asp Gly Lys Asp Ala Gln Arg Val Val Arg Asp
690                 695                 700

Leu Gln Tyr Ser Asn Val Arg Leu Gly Asp Asp Lys Ile Leu Glu
705                 710                 715                 720

Gly Pro Arg Asn Ile Asp Ile Cys His Tyr Pro Leu Gly Ala Cys Asp
                725                 730                 735

His Glu Ser Ser Ala Met Met Met Val Gln Val Tyr Asp Ala Ser Leu
            740                 745                 750

Tyr Glu Ile Cys Gly Ala Met Ile Lys Lys Lys Ser Arg Ile Thr Tyr
            755                 760                 765

Leu Thr Met Val Thr Pro Gly Glu Phe Leu Asp Gly Arg Glu Cys Val
770                 775                 780

Tyr Met Glu Ser Leu Asp Cys Glu Ile Glu Val Asp Val His Ala Asp
785                 790                 795                 800

Val Val Met Tyr Lys Phe Gly Ser Ser Cys Tyr Ser His Lys Leu Ser
                805                 810                 815

Ile Ile Lys Asp Ile Met Thr Thr Pro Tyr Leu Thr Leu Gly Gly Phe
            820                 825                 830

Leu Phe Ser Val Glu Met Tyr Glu Val Arg Met Gly Val Asn Tyr Phe
            835                 840                 845

Lys Ile Thr Lys Ser Glu Val Ser Pro Ser Ile Ser Cys Thr Lys Leu
            850                 855                 860

Leu Arg Tyr Arg Arg Ala Asn Ser Asp Val Val Lys Val Lys Leu Pro
865                 870                 875                 880

Arg Phe Asp Lys Lys Arg Arg Met Cys Leu Pro Gly Tyr Asp Thr Ile
```

-continued

```
                885                 890                 895
Tyr Leu Asp Ser Lys Phe Val Ser Arg Val Phe Asp Tyr Val Cys
                900                 905                 910
Asn Cys Ser Ala Val Asn Ser Lys Thr Phe Glu Trp Val Trp Ser Phe
                915                 920                 925
Ile Lys Ser Ser Lys Ser Arg Val Ile Ile Ser Gly Lys Ile Ile His
                930                 935                 940
Lys Asp Val Asn Leu Asp Leu Lys Tyr Val Glu Ser Phe Ala Ala Val
945                 950                 955                 960
Met Leu Ala Ser Gly Val Arg Ser Arg Leu Ala Ser Glu Tyr Leu Ala
                965                 970                 975
Lys Asn Leu Ser His Phe Ser Gly Asp Cys Ser Phe Ile Glu Ala Thr
                980                 985                 990
Ser Phe Val Leu Arg Glu Lys Ile Arg Asn Met Thr Leu Asn Phe Asn
                995                 1000                1005
Glu Arg Leu Leu Gln Leu Val Lys Arg Val Ala Phe Ala Thr Leu Asp
                1010                1015                1020
Val Ser Phe Leu Asp Leu Asp Ser Thr Leu Glu Ser Ile Thr Asp Phe
1025                1030                1035                1040
Ala Glu Cys Lys Val Ala Ile Glu Leu Asp Glu Leu Gly Cys Leu Arg
                1045                1050                1055
Ala Glu Ala Glu Asn Glu Lys Ile Arg Asn Leu Ala Gly Asp Ser Ile
                1060                1065                1070
Ala Ala Lys Leu Ala Ser Glu Ile Val Asp Ile Asp Ser Lys Pro
                1075                1080                1085
Ser Pro Lys Gln Val Gly Asn Ser Ser Glu Asn Ala Asp Lys Arg
                1090                1095                1100
Glu Val Gln Arg Pro Gly Leu Arg Gly Gly Ser Arg Asn Gly Val Val
1105                1110                1115                1120
Gly Glu Phe Leu His Phe Val Val Asp Ser Ala Leu Arg Leu Phe Lys
                1125                1130                1135
Tyr Ala Thr Asp Gln Gln Arg Ile Lys Ser Tyr Val Arg Phe Leu Asp
                1140                1145                1150
Ser Ala Val Ser Phe Leu Asp Tyr Asn Tyr Asp Asn Leu Ser Phe Ile
                1155                1160                1165
Leu Arg Val Leu Ser Glu Gly Tyr Ser Cys Met Phe Ala Phe Leu Ala
                1170                1175                1180
Asn Arg Gly Asp Leu Ser Ser Arg Val Arg Ser Ala Val Cys Ala Val
1185                1190                1195                1200
Lys Glu Val Ala Thr Ser Cys Ala Asn Ala Ser Val Ser Lys Ala Lys
                1205                1210                1215
Val Met Ile Thr Phe Ala Ala Val Cys Ala Met Met Phe Asn Ser
                1220                1225                1230
Cys Gly Phe Ser Gly Asp Gly Arg Glu Tyr Lys Ser Tyr Ile His Arg
                1235                1240                1245
Tyr Thr Gln Val Leu Phe Asp Thr Ile Phe Phe Glu Asp Ser Ser Tyr
                1250                1255                1260
Leu Pro Ile Glu Val Leu Ser Ser Ala Ile Cys Gly Ala Ile Val Thr
1265                1270                1275                1280
Leu Phe Ser Ser Gly Ser Ser Ile Ser Leu Asn Ala Phe Leu Leu Gln
                1285                1290                1295
Ile Thr Lys Gly Phe Ser Leu Glu Val Val Val Arg Asn Val Val Arg
                1300                1305                1310
```

-continued

```
Val Thr His Gly Leu Ser Thr Thr Ala Thr Asp Gly Val Ile Arg Gly
        1315             1320             1325

Val Phe Ser Gln Ile Val Ser His Leu Leu Val Gly Asn Thr Gly Asn
        1330             1335             1340

Val Ala Tyr Gln Ser Ala Phe Ile Ala Gly Val Val Pro Leu Leu Val
1345             1350             1355             1360

Lys Lys Cys Val Ser Leu Ile Phe Ile Leu Arg Glu Asp Thr Tyr Ser
            1365             1370             1375

Gly Phe Ile Lys His Gly Ile Ser Glu Phe Ser Phe Leu Ser Ser Ile
            1380             1385             1390

Leu Lys Phe Leu Lys Gly Lys Leu Val Asp Glu Leu Lys Ser Ile Ile
        1395             1400             1405

Gln Gly Val Phe Asp Ser Asn Lys His Val Phe Lys Glu Ala Thr Gln
    1410             1415             1420

Glu Ala Ile Arg Thr Thr Val Met Gln Val Pro Val Ala Val Val Asp
1425             1430             1435             1440

Ala Leu Lys Ser Ala Ala Gly Lys Ile Tyr Asn Asn Phe Thr Ser Arg
            1445             1450             1455

Arg Thr Phe Gly Lys Asp Glu Gly Ser Ser Ser Asp Gly Ala Cys Glu
            1460             1465             1470

Glu Tyr Phe Ser Cys Asp Glu Gly Glu Gly Pro Gly Leu Lys Gly Gly
        1475             1480             1485

Ser Ser Tyr Gly Phe Ser Ile Leu Ala Phe Phe Ser Arg Ile Met Trp
        1490             1495             1500

Gly Ala Arg Arg Leu Ile Val Lys Val Lys His Glu Cys Phe Gly Lys
1505             1510             1515             1520

Leu Phe Glu Phe Leu Ser Leu Lys Leu His Glu Phe Arg Thr Arg Val
            1525             1530             1535

Phe Gly Lys Asn Arg Thr Asp Val Gly Val Tyr Asp Phe Leu Pro Thr
            1540             1545             1550

Gly Ile Val Glu Thr Leu Ser Ser Ile Glu Glu Cys Asp Gln Ile Glu
        1555             1560             1565

Glu Leu Leu Gly Asp Asp Leu Lys Gly Asp Lys Asp Ala Ser Leu Thr
1570             1575             1580

Asp Met Asn Tyr Phe Glu Phe Ser Glu Asp Phe Leu Ala Ser Ile Glu
1585             1590             1595             1600

Glu Pro Pro Phe Ala Gly Leu Arg Gly Gly Ser Lys Asn Ile Ala Ile
            1605             1610             1615

Leu Ala Ile Leu Glu Tyr Ala His Asn Leu Phe Arg Ile Val Ala Ser
            1620             1625             1630

Lys Cys Ser Lys Arg Pro Leu Phe Leu Ala Phe Ala Glu Leu Ser Ser
            1635             1640             1645

Ala Leu Ile Glu Lys Phe Lys Glu Val Phe Pro Arg Lys Ser Gln Leu
        1650             1655             1660

Val Ala Ile Val Arg Glu Tyr Thr Gln Arg Phe Leu Arg Ser Arg Met
1665             1670             1675             1680

Arg Ala Leu Gly Leu Asn Asn Glu Phe Val Val Lys Ser Phe Ala Asp
            1685             1690             1695

Leu Leu Pro Ala Leu Met Lys Arg Lys Val Ser Gly Ser Phe Leu Ala
            1700             1705             1710

Ser Val Tyr Arg Pro Leu Arg Gly Phe Ser Tyr Met Cys Val Ser Ala
        1715             1720             1725
```

-continued

Glu Arg Arg Glu Lys Phe Phe Ala Leu Val Cys Leu Ile Gly Leu Ser
         1730                1735                1740

Leu Pro Phe Phe Val Arg Ile Val Gly Ala Lys Ala Cys Glu Glu Leu
1745                1750                1755                1760

Val Ser Ser Ala Arg Arg Phe Tyr Glu Arg Ile Lys Ile Phe Leu Arg
                1765                1770                1775

Gln Lys Tyr Val Ser Leu Ser Asn Phe Phe Cys His Leu Phe Ser Ser
            1780                1785                1790

Asp Val Asp Asp Ser Ser Ala Ser Ala Gly Leu Lys Gly Gly Ala Ser
            1795                1800                1805

Arg Met Thr Leu Phe His Leu Leu Val Arg Leu Ala Ser Ala Leu Leu
        1810                1815                1820

Ser Leu Gly Trp Glu Gly Leu Lys Leu Leu Leu Ser His His Asn Leu
1825                1830                1835                1840

Leu Phe Leu Cys Phe Ala Leu Val Asp Asp Val Asn Val Leu Ile Lys
                1845                1850                1855

Val Leu Gly Gly Leu Ser Phe Phe Val Gln Pro Ile Phe Ser Leu Phe
            1860                1865                1870

Ala Ala Met Leu Leu Gln Pro Asp Arg Phe Val Glu Tyr Ser Glu Lys
            1875                1880                1885

Leu Val Thr Ala Phe Glu Phe Phe Leu Lys Cys Ser Pro Arg Ala Pro
        1890                1895                1900

Ala Leu Leu Lys Gly Phe Phe Glu Cys Val Ala Asn Ser Thr Val Ser
1905                1910                1915                1920

Lys Thr Val Arg Arg Leu Leu Arg Cys Phe Val Lys Met Leu Lys Leu
                1925                1930                1935

Arg Lys Gly Arg Gly Leu Arg Ala Asp Gly Arg Gly Leu His Arg Gln
            1940                1945                1950

Lys Ala Val Pro Val Ile Pro Ser Asn Arg Val Val Thr Asp Gly Val
            1955                1960                1965

Glu Arg Leu Ser Val Lys Met Gln Gly Val Glu Ala Leu Arg Thr Glu
    1970                1975                1980

Leu Arg Ile Leu Glu Asp Leu Asp Ser Ala Val Ile Glu Lys Leu Asn
1985                1990                1995                2000

Arg Arg Arg Asn Arg Asp Thr Asn Asp Asp Glu Phe Thr Arg Pro Ala
                2005                2010                2015

His Glu Gln Met Gln Glu Val Thr Thr Phe Cys Ser Lys Ala Asn Ser
            2020                2025                2030

Ala Gly Leu Ala Leu Glu Arg Ala Val Leu Val Glu Asp Ala Ile Lys
        2035                2040                2045

Ser Glu Lys Leu Ser Lys Thr Val Asn Glu Met Val Arg Lys Gly Ser
    2050                2055                2060

Thr Thr Ser Glu Glu Val Ala Val Ala Leu Ser Asp Asp Glu Ala Val
2065                2070                2075                2080

Glu Glu Ile Ser Val Ala Asp Glu Arg Asp Asp Ser Pro Lys Thr Val
            2085                2090                2095

Arg Ile Ser Glu Tyr Leu Asn Arg Leu Asn Ser Ser Phe Glu Phe Pro
            2100                2105                2110

Lys Pro Ile Val Val Asp Asp Asn Lys Asp Thr Gly Gly Leu Thr Asn
            2115                2120                2125

Ala Val Arg Glu Phe Tyr Tyr Met Gln Glu Leu Ala Leu Phe Glu Ile
        2130                2135                2140

His Ser Lys Leu Cys Thr Tyr Tyr Asp Gln Leu Arg Ile Val Asn Phe

```
                2145                2150                2155                2160
Asp Arg Ser Val Ala Pro Cys Ser Glu Asp Ala Gln Leu Tyr Val Arg
            2165                2170                2175
Lys Asn Gly Ser Thr Ile Val Gln Gly Lys Glu Val Arg Leu His Ile
            2180                2185                2190
Lys Asp Phe His Asp His Asp Phe Leu Phe Asp Gly Lys Ile Ser Ile
            2195                2200                2205
Asn Lys Arg Arg Arg Gly Gly Asn Val Leu Tyr His Asp Asn Leu Ala
            2210                2215                2220
Phe Leu Ala Ser Asn Leu Phe Leu Ala Gly Tyr Pro Phe Ser Arg Ser
2225                2230                2235                2240
Phe Val Phe Thr Asn Ser Ser Val Asp Ile Leu Leu Tyr Glu Ala Pro
            2245                2250                2255
Pro Gly Gly Gly Lys Thr Thr Leu Ile Asp Ser Phe Leu Lys Val
            2260                2265                2270
Phe Lys Lys Gly Glu Val Ser Thr Met Ile Leu Thr Ala Asn Lys Ser
            2275                2280                2285
Ser Gln Val Glu Ile Leu Lys Lys Val Glu Lys Val Ser Asn Ile
            2290                2295                2300
Glu Cys Gln Lys Arg Lys Asp Lys Arg Ser Pro Lys Lys Ser Ile Tyr
2305                2310                2315                2320
Thr Ile Asp Ala Tyr Leu Met His His Arg Gly Cys Asp Ala Asp Val
            2325                2330                2335
Leu Phe Ile Asp Glu Cys Phe Met Val His Ala Gly Ser Val Leu Ala
            2340                2345                2350
Cys Ile Glu Phe Thr Arg Cys His Lys Val Met Ile Phe Gly Asp Ser
            2355                2360                2365
Arg Gln Ile His Tyr Ile Glu Arg Asn Glu Leu Asp Lys Cys Leu Tyr
            2370                2375                2380
Gly Asp Leu Asp Arg Phe Val Asp Leu Gln Cys Arg Val Tyr Gly Asn
2385                2390                2395                2400
Ile Ser Tyr Arg Cys Pro Trp Asp Val Cys Ala Trp Leu Ser Thr Val
            2405                2410                2415
Tyr Gly Asn Leu Ile Ala Thr Val Lys Gly Glu Ser Glu Gly Lys Ser
            2420                2425                2430
Ser Met Arg Ile Asn Glu Ile Asn Ser Val Asp Asp Leu Val Pro Asp
            2435                2440                2445
Val Gly Ser Thr Phe Leu Cys Met Leu Gln Ser Glu Lys Leu Glu Ile
            2450                2455                2460
Ser Lys His Phe Ile Arg Lys Gly Leu Thr Lys Leu Asn Val Leu Thr
2465                2470                2475                2480
Val His Glu Ala Gln Gly Glu Thr Tyr Ala Arg Val Asn Leu Val Arg
            2485                2490                2495
Leu Lys Phe Gln Glu Asp Glu Pro Phe Lys Ser Ile Arg His Ile Thr
            2500                2505                2510
Val Ala Leu Ser Arg His Thr Asp Ser Leu Thr Tyr Asn Val Leu Ala
            2515                2520                2525
Ala Arg Arg Gly Asp Ala Thr Cys Asp Ala Ile Gln Lys Ala Ala Glu
            2530                2535                2540
Leu Val Asn Lys Phe Arg Val Phe Pro Thr Ser Phe Gly Gly Ser Val
2545                2550                2555                2560
Ile Asn Leu Asn Val Lys Lys Asp Val Glu Asp Asn Ser Arg Cys Lys
            2565                2570                2575
```

```
Ala Ser Ser Ala Pro Leu Ser Val Ile Asn Asp Phe Leu Asn Glu Val
            2580                2585                2590

Asn Pro Gly Thr Ala Val Ile Asp Phe Gly Asp Leu Ser Ala Asp Phe
        2595                2600                2605

Ser Thr Gly Pro Phe Glu Cys Gly Ala Ser Gly Ile Val Val Arg Asp
    2610                2615                2620

Asn Ile Ser Ser Ser Asn Ile Thr Asp His Asp Lys Gln Arg Val
2625                2630                2635
```

(2) INFORMATION FOR SEQ ID NO:4:

(i) SEQUENCE CHARACTERISTICS:
        (A) LENGTH: 1380 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AGCGTAGTTC GGTCGCAGGC GATTCCGCGT AGAAAACCTT CTCTACAAGA AAATTTGTAT      60
TCGTTTGAAG CGCGGAATTA TAACTTCTCG ACTTGCGACC GTAACACATC TGCTTCAATG     120
TTCGGAGAGG CTATGGCGAT GAACTGTCTT CGTCGTTGCT TCGACCTAGA TGCCTTTTCG     180
TCCCTGCGTG ATGATGTGAT TAGTATCACA CGTTCAGGCA TCGAACAATG GCTGGAGAAA     240
CGTACTCCTA GTCAGATTAA AGCATTAATG AAGGATGTTG AATCGCCTTT GGAAATTGAC     300
GATGAAATTT GTCGTTTTAA GTTGATGGTG AAGCGTGACG CTAAGGTGAA GTTAGACTCT     360
TCTTGTTTAA CTAAACACAG CGCCGCTCAA AATATCATGT TTCATCGCAA GAGCATTAAT     420
GCTATCTTCT CTCCTATCTT TAATGAGGTG AAAAACCGAA TAATGTGCTG TCTTAAGCCT     480
AACATAAAGT TTTTTACGGA GATGACTAAC AGGGATTTTG CTTCTGTTGT CAGCAACATG     540
CTTGGTGACG ACGATGTGTA CCATATAGGT GAAGTTGATT TCTCAAAGTA CGACAAGTCT     600
CAAGATGCTT TCGTGAAGGC TTTTGAAGAA GTAATGTATA AGGAACTCGG TGTTGATGAA     660
GAGTTGCTGG CTATCTGGAT GTGCGGCGAG CGGTTATCGA TAGCTAACAC TCTCGATGGT     720
CAGTTGTCCT TCACGATCGA GAATCAAAGG AAGTCGGGAG CTTCGAACAC TTGGATTGGT     780
AACTCTCTCG TCACTTTGGG TATTTTAAGT CTTTACTACG ACGTTAGAAA TTTCGAGGCG     840
TTGTACATCT CGGGCGATGA TTCTTTAATT TTTTCTCGCA GCGAGATTTC GAATTATGCC     900
GACGACATAT GCACTGACAT GGGTTTTGAG ACAAAATTTA TGTCCCCAAG TGTCCCGTAC     960
TTTTGTTCTA AATTTGTTGT TATGTGTGGT CATAAGACGT TTTTTGTTCC CGACCCGTAC    1020
AAGCTTTTTG TCAAGTTGGG AGCAGTCAAA GAGGATGTTT CAATGGATTT CCTTTTCGAG    1080
ACTTTTACCT CCTTTAAAGA CTTAACCTCC GATTTTAACG ACGAGCGCTT AATTCAAAAG    1140
CTCGCTGAAC TTGTGGCTTT AAAATATGAG GTTCAAACCG GCAACACCAC CTTGGCGTTA    1200
AGTGTGATAC ATTGTTTGCG TTCGAATTTC CTCTCGTTTA GCAAGTTATA TCCTCGCGTG    1260
AAGGGATGGC AGGTTTTTTA CACGTCGGTT AAGAAAGCGC TTCTCAAGAG TGGGTGTTCT    1320
CTCTTCGACA GTTCATGAC CCCTTTTGGT CAGGCTGTCA TGGTTTGGGA TGATGAGTAG    1380
```

(2) INFORMATION FOR SEQ ID NO:5:

(i) SEQUENCE CHARACTERISTICS:
        (A) LENGTH: 459 amino acids
        (B) TYPE: amino acid
        (C) STRANDEDNESS:

(D) TOPOLOGY: linear (ii) MOLECULE TYPE: protein (xi) SEQUENCE DESCRIPTION: SEQ ID NO:5:

```
Ser Val Val Arg Ser Gln Ala Ile Pro Arg Lys Pro Ser Leu Gln
1               5                   10                  15

Glu Asn Leu Tyr Ser Phe Glu Ala Arg Asn Tyr Asn Phe Ser Thr Cys
                20                  25                  30

Asp Arg Asn Thr Ser Ala Ser Met Phe Gly Glu Ala Met Ala Met Asn
            35                  40                  45

Cys Leu Arg Arg Cys Phe Asp Leu Asp Ala Phe Ser Ser Leu Arg Asp
50                      55                  60

Asp Val Ile Ser Ile Thr Arg Ser Gly Ile Glu Gln Trp Leu Glu Lys
65                  70                  75                  80

Arg Thr Pro Ser Gln Ile Lys Ala Leu Met Lys Asp Val Glu Ser Pro
                85                  90                  95

Leu Glu Ile Asp Asp Glu Ile Cys Arg Phe Lys Leu Met Val Lys Arg
                100                 105                 110

Asp Ala Lys Val Lys Leu Asp Ser Ser Cys Leu Thr Lys His Ser Ala
            115                 120                 125

Ala Gln Asn Ile Met Phe His Arg Lys Ser Ile Asn Ala Ile Phe Ser
130                 135                 140

Pro Ile Phe Asn Glu Val Lys Asn Arg Ile Met Cys Cys Leu Lys Pro
145                 150                 155                 160

Asn Ile Lys Phe Phe Thr Glu Met Thr Asn Arg Asp Phe Ala Ser Val
                165                 170                 175

Val Ser Asn Met Leu Gly Asp Asp Val Tyr His Ile Gly Glu Val
            180                 185                 190

Asp Phe Ser Lys Tyr Asp Lys Ser Gln Asp Ala Phe Val Lys Ala Phe
            195                 200                 205

Glu Glu Val Met Tyr Lys Glu Leu Gly Val Asp Glu Glu Leu Leu Ala
210                 215                 220

Ile Trp Met Cys Gly Glu Arg Leu Ser Ile Ala Asn Thr Leu Asp Gly
225                 230                 235                 240

Gln Leu Ser Phe Thr Ile Glu Asn Gln Arg Lys Ser Gly Ala Ser Asn
                245                 250                 255

Thr Trp Ile Gly Asn Ser Leu Val Thr Leu Gly Ile Leu Ser Leu Tyr
            260                 265                 270

Tyr Asp Val Arg Asn Phe Glu Ala Leu Tyr Ile Ser Gly Asp Asp Ser
            275                 280                 285

Leu Ile Phe Ser Arg Ser Glu Ile Ser Asn Tyr Ala Asp Asp Ile Cys
290                 295                 300

Thr Asp Met Gly Phe Glu Thr Lys Phe Met Ser Pro Ser Val Pro Tyr
305                 310                 315                 320

Phe Cys Ser Lys Phe Val Val Met Cys Gly His Lys Thr Phe Phe Val
                325                 330                 335

Pro Asp Pro Tyr Lys Leu Phe Val Lys Leu Gly Ala Val Lys Glu Asp
                340                 345                 350

Val Ser Met Asp Phe Leu Phe Glu Thr Phe Thr Ser Phe Lys Asp Leu
            355                 360                 365

Thr Ser Asp Phe Asn Asp Glu Arg Leu Ile Gln Lys Leu Ala Glu Leu
370                 375                 380

Val Ala Leu Lys Tyr Glu Val Gln Thr Gly Asn Thr Thr Leu Ala Leu
```

```
385                 390                 395                 400
Ser Val Ile His Cys Leu Arg Ser Asn Phe Leu Ser Phe Ser Lys Leu
            405                 410                 415

Tyr Pro Arg Val Lys Gly Trp Gln Val Phe Tyr Thr Ser Val Lys Lys
            420                 425                 430

Ala Leu Leu Lys Ser Gly Cys Ser Leu Phe Asp Ser Phe Met Thr Pro
            435                 440                 445

Phe Gly Gln Ala Val Met Val Trp Asp Asp Glu
    450                 455
```

(2) INFORMATION FOR SEQ ID NO:6:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
ATGAATCAGG TTTTGCAGTT TGAATGTTTG TTTCTGCTGA ATCTCGCGGT TTTTGCTGTG    60

ACTTTCATTT TCATTCTTCT GGTCTTCCGC GTGATTAAGT CTTTTCGCCA GAAGGGTCAC   120

GAAGCACCTG TTCCCGTTGT TCGTGGCGGG GGTTTTTCAA CCGTAGTGTA G            171
```

(2) INFORMATION FOR SEQ ID NO:7:

(i) SEQUENCE CHARACTERISTICS:
        (A) LENGTH: 56 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Asn Gln Val Leu Gln Phe Glu Cys Leu Phe Leu Leu Asn Leu Ala
1               5                   10                  15

Val Phe Ala Val Thr Phe Ile Phe Ile Leu Leu Val Phe Arg Val Ile
            20                  25                  30

Lys Ser Phe Arg Gln Lys Gly His Glu Ala Pro Val Pro Val Val Arg
            35                  40                  45

Gly Gly Gly Phe Ser Thr Val Val
            50                  55
```

(2) INFORMATION FOR SEQ ID NO:8:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
ATGGTAGTTT TCGGTTTGGA CTTTGGCACC ACATTCTCTA CGGTGTGTGT GTACAAGGAT    60

GGACGAGTTT TTTCATTCAA GCAGAATAAT TCGGCGTACA TCCCCACTTA CCTCTATCTC   120

TTCTCCGATT CTAACCACAT GACTTTTGGT TACGAGGCCG AATCACTGAT GAGTAATCTG   180

AAAGTTAAAG GTTCGTTTTA TAGAGATTTA AAACGTTGGG TGGGTTGCGA TTCGAGTAAC   240
```

-continued

```
CTCGACGCGT ACCTTGACCG TTTAAAACCT CATTACTCGG TCCGCTTGGT TAAGATCGGC      300

TCTGGCTTGA ACGAAACTGT TTCAATTGGA AACTTCGGGG GCACTGTTAA GTCTGAGGCT      360

CATCTGCCAG GGTTGATAGC TCTCTTTATT AAGGCTGTCA TTAGTTGCGC GGAGGGCGCG      420

TTTGCGTGCA CTTGCACCGG GGTTATTTGT TCAGTACCTG CCAATTATGA TAGCGTTCAA      480

AGGAATTTCA CTGATCAGTG TGTTTCACTC AGCGGTTATC AGTGCGTATA TATGATCAAT      540

GAACCTTCAG CGGCTGCGCT ATCTGCGTGT AATTCGATTG GAAAGAAGTC CGCAAATTTG      600

GCTGTTTACG ATTTCGGTGG TGGGACCTTC GACGTGTCTA TCATTTCATA CCGCAACAAT      660

ACTTTTGTTG TGCGAGCTTC TGGAGGCGAT CTAAATCTCG GTGGAAGGGA TGTTGATCGT      720

GCGTTTCTCA CGCACCTCTT CTCTTTAACA TCGCTGGAAC CTGACCTCAC TTTGGATATC      780

TCGAATCTGA AGAATCTTT ATCAAAAACG GACGCAGAGA TAGTTTACAC TTTGAGAGGT      840

GTCGATGGAA GAAAGAAGA CGTTAGAGTA AACAAAAACA TTCTTACGTC GGTGATGCTC      900

CCCTACGTGA ACAGAACGCT TAAGATATTA GAGTCAACCT TAAAATCGTA TGCTAAGAGT      960

ATGAATGAGA GTGCGCGAGT TAAGTGCGAT TTAGTGCTGA TAGGAGGATC TTCATATCTT     1020

CCTGGCCTGG CAGACGTACT AACGAAGCAT CAGAGCGTTG ATCGTATCTT AAGAGTTTCG     1080

GATCCTCGGG CTGCCGTGGC CGTCGGTTGC GCATTATATT CTTCATGCCT CTCAGGATCT     1140

GGGGGGTTGC TACTGATCGA CTGTGCAGCT CACACTGTCG CTATAGCGGA CAGAAGTTGT     1200

CATCAAATCA TTTGCGCTCC AGCGGGGGCA CCGATCCCCT TTTCAGGAAG CATGCCTTTG     1260

TACTTAGCCA GGGTCAACAA GAACTCGCAG CGTGAAGTCA CCGTGTTTGA AGGGGAGTAC     1320

GTTAAGTGCC CTAAGAACAG AAAGATCTGT GGAGCAAATA TAAGATTTTT TGATATAGGA     1380

GTGACGGGTG ATTCGTACGC ACCCGTTACC TTCTATATGG ATTTCTCCAT TTCAAGCGTA     1440

GGAGCCGTTT CATTCGTGGT GAGAGGTCCT GAGGGTAAGC AAGTGTCACT CACTGGAACT     1500

CCAGCGTATA ACTTTTCGTC TGTGGCTCTC GGATCACGCA GTGTCCGAGA ATTGCATATT     1560

AGTTTAAATA ATAAAGTTTT TCTCGGTTTG CTTCTACATA GAAAGGCGGA TCGACGAATA     1620

CTTTTCACTA AGGATGAAGC GATTCGATAC GCCGATTCAA TTGATATCGC GGATGTGCTA     1680

AAGGAATATA AAGTTACGC GGCCAGTGCC TTACCACCAG ACGAGGATGT CGAATTACTC     1740

CTGGGAAAGT CTGTTCAAAA AGTTTTACGG GAAGCAGAC TGGAAGAAAT ACCTCTCTAG     1800
```

(2) INFORMATION FOR SEQ ID NO:9:

(i) SEQUENCE CHARACTERISTICS:
        (A) LENGTH: 599 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Met Val Val Phe Gly Leu Asp Phe Gly Thr Thr Phe Ser Thr Val Cys
1               5                   10                  15

Val Tyr Lys Asp Gly Arg Val Phe Ser Phe Lys Gln Asn Asn Ser Ala
            20                  25                  30

Tyr Ile Pro Thr Tyr Leu Tyr Leu Phe Ser Asp Ser Asn His Met Thr
        35                  40                  45

Phe Gly Tyr Glu Ala Glu Ser Leu Met Ser Asn Leu Lys Val Lys Gly
    50                  55                  60

Ser Phe Tyr Arg Asp Leu Lys Arg Trp Val Gly Cys Asp Ser Ser Asn
65                  70                  75                  80
```

-continued

```
Leu Asp Ala Tyr Leu Asp Arg Leu Lys Pro His Tyr Ser Val Arg Leu
                85                  90                  95
Val Lys Ile Gly Ser Gly Leu Asn Glu Thr Val Ser Ile Gly Asn Phe
            100                 105                 110
Gly Gly Thr Val Lys Ser Glu Ala His Leu Pro Gly Leu Ile Ala Leu
        115                 120                 125
Phe Ile Lys Ala Val Ile Ser Cys Ala Glu Gly Ala Phe Ala Cys Thr
    130                 135                 140
Cys Thr Gly Val Ile Cys Ser Val Pro Ala Asn Tyr Asp Ser Val Gln
145                 150                 155                 160
Arg Asn Phe Thr Asp Gln Cys Val Ser Leu Ser Gly Tyr Gln Cys Val
                165                 170                 175
Tyr Met Ile Asn Glu Pro Ser Ala Ala Ala Leu Ser Ala Cys Asn Ser
            180                 185                 190
Ile Gly Lys Lys Ser Ala Asn Leu Ala Val Tyr Asp Phe Gly Gly Gly
        195                 200                 205
Thr Phe Asp Val Ser Ile Ile Ser Tyr Arg Asn Asn Thr Phe Val Val
    210                 215                 220
Arg Ala Ser Gly Gly Asp Leu Asn Leu Gly Gly Arg Asp Val Asp Arg
225                 230                 235                 240
Ala Phe Leu Thr His Leu Phe Ser Leu Thr Ser Leu Glu Pro Asp Leu
                245                 250                 255
Thr Leu Asp Ile Ser Asn Leu Lys Glu Ser Leu Ser Lys Thr Asp Ala
            260                 265                 270
Glu Ile Val Tyr Thr Leu Arg Gly Val Asp Gly Arg Lys Glu Asp Val
        275                 280                 285
Arg Val Asn Lys Asn Ile Leu Thr Ser Val Met Leu Pro Tyr Val Asn
290                 295                 300
Arg Thr Leu Lys Ile Leu Glu Ser Thr Leu Lys Ser Tyr Ala Lys Ser
305                 310                 315                 320
Met Asn Glu Ser Ala Arg Val Lys Cys Asp Leu Val Leu Ile Gly Gly
                325                 330                 335
Ser Ser Tyr Leu Pro Gly Leu Ala Asp Val Leu Thr Lys His Gln Ser
            340                 345                 350
Val Asp Arg Ile Leu Arg Val Ser Asp Pro Arg Ala Ala Val Ala Val
        355                 360                 365
Gly Cys Ala Leu Tyr Ser Ser Cys Leu Ser Gly Ser Gly Gly Leu Leu
    370                 375                 380
Leu Ile Asp Cys Ala Ala His Thr Val Ala Ile Ala Asp Arg Ser Cys
385                 390                 395                 400
His Gln Ile Ile Cys Ala Pro Ala Gly Ala Pro Ile Pro Phe Ser Gly
                405                 410                 415
Ser Met Pro Leu Tyr Leu Ala Arg Val Asn Lys Asn Ser Gln Arg Glu
            420                 425                 430
Val Ala Val Phe Glu Gly Glu Tyr Val Lys Cys Pro Lys Asn Arg Lys
        435                 440                 445
Ile Cys Gly Ala Asn Ile Arg Phe Phe Asp Ile Gly Val Thr Gly Asp
    450                 455                 460
Ser Tyr Ala Pro Val Thr Phe Tyr Met Asp Phe Ser Ile Ser Ser Val
465                 470                 475                 480
Gly Ala Val Ser Phe Val Val Arg Gly Pro Glu Gly Lys Gln Val Ser
                485                 490                 495
```

```
Leu Thr Gly Thr Pro Ala Tyr Asn Phe Ser Ser Val Ala Leu Gly Ser
            500                 505                 510

Arg Ser Val Arg Glu Leu His Ile Ser Leu Asn Asn Lys Val Phe Leu
        515                 520                 525

Gly Leu Leu His Arg Lys Ala Asp Arg Arg Ile Leu Phe Thr Lys
        530                 535                 540

Asp Glu Ala Ile Arg Tyr Ala Asp Ser Ile Asp Ile Ala Asp Val Leu
545                 550                 555                 560

Lys Glu Tyr Lys Ser Tyr Ala Ala Ser Ala Leu Pro Pro Asp Glu Asp
                565                 570                 575

Val Glu Leu Leu Leu Gly Lys Ser Val Gln Lys Val Leu Arg Gly Ser
            580                 585                 590

Arg Leu Glu Glu Ile Pro Leu
        595
```

(2) INFORMATION FOR SEQ ID NO:10:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
ATGTCGAATT ACTCCTGGGA AAGTCTGTTC AAAAAGTTTT ACGGGGAAGC AGACTGGAAG      60

AAATACCTCT CTAGGAGCAT AGCAGCACAC TCAAGTGAAA TTAAAACTCT ACCAGACATT     120

CGATTGTACG GCGGTAGGGT TGTAAAGAAG TCCGAATTCG AATCAGCACT TCCTAATTCT     180

TTTGAACAGG AATTAGGACT GTTCATACTG AGCGAACGGG AAGTGGGATG GAGCAAATTA     240

TGCGGAATAA CGGTGGAAGA AGCAGCATAC GATCTTACGA ATCCCAAGGC TTATAAATTC     300

ACTGCCGAGA CATGTAGCCC GGATGTAAAA GGTGAAGGAC AAAAATACTC TATGGAAGAC     360

GTGATGAATT TCATGCGTTT ATCAAATCTG GATGTTAACG ACAAGATGCT GACGGAACAG     420

TGTTGGTCGC TGTCCAATTC ATGCGGTGAA TTGATCAACC CAGACGACAA AGGGCGATTC     480

GTGGCTCTCA CCTTTAAGGA CAGAGACACA GCTGATGACA CGGGTGCCGC CAACGTGGAA     540

TGTCGCGTGG GCGACTATCT AGTTTACGCT ATGTCCCTGT TGAGCAGAG  ACCCAAAAA      600

TCGCAGTCTG GCAACATCTC TCTGTACGAA AAGTACTGTG AATACATCAG GACCTACTTA     660

GGGAGTACAG ACCTGTTCTT CACAGCGCCG GACAGGATTC CGTTACTTAC GGGCATCCTA     720

TACGATTTTT GTAAGGAATA CAACGTTTTC TACTCGTCAT ATAAGAGAAA CGTCGATAAT     780

TTCAGATTCT TCTTGGCGAA TTATATGCCT TTGATATCTG ACGTCTTTGT CTTCCAGTGG     840

GTAAAACCCG CGCCGGATGT TCGGCTGCTT TTTGAGTTAA GTGCAGCGGA ACTAACGCTG     900

GAGGTTCCCA CACTGAGTTT GATAGATTCT CAAGTTGTGG TAGGTCATAT CTTAAGATAC     960

GTAGAATCCT ACACATCAGA TCCAGCCATC GACGCGTTAG AAGACAAACT GGAAGCGATA    1020

CTGAAAAGTA GCAATCCCCG TCTATCGACA GCGCAACTAT GGGTTGGTTT CTTTTGTTAC    1080

TATGGTGAGT TCGTACGGC TCAAAGTAGA GTAGTGCAAA GACCAGGCGT ATACAAAACA    1140

CCTGACTCAG TGGGTGGATT TGAAATAAAC ATGAAAGATG TTGAGAAATT CTTCGATAAA    1200

CTTCAGAGAG AATTGCCTAA TGTATCTTTG CGGCGTCAGT TAACGGAGC  TAGAGCGCAT    1260

GAGGCTTTCA AAATATTTAA AAACGGAAAT ATAAGTTTCA GACCTATATC GCGTTTAAAC    1320

GTGCCTAGAG AGTTCTGGTA TCTGAACATA GACTACTTCA GGCACGCGAA TAGGTCCGGG    1380
```

```
TTAACCGAAG AAGAAATACT CATCCTAAAC AACATAAGCG TTGATGTTAG GAAGTTATGC    1440

GCTGAGAGAG CGTGCAATAC CCTACCTAGC GCGAAGCGCT TTAGTAAAAA TCATAAGAGT    1500

AATATACAAT CATCACGCCA AGAGCGGAGG ATTAAAGACC CATTGGTAGT CCTGAAAGAC    1560

ACTTTATATG AGTTCCAACA CAAGCGTGCC GGTTGGGGGT CTCGAAGCAC TCGAGACCTC    1620

GGGAGTCGTG CTGACCACGC GAAAGGAAGC GGTTGA                              1656

(2) INFORMATION FOR SEQ ID NO:11:

(i) SEQUENCE CHARACTERISTICS:
        (A) LENGTH: 551 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:
```

Met Ser Asn Tyr Ser Trp Glu Ser Leu Phe Lys Lys Phe Tyr Gly Glu
1               5                   10                  15

Ala Asp Trp Lys Lys Tyr Leu Ser Arg Ser Ile Ala Ala His Ser Ser
                20                  25                  30

Glu Ile Lys Thr Leu Pro Asp Ile Arg Leu Tyr Gly Gly Arg Val Val
            35                  40                  45

Lys Lys Ser Glu Phe Glu Ser Ala Leu Pro Asn Ser Phe Glu Gln Glu
50                  55                  60

Leu Gly Leu Phe Ile Leu Ser Glu Arg Glu Val Gly Trp Ser Lys Leu
65                  70                  75                  80

Cys Gly Ile Thr Val Glu Glu Ala Ala Tyr Asp Leu Thr Asn Pro Lys
                85                  90                  95

Ala Tyr Lys Phe Thr Ala Glu Thr Cys Ser Pro Asp Val Lys Gly Glu
            100                 105                 110

Gly Gln Lys Tyr Ser Met Glu Asp Val Met Asn Phe Met Arg Leu Ser
        115                 120                 125

Asn Leu Asp Val Asn Asp Lys Met Leu Thr Glu Gln Cys Trp Ser Leu
130                 135                 140

Ser Asn Ser Cys Gly Glu Leu Ile Asn Pro Asp Asp Lys Gly Arg Phe
145                 150                 155                 160

Val Ala Leu Thr Phe Lys Asp Arg Asp Thr Ala Asp Thr Gly Ala
                165                 170                 175

Ala Asn Val Glu Cys Arg Val Gly Asp Tyr Leu Val Tyr Ala Met Ser
            180                 185                 190

Leu Phe Glu Gln Arg Thr Gln Lys Ser Gln Ser Gly Asn Ile Ser Leu
        195                 200                 205

Tyr Glu Lys Tyr Cys Glu Tyr Ile Arg Thr Tyr Leu Gly Ser Thr Asp
210                 215                 220

Leu Phe Phe Thr Ala Pro Asp Arg Ile Pro Leu Leu Thr Gly Ile Leu
225                 230                 235                 240

Tyr Asp Phe Cys Lys Glu Tyr Asn Val Phe Tyr Ser Ser Tyr Lys Arg
                245                 250                 255

Asn Val Asp Asn Phe Arg Phe Leu Ala Asn Tyr Met Pro Leu Ile
            260                 265                 270

Ser Asp Val Phe Val Phe Gln Trp Val Lys Pro Ala Pro Asp Val Arg
        275                 280                 285

Leu Leu Phe Glu Leu Ser Ala Ala Glu Leu Thr Leu Glu Val Pro Thr

```
                     290                 295                 300
Leu Ser Leu Ile Asp Ser Gln Val Val Gly His Ile Leu Arg Tyr
305                 310                 315                 320

Val Glu Ser Tyr Thr Ser Asp Pro Ala Ile Asp Ala Leu Glu Asp Lys
                325                 330                 335

Leu Glu Ala Ile Leu Lys Ser Ser Asn Pro Arg Leu Ser Thr Ala Gln
                340                 345                 350

Leu Trp Val Gly Phe Phe Cys Tyr Tyr Gly Glu Phe Arg Thr Ala Gln
                355                 360                 365

Ser Arg Val Val Gln Arg Pro Gly Val Tyr Lys Thr Pro Asp Ser Val
370                 375                 380

Gly Gly Phe Glu Ile Asn Met Lys Asp Val Lys Phe Phe Asp Lys
385                 390                 395                 400

Leu Gln Arg Glu Leu Pro Asn Val Ser Leu Arg Arg Gln Phe Asn Gly
                405                 410                 415

Ala Arg Ala His Glu Ala Phe Lys Ile Phe Lys Asn Gly Asn Ile Ser
                420                 425                 430

Phe Arg Pro Ile Ser Arg Leu Asn Val Pro Arg Glu Phe Trp Tyr Leu
                435                 440                 445

Asn Ile Asp Tyr Phe Arg His Ala Asn Arg Ser Gly Leu Thr Glu Glu
450                 455                 460

Glu Ile Leu Ile Leu Asn Asn Ile Ser Val Asp Val Arg Lys Leu Cys
465                 470                 475                 480

Ala Glu Arg Ala Cys Asn Thr Leu Pro Ser Ala Lys Arg Phe Ser Lys
                485                 490                 495

Asn His Lys Ser Asn Ile Gln Ser Ser Arg Gln Glu Arg Arg Ile Lys
                500                 505                 510

Asp Pro Leu Val Val Leu Lys Asp Thr Leu Tyr Glu Phe Gln His Lys
                515                 520                 525

Arg Ala Gly Trp Gly Ser Arg Ser Thr Arg Asp Leu Gly Ser Arg Ala
530                 535                 540

Asp His Ala Lys Gly Ser Gly
545                 550

(2) INFORMATION FOR SEQ ID NO:12:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATGAGTTCCA ACACAAGCGT GCCGGTTGGG GGTCTCGAAG CACTCGAGAC CTCGGGAGTC       60

GTGCTGACCA CGCGAAAGGA AGCGGTTGAT AAGTTTTTTA ATGAACTAAA AAACGAAAAT      120

TACTCATCAG TTGACAGCAG CCGATTAAGC GATTCGGAAG TAAAAGAAGT GTTAGAGAAA      180

AGTAAAGAAA GTTTCAAAAG CGAACTGGCC TCCACTGACG AGCACTTCGT CTACCACATT      240

ATATTTTTCT TAATCCGATG TGCTAAGATA TCGACAAGTG AAAAGGTGAA GTACGTTGGT      300

AGTCATACGT ACGTGGTCGA CGGAAAAACG TACACCGTTC TTGACGCTTG GGTATTCAAC      360

ATGATGAAAA GTCTCACGAA GAAGTACAAA CGAGTGAATG GTCTGCGTGC GTTCTGTTGC      420

GCGTGCGAAG ATCTATATCT AACCGTCGCA CCAATAATGT CAGAACGCTT TAAGACTAAA      480
```

```
GCCGTAGGGA TGAAAGGTTT GCCTGTTGGA AAGGAATACT TAGGCGCCGA CTTTCTTTCG      540

GGAACTAGCA AACTGATGAG CGATCACGAC AGGGCGGTCT CCATCGTTGC AGCGAAAAAC      600

GCTGTCGATC GTAGCGCTTT CACGGGTGGG GAGAGAAAGA TAGTTAGTTT GTATGATCTA      660

GGGAGGTACT AA                                                          672
```

(2) INFORMATION FOR SEQ ID NO:13:

(i) SEQUENCE CHARACTERISTICS:
        (A) LENGTH: 223 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Met Ser Ser Asn Thr Ser Val Pro Val Gly Gly Leu Glu Ala Leu Glu
1               5                   10                  15

Thr Ser Gly Val Val Leu Thr Thr Arg Lys Glu Ala Val Asp Lys Phe
            20                  25                  30

Phe Asn Glu Leu Lys Asn Glu Asn Tyr Ser Ser Val Asp Ser Ser Arg
        35                  40                  45

Leu Ser Asp Ser Glu Val Lys Glu Val Leu Glu Lys Ser Lys Glu Ser
    50                  55                  60

Phe Lys Ser Glu Leu Ala Ser Thr Asp Glu His Phe Val Tyr His Ile
65                  70                  75                  80

Ile Phe Phe Leu Ile Arg Cys Ala Lys Ile Ser Thr Ser Glu Lys Val
                85                  90                  95

Lys Tyr Val Gly Ser His Thr Tyr Val Val Asp Gly Lys Thr Tyr Thr
            100                 105                 110

Val Leu Asp Ala Trp Val Phe Asn Met Met Lys Ser Leu Thr Lys Lys
            115                 120                 125

Tyr Lys Arg Val Asn Gly Leu Arg Ala Phe Cys Cys Ala Cys Glu Asp
130                 135                 140

Leu Tyr Leu Thr Val Ala Pro Ile Met Ser Glu Arg Phe Lys Thr Lys
145                 150                 155                 160

Ala Val Gly Met Lys Gly Leu Pro Val Gly Lys Glu Tyr Leu Gly Ala
                165                 170                 175

Asp Phe Leu Ser Gly Thr Ser Lys Leu Met Ser Asp His Asp Arg Ala
            180                 185                 190

Val Ser Ile Val Ala Ala Lys Asn Ala Val Asp Arg Ser Ala Phe Thr
            195                 200                 205

Gly Gly Glu Arg Lys Ile Val Ser Leu Tyr Asp Leu Gly Arg Tyr
210                 215                 220
```

(2) INFORMATION FOR SEQ ID NO:14:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
ATGGAGTTGA TGTCCGACAG CAACCTTAGC AACCTGGTGA TAACCGACGC CTCTAGTCTA       60

AATGGTGTCG ACAAGAAGCT TTTATCTGCT GAAGTTGAAA AATGTTGGT GCAGAAAGGG       120
```

```
GCTCCTAACG AGGGTATAGA AGTGGTGTTC GGTCTACTCC TTTACGCACT CGCGGCAAGA      180

ACCACGTCTC CTAAGGTTCA GCGCGCAGAT TCAGACGTTA TATTTTCAAA TAGTTTCGGA      240

GAGAGGAATG TGGTAGTAAC AGAGGGTGAC CTTAAGAAGG TACTCGACGG GTGTGCGCCT      300

CTCACTAGGT TCACTAATAA ACTTAGAACG TTCGGTCGTA CTTTCACTGA GGCTTACGTT      360

GACTTTTGTA TCGCGTATAA GCACAAATTA CCCCAACTCA ACGCCGCGGC GGAATTGGGG      420

ATTCCAGCTG AAGATTCGTA CTTAGCTGCA GATTTTCTGG GTACTTGCCC GAAGCTCTCT      480

GAATTACAGC AAAGTAGGAA GATGTTCGCG AGTATGTACG CTCTAAAAAC TGAAGGTGGA      540

GTGGTAAATA CACCAGTGAG CAATCTGCGT CAGCTAGGTA GAAGGGAAGT TATGTAA         597
```

(2) INFORMATION FOR SEQ ID NO:15:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met Glu Leu Met Ser Asp Ser Asn Leu Ser Asn Leu Val Ile Thr Asp
1               5                   10                  15

Ala Ser Leu Asn Gly Val Asp Lys Lys Leu Leu Ser Ala Glu Val
            20                  25                  30

Glu Lys Met Leu Val Gln Lys Gly Ala Pro Asn Glu Gly Ile Glu Val
            35                  40                  45

Val Phe Gly Leu Leu Leu Tyr Ala Leu Ala Ala Arg Thr Thr Ser Pro
    50                  55                  60

Lys Val Gln Arg Ala Asp Ser Asp Val Ile Phe Ser Asn Ser Phe Gly
65                  70                  75                  80

Glu Arg Asn Val Val Val Thr Glu Gly Asp Leu Lys Lys Val Leu Asp
                85                  90                  95

Gly Cys Ala Pro Leu Thr Arg Phe Thr Asn Lys Leu Arg Thr Phe Gly
            100                 105                 110

Arg Thr Phe Thr Glu Ala Tyr Val Asp Phe Cys Ile Ala Tyr Lys His
            115                 120                 125

Lys Leu Pro Gln Leu Asn Ala Ala Glu Leu Gly Ile Pro Ala Glu
130                 135                 140

Asp Ser Tyr Leu Ala Ala Asp Phe Leu Gly Thr Cys Pro Lys Leu Ser
145                 150                 155                 160

Glu Leu Gln Gln Ser Arg Lys Met Phe Ala Ser Met Tyr Ala Leu Lys
                165                 170                 175

Thr Glu Gly Gly Val Val Asn Thr Pro Val Ser Asn Leu Arg Gln Leu
            180                 185                 190

Gly Arg Arg Glu Val Met
        195
```

(2) INFORMATION FOR SEQ ID NO:16:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

| | | | | | |
|---|---|---|---|---|---|
| ATGGAAGATT | ACGAAGAAAA | ATCCGAATCG | CTCATACTGC | TACGCACGAA | TCTGAACACT | 60
| ATGCTTTTAG | TGGTCAAGTC | CGATGCTAGT | GTAGAGCTGC | CTAAACTACT | AATTTGCGGT | 120
| TACTTACGAG | TGTCAGGACG | TGGGGAGGTG | ACGTGTTGCA | ACCGTGAGGA | ATTAACAAGA | 180
| GATTTTGAGG | GCAATCATCA | TACGGTGATC | CGTTCTAGAA | TCATACAATA | TGACAGCGAG | 240
| TCTGCTTTTG | AGGAATTCAA | CAACTCTGAT | TGCGTAGTGA | AGTTTTTCCT | AGAGACTGGT | 300
| AGTGTCTTTT | GGTTTTTCCT | TCGAAGTGAA | ACCAAAGGTA | GAGCGGTGCG | ACATTTGCGC | 360
| ACCTTCTTCG | AAGCTAACAA | TTTCTTCTTT | GGATCGCATT | GCGGTACCAT | GGAGTATTGT | 420
| TTGAAGCAGG | TACTAACTGA | AACTGAATCT | ATAATCGATT | CTTTTTGCGA | AGAAAGAAAT | 480
| CGTTAA | | | | | | 486

(2) INFORMATION FOR SEQ ID NO:17:

(i) SEQUENCE CHARACTERISTICS:
        (A) LENGTH: 161 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Met Glu Asp Tyr Glu Glu Lys Ser Glu Ser Leu Ile Leu Leu Arg Thr
  1               5                  10                  15

Asn Leu Asn Thr Met Leu Leu Val Val Lys Ser Asp Ala Ser Val Glu
             20                  25                  30

Leu Pro Lys Leu Leu Ile Cys Gly Tyr Leu Arg Val Ser Gly Arg Gly
         35                  40                  45

Glu Val Thr Cys Cys Asn Arg Glu Glu Leu Thr Arg Asp Phe Glu Gly
 50                  55                  60

Asn His His Thr Val Ile Arg Ser Arg Ile Ile Gln Tyr Asp Ser Glu
 65                  70                  75                  80

Ser Ala Phe Glu Glu Phe Asn Asn Ser Asp Cys Val Val Lys Phe Phe
                 85                  90                  95

Leu Glu Thr Gly Ser Val Phe Trp Phe Phe Leu Arg Ser Glu Thr Lys
            100                 105                 110

Gly Arg Ala Val Arg His Leu Arg Thr Phe Phe Glu Ala Asn Asn Phe
        115                 120                 125

Phe Phe Gly Ser His Cys Gly Thr Met Glu Tyr Cys Leu Lys Gln Val
    130                 135                 140

Leu Thr Glu Thr Glu Ser Ile Ile Asp Ser Phe Cys Glu Glu Arg Asn
145                 150                 155                 160

Arg
```

(2) INFORMATION FOR SEQ ID NO:18:

(i) SEQUENCE CHARACTERISTICS:
        (A) LENGTH: 618 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

-continued

| | | | | |
|---|---|---|---|---|
| ATGAGGGTTA | TAGTGTCTCC | TTATGAAGCT | GAAGACATTC | TGAAAAGATC | GACTGACATG | 60 |
| TTACGAAACA | TAGACAGTGG | GGTCTTGAGC | ACTAAAGAAT | GTATCAAGGC | ATTCTCGACG | 120 |
| ATAACGCGAG | ACCTACATTG | TGCGAAGGCT | TCCTACCAGT | GGGGTGTTGA | CACTGGGTTA | 180 |
| TATCAGCGTA | ATTGCGCTGA | AAAACGTTTA | ATTGACACGG | TGGAGTCAAA | CATACGGTTG | 240 |
| GCTCAACCTC | TCGTGCGTGA | AAAAGTGGCG | GTTCATTTTT | GTAAGGATGA | ACCAAAAGAG | 300 |
| CTAGTAGCAT | TCATCACGCG | AAAGTACGTG | GAACTCACGG | GCGTGGGAGT | GAGAGAAGCG | 360 |
| GTGAAGAGGG | AAATGCGCTC | TCTTACCAAA | ACAGTTTTAA | ATAAAATGTC | TTTGGAAATG | 420 |
| GCGTTTTACA | TGTCACCACG | AGCGTGGAAA | AACGCTGAAT | GGTTAGAACT | AAAATTTTCA | 480 |
| CCTGTGAAAA | TCTTTAGAGA | TCTGCTATTA | GACGTGGAAA | CGCTCAACGA | ATTGTGCGCC | 540 |
| GAAGATGATG | TTCACGTCGA | CAAAGTAAAT | GAGAATGGGG | ACGAAAATCA | CGACCTCGAA | 600 |
| CTCCAAGACG | AATGTTAA | | | | | 618 |

(2) INFORMATION FOR SEQ ID NO:19:

(i) SEQUENCE CHARACTERISTICS:
        (A) LENGTH: 205 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Met Arg Val Ile Val Ser Pro Tyr Glu Ala Glu Asp Ile Leu Lys Arg
 1               5                  10                  15

Ser Thr Asp Met Leu Arg Asn Ile Asp Ser Gly Val Leu Ser Thr Lys
            20                  25                  30

Glu Cys Ile Lys Ala Phe Ser Thr Ile Thr Arg Asp Leu His Cys Ala
        35                  40                  45

Lys Ala Ser Tyr Gln Trp Gly Val Asp Thr Gly Leu Tyr Gln Arg Asn
    50                  55                  60

Cys Ala Glu Lys Arg Leu Ile Asp Thr Val Glu Ser Asn Ile Arg Leu
65                  70                  75                  80

Ala Gln Pro Leu Val Arg Glu Lys Val Ala Val His Phe Cys Lys Asp
                85                  90                  95

Glu Pro Lys Glu Leu Val Ala Phe Ile Thr Arg Lys Tyr Val Glu Leu
            100                 105                 110

Thr Gly Val Gly Val Arg Glu Ala Val Lys Arg Glu Met Arg Ser Leu
        115                 120                 125

Thr Lys Thr Val Leu Asn Lys Met Ser Leu Glu Met Ala Phe Tyr Met
    130                 135                 140

Ser Pro Arg Ala Trp Lys Asn Ala Glu Trp Leu Glu Leu Lys Phe Ser
145                 150                 155                 160

Pro Val Lys Ile Phe Arg Asp Leu Leu Leu Asp Val Glu Thr Leu Asn
                165                 170                 175

Glu Leu Cys Ala Glu Asp Asp Val His Val Asp Lys Val Asn Glu Asn
            180                 185                 190

Gly Asp Glu Asn His Asp Leu Glu Leu Gln Asp Glu Cys
        195                 200                 205
```

(2) INFORMATION FOR SEQ ID NO:20:

(i) SEQUENCE CHARACTERISTICS:
        (A) LENGTH: 21 base pairs

-continued (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TGCTGGAGCT TGAGGTTCTG C                                         21

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CGGAATTCAC CATGGAGTTG ATGTCCGACA G                              31

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

AGCGGATCCA TGGCAGATTC GTGCGTAGCA GTA                            33

(2) INFORMATION FOR SEQ ID NO:23:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

ACATTGGTTA AGTTTAACGA AAATGATTAG TAAATAATAA ATCGAACGTG GGTGTATCTA     60

CCTGACGTAT CAACTTAAGC TGTTACTGAG TAATTAAACC AACAAGTGTT GGTGTAATGT    120

GTATGTTGAT GTAGAGAAAA ATCCGTTTGT AGAACGGTGT TTTTCTCTTC TTTATTTTTA    180

AAAAAAAAAT AAAAAAAAAA AAAAAAAGC GGCCGC                              216

GRAPEVINE LEAFROLL VIRUS (TYPE 2) PROTEINS AND THEIR USES

This application claims the benefit of U.S. Provisional Patent Application Ser. No. 60/047,194, filed May 20, 1997.

This work was supported by the U.S. Department of Agriculture Cooperative Grant No. 58-2349-9-01. The U.S. Government may have certain rights in the invention.

FIELD OF THE INVENTION

The present invention relates to grapevine leafroll virus (type 2) proteins, DNA molecules encoding these proteins, and their uses.

BACKGROUND OF THE INVENTION

The world's most widely grown fruit crop, the grape (Vitis sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards are planted with traditional grapevine cultivars, which have been perpetuated for centuries by vegetative propagation. Several important grapevine virus and virus-like diseases, such as grapevine leafroll, corky bark, and Rupestris stem pitting, are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) the rugose wood complex (Martelli, ed., *Graft Transmissible Diseases of Grapevines, Handbook for Detection and Diagnosis*, FAO, UN, Rome, Italy (1993)).

Of the major virus diseases, the grapevine leafroll complex is the most widely distributed throughout the world. According to Goheen ("Grape Leafroll," in Frazier et al., eds., *Virus Diseases of Small Fruits and Grapevines (A Handbook)*, University of California, Division of Agricultural Sciences, Berkeley, Calif., USA, pp. 209–212 (1970) ("Goheen (1970)"), grapevine leafroll-like disease was described as early as the 1850s in German and French literature. However, the viral nature of the disease was first demonstrated by Scheu (Scheu, "Die Rollkrankheit des Rebstockes (Leafroll of grapevine)," *D. D. Weinbau* 14:222–358 (1935) ("Scheu (1935)")). In 1946, Harmon and Snyder (Harmon et al., "Investigations on the Occurrence, Transmission, Spread and Effect of 'White' Fruit Colour in the Emperor Grape," *Proc. Am. Soc. Hort. Sci.* 74:190–194 (1946)) determined the viral nature of White Emperor disease in California. It was later proven by Goheen et al. (Goheen et al., "Leafroll (White Emperor Disease) of Grapes in California, *Phytopathology*, 48:51–54 (1958) ("Goheen (1958)")) that both leafroll and "White Emperor" diseases were the same, and only the name "leafroll" was retained.

Leafroll is a serious viral disease of grapes and occurs wherever grapes are grown. This wide distribution of the disease has come about through the propagation of diseased vines. It affects almost all cultivated and rootstock varieties of Vitis. Although the disease is not lethal, it causes yield losses and reduction of sugar content. Scheu estimated in 1936 that 80 per cent of all grapevines planted in Germany were infected (Scheu, *Mein Winzerbuch*, Berlin:Reichsnahrstand-Verlags (1936)). In many California wine grape vineyards, the incidence of leafroll (based on a survey of field symptoms conducted in 1959) agrees with Scheu's initial observation in German vineyards (Goheen et al., "Studies of Grape Leafroll in California," *Amer. J. Enol. Vitic.*, 10:78–84 (1959)). The current situation on leafroll disease does not seem to be any better (Goheen, "Diseases Caused by Viruses and Viruslike Agents," *The American Phytopathological Society*, St. Paul, Minn.:APS Press, 1:47–54 (1988) ("Goheen (1988)"). Goheen also estimated that the disease causes an annual loss of about 5–20 per cent of the total grape production (Goheen (1970) and Goheen (1988)). The amount of sugar in individual berries of infected vines is only about ½ to ⅔ that of berries from noninfected vines (Goheen (1958)).

Symptoms of leafroll disease vary considerably depending upon the cultivar, environment, and time of the year. On red or dark-colored fruit varieties, the typical downward rolling and interveinal reddening of basal, mature leaves is the most prevalent in autumn; but not in spring or early summer. On light-colored fruit varieties however, symptoms are less conspicuous, usually with downward rolling accompanied by interveinal chlorosis. Moreover, many infected rootstock cultivars do not develop symptoms. In these cases, the disease is usually diagnosed with a woody indicator indexing assay using *Vitis vivifera* cv. Carbernet Franc (Goheen (1988)).

Ever since Scheu demonstrated that leafroll was graft transmissible, a virus etiology has been suspected (Scheu (1935)). Several virus particle types have been isolated from leafroll diseased vines. These include potyvirus-like (Tanne et al., "Purification and Characterization of a Virus Associated with the Grapevine Leafroll Disease," *Phytopathology*, 67:442–447 (1977)), isometric virus-like (Castellano et al., "Virus-like Particles and Ultrastructural Modifications in the Phloem of Leafroll-affected Grapevines," *Vitis*, 22:23–39 (1983) ("Castellano (1983)") and Namba et al., "A Small Spherical Virus Associated with the Ajinashika Disease of Koshu Grapevine, *Ann. Phytopathol. Soc. Japan*, 45:70–73 (1979)), and closterovirus-like (Namba, "Grapevine Leafroll Virus, a Possible Member of Closteroviruses, *Ann. Phytopathol. Soc. Japan*, 45:497–502 (1979)) particles. In recent years, however, long flexuous closteroviruses ranging from 1,400 to 2,200 nm have been most consistently associated with leafroll disease (FIG. 1) (Castellano (1983), Faoro et al., "Association of a Possible Closterovirus with Grapevine Leafroll in Northern Italy," *Riv. Patol. Veg., Ser IV*, 17:183–189 (1981), Gugerli et al., "L'enroulement de la vigne: mise en évidence de particules virales et développement d'une méthode immuno-enzymatique pour le diagnostic rapide (Grapevine Leafroll: Presence of Virus Particles and Development of an Immuno-enzyme method for Diagnosis and Detection)," *Rev. Suisse Viticult. Arboricult. Hort.,* 16:299–304 (1984) ("Gugerli (1984)"), Hu et al., "Characterization of Closterovirus-like Particles Associated with Grapevine Leafroll Disease," *J. Phytopathol.,* 128:1–14 (1990) ("Hu (1990)"), Milne et al., "Closterovirus-like Particles of Two Types Associated with Diseased Grapevines," *Phytopathol. Z.,* 110:360–368 (1984), Zee et al., "Cytopathology of Leafroll-diseased Grapevines and the Purification and Serology of Associated Closteroviruslike Particles," Phytopathology, 77:1427–1434 (1987) ("Zee (1987)"), and Zimmermann et al., "Characterization and Serological Detection of Four Closterovirus-like Particles Associated with Leafroll Disease on Grapevine," *J. Phytopathol.,* 130:205–218 (1990) ("Zimmermann (1990)")). These closteroviruses are referred to as grapevine leafroll associated viruses ("GLRaV"). At least six serologically distinct types of GLRaV's (GLRaV-1 to -6) have been detected from leafroll diseased vines (Table 1) (Boscia et al., "Nomenclature of Grapevine Leafroll-associated Putative Closteroviruses, *Vitis,* 34:171–175 (1995) ("Boscia (1995)") and (Martelli, "Leafroll," pp. 37–44 in Martelli, ed., *Graft Transmissible Diseases of Grapevines, Handbook for Detection and Diagnosis,* FAO, Rome Italy, (1993) ("Martelli I")). The first five of these were confirmed in the 10th Meeting of the International Council for the Study of Virus and Virus Diseases of the Grapevine ("ICVG") (Volos, Greece, 1990).

TABLE 1

| Type | Particle length (nm) | Coat protein Mr (X10³) | Reference |
|---|---|---|---|
| GLRaV-1 | 1,400–2,200 | 39 | Gugerli (1984) |
| GLRaV-2 | 1,400–1,800 | 26 | Gugerli (1984) Zimmermann (1990) |
| GLRaV-3 | 1,400–2,200 | 43 | Zee(1987) |
| GLRaV-4 | 1,400–2,200 | 36 | Hu (1990) |
| GLRaV-5 | 1,400–2,200 | 36 | Zimmermann (1990) |
| GLRaV-6 | 1,400–2,200 | 36 | Gugerli (1993) |

Through the use of monoclonal antibodies, however, the original GLRaV II described in Gugerli (1984) has been shown to be an apparent mixture of at least two components, IIa and IIb (Gugerli et al., "Grapevine Leafroll Associated Virus II Analyzed by Monoclonal Antibodies," 11*th Meeting of the International Council for the Study of Viruses and Virus Diseases of the Grapevine,* Montreux, Switzerland, pp. 23–24 (1993) ("Gugerli (1993)")). Recent investigation with comparative serological assays (Boscia (1995)) demonstrated that the IIb component of cv. Chasselas 8/22 is the same as the GLRaV-2 isolate from France (Zimmermann (1990)) which also include the isolates of grapevine corky bark associated closteroviruses from Italy (GCBaV-BA) (Boscia (1995)) and from the United States (GCBaV-NY) (Namba et al., "Purification and Properties of Closteroviruslike Particles Associated with Grapevine Corky Bark Disease," *Phytopathology,* 81:964–970 (1991) ("Namba (1991)")). The Ia component of cv. Chasselas 8/22 was given the provisional name of grapevine leafroll associated virus 6 (GLRaV-6). Furthermore, the antiserum to the CA-5 isolate of GLRaV-2 produced by Boscia et al. (Boscia et al., "Characterization of Grape Leafroll Associated Closterovirus (GLRaV) Serotype II and Comparison with GLRaV Serotype III," *Phytopathology,* 80:117 (1990)) was shown to contain antibodies to both GLRaV-2 and GLRaV-1, with a prevalence of the latter (Boscia (1995)).

Virions of GLRaV-2 are flexuous, filamentous particles about 1,400–1,800 nm in length (Gugerli et al., "L'enroulement de la Vigne: Mise en Evidence de Particles Virales et Development d'une Methode Immunoenzymatique Pour le Diagnostic Rapide (Grapevine Leafroll: Presence of Virus Particles and Development of an Immuno-enzyme Method for Diagnosis and Detection)," *Rev. Suisse Viticult. Arboricult. Horticult.* 16:299–304 (1984)). A double-stranded RNA (dsRNA) of about 15 kb was consistently isolated from GLRaV-2 infected tissues (Goszczynski et al., "Detection of Two Strains of Grapevine Leafroll-Associated Virus 2," *Vitis* 35:133–35 (1996)). The coat protein of GLRaV-2 is ca 22~26 kDa (Zimmermann et al., "Characterization and Serological Detection of Four Closterovirus-like Particles Associated with Leafroll Disease on Grapevine," *J. Phytopathology* 130:205–18 (1990); Gugerli and Ramel, Extended abstracts: "Grapevine Leafroll Associated Virus II Analyzed by Monoclonal Antibodies," 11th ICVG at Montreux, Switzerland, Gugerli, ed., Federal Agricultural Research Station of Changins, CH-1260 Nyon, Switzerland, p. 23–24 (1993); Boscia et al., "Nomenclature of Grapevine Leafroll-Associated Putative Closteroviruses," *Vitis* 34:171–75 (1995)), which is considerably smaller than other GLRaVs (35~43 kDa) (Zee et al., "Cytopathology of Leafroll-Diseased Grapevines and the Purification and Serology of Associated Closterovirus Like Particles," *Phytopathology* 77:1427~34 (1987); Hu et al., "Characterization of Closterovirus-Like Particles Associated with Grapevine Leafroll Disease," *J. of Phytopathology* 128:1–14 (1990); Ling et al., "The Coat Protein Gene of Grapevine Leafroll Associated Closterovirus-3: Cloning, Nucleotide Sequencing and Expression in Transgenic Plants," *Arch. of Virology* 142:1101–16 (1997)). Although GLRaV-2 has been classififed as a member of the genus Closterovirus based on particle morphology and cytopathology (Martelli, Circular of ICTV-Plant Virus Subcommittee Study Group on *Closterolike Viruses" (1996)), its molecular and biochemical properties are not well characterized.

In the closterovirus group, several viruses have recently been sequenced. The partial or complete genome sequences of beet yellows virus (BYV) (Agranovsky et al. "Nucleotide Sequence of the 3'-Terminal Half of Beet Yellows Closterovirus RNA Genome Unique Arrangement of Eight Virus Genes," *J. General Virology* 72:15–24 (1991); Agranovsky et al., "Beet Yellows Closterovirus: Complete Genome Structure and Identification of a Papain-like Thiol Protease," Virology 198:311–24 (1994)), beet yellow stunt virus (BYSV) (Karasev et al., "Organization of the 3'-Terminal Half of Beet Yellow Stunt Virus Genome and Implications for the Evolution of Closteroviruses," Virology 221:199–207 (1996)), citrus tristeza virus (CTV) (Pappu et al., "Nucleotide Sequence and Organization of Eight 3' Open Reading Frames of the Citrus Tristeza Closterovirus Genome," Virology 199:35–46 (1994); Karasev et al., "Complete Sequence of the Citrus Tristeza Virus RNA Genome," Virology 208:511-20 (1995)), lettuce infectious yellows virus (LIYV) (Klaassen et al., "Partial Characterization of the Lettuce Infectious Yellows Virus Genomic RNAs, Identification of the Coat Protein Gene and Comparison of its Amino Acid Sequence With Those of Other Filamentous RNA Plant Viruses," *J. General Virology* 75:1525–33 (1994); Klaassen et al., "Genome Structure and Phylogenetic Analysis of Lettuce Infectious Yellows Virus, a Whitefly-Transmitted, Bipartite Closterovirus," *Virology* 208:99–110 (1995)), little cherry virus (LChV) (Keim and Jelkmann, "Genome Analysis of the 3'-Terminal Part of the Little Cherry Disease Associated dsRNA Reveals a Monopartite Clostero-Like Virus," *Arch. Virology* 141:1437–51 (1996); Jelkmann et al., "Complete Genome Structure and Phylogenetic Analysis of Little Cherry Virus, a Mealybug-Transmissible Closterovirus," *J. General Virology* 78:2067–71 (1997)), and GLRaV-3 (Ling et al., "Nucleotide Sequence of the 3' Terminal Two-Thirds of the Grapevine Leafroll Associated Virus-3 Genome Reveals a Typical Monopartite Closterovirus," *J. Gen. Virology* 79(5):1289–1301 (1998)) revealed several common features of the closteroviruses, including the presence of HSP70 chaperone heat shock protein and a duplicate of the coat protein gene (Agranovsky "Principles of Molecular Organization, Expression, and Evolution of Closteroviruses: Over the Barriers," *Adv. in Virus Res.* 47:119–218 (1996); Dolja et al. "Molecular Biology and Evolution of Closteroviruses: Sophisticated Build-up of Large RNA Genomes," *Annual Rev. Photopathology* 32:261–85 (1994); Boyko et al., "Coat Protein Gene Duplication in a Filamentous RNA Virus of Plants," *Proc. Nat. Acad. Sci. USA* 89:9156–60 (1992)). Characterization of the genome organization of GLRaVs would provide molecular information on the serologically distinct closteroviruses that cause similar leafroll symptoms in grapevine.

Several shorter closteroviruses (particle length 800 nm long) have also been isolated from grapevines. One of these, called grapevine virus A ("GVA") has also been found associated, though inconsistently, with the leafroll disease (Agran et al., "Occurrence of Grapevine Virus A (GVA) and Other Closteroviruses in Tunisian Grapevines Affected by Leafroll Disease," *Vitis*, 29:43–48 (1990), Conti, et al., "Closterovirus Associated with Leafroll and Stem Pitting in Grapevine," *Phytopathol. Mediterr.*, 24:110–113 (1985), and Conti et al., "A Closterovirus from a Stem-pitting-diseased Grapevine," *Phytopathology*, 70:394–399 (1980)). The etiology of GVA is not really known; however, it appears to be more consistently associated with rugose wood sensu lato (Rosciglione at al., "Maladies de l'enroulement et du bois strié de la vigne: analyse microscopique et sérologique (Leafroll and Stem Pitting of Grapevine: Microscopical and Serological Analysis)," *Rev. Suisse Vitic Arboric. Hortic.*, 18:207–211 (1986) ("Rosciglione (1 986)"), and Zimmermann (1 990)). Moreover, another short closterovirus (800 nm long) named grapevine virus B ("GVB") has been isolated and characterized from corky bark-affected vines (Boscia et al., "Properties of a Filamentous Virus Isolated from Grapevines Affected by Corky Bark," *Arch. Virol.*, 130:109–120 (1993) and Namba (1991)).

As suggested by Martelli I, leafroll symptoms may be induced by more than one virus or they may be simply a general plant physiological response to invasion by an array of phloem-inhabiting viruses. Evidence accumulated in the last 15 years strongly favors the idea that grapevine leafroll is induced by one (or a complex) of long closteroviruses (particle length 1,400 to 2,200 nm).

Grapevine leafroll is transmitted primarily by contaminated scions and rootstocks. However, under field conditions, several species of mealybugs have been shown to be the vector of leafroll (Engelbrecht et al., "Transmission of Grapevine Leafroll Disease and Associated Closteroviruses by the Vine Mealybug Planococcus-ficus," *Phytophylactica*, 22:341–346 (1990), Rosciglione, et al., "Transmission of Grapevine Leafroll Disease and an Associated Closterovirus to Healthy Grapevine by the Mealybug Planococcus ficus," (Abstract), *Phytoparasitica*, 17:63–63 (1989), and Tanne, "Evidence for the Transmission by Mealybugs to Healthy Grapevines of a Closter-like Particle Associated with Grapevine Leafroll Disease," *Phytoparasitica*, 16:288 (1988)). Natural spread of leafroll by insect vectors is rapid in various parts of the world. In New Zealand, observations of three vineyards showed that the number of infected vines nearly doubled in a single year (Jordan et al., "Spread of Grapevine Leafroll and its Associated Virus in New Zealand Vineyards," I1Ith *Meeting of the International Council for the Study of Viruses and Virus Diseases of the Grapevine*, Montreux, Switzerland, pp. 113–114 (1993)). One vineyard became 90% infected 5 years after GLRaV-3 was first observed. Prevalence of leafroll worldwide may increase as chemical control of mealybugs becomes more difficult due to the unavailability of effective insecticides.

In view of the serious risk grapevine leafroll virus poses to vineyards and the absence of an effective treatment of it, the need to prevent this affliction continues to exist. The present invention is directed to overcoming this deficiency in the art.

SUMMARY OF INVENTION

The present invention relates to an isolated protein or polypeptide corresponding to a protein or polypeptide of a grapevine leafroll virus (type 2). The encoding RNA and DNA molecules, in either isolated form or incorporated in an expression system, a host cell, a transgenic Vitis or citrus scion or rootstock cultivar, or a transgenic Nicotiana plant or beet plant are also disclosed.

Another aspect of the present invention relates to a method of imparting grapevine leafroll virus (type 2) resistance to Vitis scion or rootstock cultivars or Nicotiana plants by transforming them with a DNA molecule encoding the protein or polypeptide corresponding to a protein or polypeptide of a grapevine leafroll virus (type 2). Other aspects of the present invention relate to a method of imparting beet yellows virus resistance to beet plants and a method of imparting tristeza virus resistance to citrus scion or rootstock cultivars, both by transforming the plants or cultivars with a DNA molecule encoding the protein or polypeptide corresponding to a protein or polypeptide of a grapevine leafroll virus (type 2).

The present invention also relates to an antibody or binding portion thereof or probe which recognizes the protein or polypeptide.

Grapevine leafroll virus resistant transgenic variants of the current commercial grape cultivars and rootstocks allows for more complete control of the virus, while retaining the varietal characteristics of specific cultivars. Furthermore, these variants permit control of GLRaV-2 transmitted either by contaminated scions or rootstocks or by a presently uncharacterized insect vector. With respect to the latter mode of transmission, the present invention circumvents increased restriction of pesticide use which has made chemical control of insect infestation increasingly difficult. In this manner, the interests of the environment and the economics of grape cultivation and wine making are all furthered by the present invention.

BRIEF DESCRIPTION OF THE DRAWINGS

In FIG. 1A: lane M, lambda Hind III DNA marker; and lane 1, dsRNA pattern in 1% agarose gel stained with ethidium bromide. FIG. 1B is a northern hybridization of isolated high molecular weight dsRNA of GLRaV-2 with a probe prepared with 32P [(α-dATP] labeled cDNA insert from GLRaV-2 specific cDNA clone TC-1. Lane 1, high molecular weight dsRNA of GLRaV-2. Lane 2, total RNA extracted from healthy grapevine.

FIGS. 3A–3D are comparisons between ORF1a/ORF1b of GLRaV-2 and BYV. FIGS. 3A–3D show the conserved domains of two papain-like proteases (P-PRO), methyltransferase (MT/MTR), helicase (HEL), and RNA-dependent RNA polymerase (RdRP), respectively. Exclamation marks indicate the predicted catalytic residues of the leader papain-like protease; slashes indicate the predicted cleavage sites. The conserved motifs of the MT, HEL, and RdRP domains are highlighted with overlines marked with respective letters. The alignment is constructed using the MegAlign program in DNASTAR.

FIGS. 4A and 4B are alignments of the nucleotide (FIG. 4A) and deduced amino acid (FIG. 4B) sequences of ORF1a/ORF1b overlapping region of GLRaV-2, BYV, BYSV, and CTV. Identical nucleotides and amino acids are shown in consensus. GLRaV-2 putative+1 frameshift site (TAGC) and its corresponding sites of BYV (TAGC) and BYSV (TAGC) and CTV (CGGC) at nucleotide and amino acid sequences are highlighted with underlines.

FIG. 5 is an alignment of the amino acid sequence of HSP70 protein of GLRaV-2 and BYV. The conserved motifs (A to H) are indicated with overlines and marked with respective letters. The alignment was conducted with the MegAlign program of DNASTAR.

FIGS. 6A–6B. FIG. 6A is a comparison of the coat protein (CP) and coat protein duplicate (CPd) of GLRaV-2 with other closteroviruses. The amino acid sequence of the GLRaV-2 CP and CPd are aligned with the CP and CPd of BYV, BYSV, and CTV. The conserved amino acid residues are in bold and the consensus sequences are indicated. Sequence alignment and phylogenetic tree were constructed by Clustal Method in the MegAlign Program of DNASTAR. FIG. 6B is a tentative phylogenetic tree of the CP and CPd of GLRaV-2 with BYV, BYSV, CTV, LIYV, LChV, and GLRaV-3. To facilitate the alignment, only the C-terminal 250 amino acids of CP and CPd of LIYV, LChV, and GLRaV-3 were used. The scale beneath the phylogenetic tree represents the distance between sequences. Units indicate the number of substitution events.

FIG. 9 is an alignment of the amino acid sequence of HSP90 protein of GLRaV-2 with respect to other closteroviruses, BYS, BYSV, and CTV. The most conserved motifs (I to II) are indicated with the highlighted lines and marked with respective letters.

FIG. 10 is an alignment of the nucleotide sequence of 3'-terminal untranslated region of GLRaV-2 with respect to the closteroviruses BYV (Agranovsky et al., "Beet Yellows Closterovirus: Complete Genome Structure and Identification of a Papain-like Thiol Protease," Virology 198:311–24 (1994), which is hereby incorporated by reference), BYSV (Karasev et al., Organization of the 3'-Terminal Half of Beet Yellow Stunt Virus Genome and Implications for the Evolution of Closteroviruses," Virology 221:199–207 (1996), which is hereby incorporated by reference), and CTV (Karasev et al., "Complete Sequence of the Citrus Tristeza Virus RNA Genome," Virology 208:511–20 (1995), which is hereby incorporated by reference). The consensus sequences are shown, and the distance to the 3'-end is indicated. A complementary region capable of forming a "hair-pin" structure is underlined.

As shown in FIGS. 11A and 11B, the plant expression cassette (EPT8CP-GLRaV-2), which consists of a double cauliflower mosaic virus (CaMV) 35S-enhancer, a CaMV 35S-promoter, an alfalfa mosaic virus (ALMV) RNA4 5' leader sequence, a coat protein gene of GLRaV-2 (CP-GLRaV-2), and a CaMV 35S 3' untranslated region as a terminator, was cloned into the transformation vector by EcoR I restriction site. The CP of GLRaV-2 was cloned into the plant expression vector by Nco I restriction site.

DETAILED DESCRIPTION OF THE INVENTION

Figure 1A:
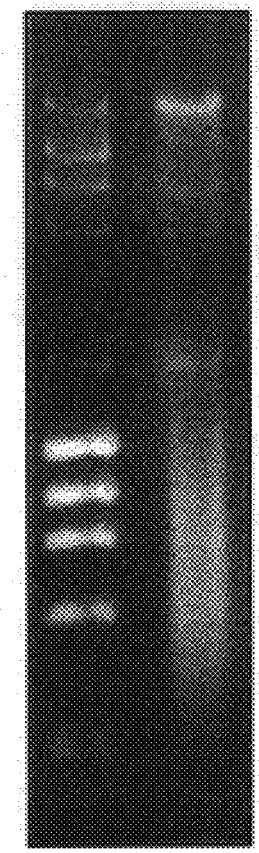
FIGS. 1A and 1B are a comparison of a double-stranded RNA (dsRNA) profile (FIG. 1A) of GLRaV-2 and its Northern hybridization analysis (FIG. 1B).

The present invention relates to isolated DNA molecules encoding for the proteins or polypeptides of a grapevine leafroll virus (type 2). A substantial portion of the grapevine leafroll virus (type-2) ("GLRaV-2") genome has been sequenced. Within the genome are a plurality of open reading frames ("ORFs") and a 3' untranscribed region ("UTR"), each containing DNA molecules in accordance with the present invention. The DNA molecule which constitutes a substantial portion of the GLRaV-2 genome comprises the nucleotide sequence corresponding to SEQ. ID. No. 1 as follows:

```
TAAACATTGC GAGAGAACCC CATTAGCGTC TCCGGGGTGA ACTTGGGAAG GTCTGCCGCC      60

AGCTCAGGTTA TTTATTTCGG CAGTTTCACG CAGCCCTTCG CGTTGTATCC GCGCCAAGAG    120

AGCGCGATCG TAAAAACGCA ACTTCCACCG GTCAGTGTAG TGAAGGTGGA GTGCGTAGCT    180

GCGGAGGTAG CTCCCGACAG GGGCGTGGTC GACAAGAAAC CTACGTCTGT TGGCGTTCCC    240

CCGCAGCGCG GTGTGCTTTC TTTTCCGACG GTGGTTCGGA ACCGCGGCGA CGTGATAATC    300

ACAGGGGTGG TGCATGAAGC CCTGAAGAAA ATTAAAGACG GGCTCTTACG CTTCCGCGTA    360

GGCGGTGACA TGCGTTTTTC GAGATTTTTC TCATCGAACT ACGGCTGCAG ATTCGTCGCG    420

AGCGTGCGTA CGAACACTAC AGTTTGGCTA AATTGCACGA AAGCGAGTGG TGAGAAATTC    480

TCACTCGCCG CCGCGTGCAC GGCGGATTAC GTGGCGATGC TGCGTTATGT GTGTGGCGGG    540

AAATTTCCAC TCGTCCTCAT GAGTAGAGTT ATTTACCCGG ATGGGCGCTG TTACTTGGCC    600

CATATGAGGT ATTTGTGCGC CTTTTACTGT CGCCCGTTTA GAGAGTCGGA TTATGCCCTC    660

GGAATGTGGC CTACGGTGGC GCGTCTCAGG GCATGCGTTG AGAAGAACTT CGGTGTCGAA    720

GCTTGTGGCA TAGCTCTTCG TGGCTATTAC ACCTCTCGCA ATGTTTATCA CTGTGATTAT    780

GACTCTGCTT ATGTAAAATA TTTTAGAAAC CTTTCCGGCC GCATTGGCGG TGGTTCGTTC    840

GATCCGACAT CTTTAACCTC CGTAATAACG GTGAAGATTA GCGGTCTTCC AGGTGGTCTT    900

CCTAAAAATA TAGCGTTTGG TGCCTTCCTG TGCGATATAC GTTACGTCGA ACCGGTAGAC    960

TCGGGCGGCA TTCAATCGAG CGTTAAGACG AAACGTGAAG ATGCGCACCG AACCGTAGAG   1020

GAACGGGCGG CCGGCGGATC CGTCGAGCAA CCGCGACAAA AGAGGATAGA TGAGAAAGGT   1080

TGCGGCAGAG TTCCTAGTGG AGGTTTTTCG CATCTCCTGG TCGGCAACCT TAACGAAGTT   1140

AGGAGGAAGG TAGCTGCCGG ACTTCTACGC TTTCGCGTTG GCGGTGATAT GGATTTTCAT   1200

CGCTCGTTCT CCACCCAAGC GGGCCACCGC TTGCTCCTGT GGCGCCGCTC GAGCCGGAGC   1260

GTGTGCCTTG AACTTTACTC ACCATCTAAA AACTTTTTGC GTTACGATGT CTTGCCCTGT   1320

TCTGGAGACT ATGCAGCGAT GTTTTCTTTC GCGGCGGGCG GCCGTTTCCC TTTAGTTTTG   1380

ATGACTAGAA TTAGATACCC GAACGGGTTT TGTTACTTGG CTCACTGCCG GTACGCGTGC   1440

GCGTTTCTCT TAAGGGGTTT TGATCCGAAG CGTTTCGACA TCGGTGCTTT CCCCACCGCG   1500

GCCAAGCTCA GAAACCGTAT GGTTTCGGAG CTTGGTGAAA GAAGTTTAGG TTTGAACTTG   1560

TACGGCGCAT ATACGTCACG CGGCGTCTTT CACTGCGATT ATGACGCTAA GTTTATAAAG   1620

GATTTGCGTC TTATGTCAGC AGTTATAGCT GGAAAGGACG GGGTGGAAGA GGTGGTACCT   1680

TCTGACATTA CTCCTGCCAT GAAGCAGAAA ACGATCGAAG CCGTGTATGA TAGATTATAT   1740

GGCGGCACTG ACTCGTTGCT GAAACTGAGC ATCGAGAAAG ACTTAATCGA TTTCAAAAAT   1800

GACGTGCAGA GTTTGAAGAA AGATCGGCCG ATTGTCAAAG TGCCCTTTTA CATGTCGGAA   1860

GCAACACAGA ATTCGCTGAC GCGTTTCTAC CCTCAGTTCG AACTTAAGTT TTCGCACTCC   1920

TCGCATTCAG ATCATCCCGC CGCCGCCGCT TCTACACTGC TGGAAAATGA AACGTTAGTG   1980

CGCTTATGTG GTAATAGCGT TTCAGATATT GGAGGTTGTC CTCTTTTCCA TTTGCATTCC   2040

AAGACGCAAA GACGGGTTCA CGTATGTAGG CCTGTGTTGG ATGGCAAGGA TGCGCAGCGT   2100

CGCGTGGTGC GTGATTTGCA GTATTCCAAC GTGCGTTTGG GAGACGATGA TAAAATTTTG   2160

GAAGGGCCAC GCAATATCGA CATTTGCCAC TATCCTCTGG GCGCGTGTGA CCACGAAAGT   2220

AGTGCTATGA TGATGGTGCA GGTGTATGAC GCGTCCCTTT ATGAGATATG TGGCGCCATG   2280
```

-continued

```
ATCAAGAAGA AAAGCCGCAT AACGTACTTA ACCATGGTCA CGCCCGGCGA GTTTCTTGAC      2340

GGACGCGAAT GCGTCTACAT GGAGTCGTTA GACTGTGAGA TTGAAGTTGA TGTGCACGCG      2400

GACGTCGTAA TGTACAAATT CGGTAGTTCT TGCTATTCGC ACAAGCTTTC AATCATCAAG      2460

GACATCATGA CCACTCCGTA CTTGACACTA GGTGGTTTTC TATTCAGCGT GGAGATGTAT      2520

GCGGTGCGTA TGGGCGTGAA TTACTTCAAG ATTACGAAGT CCGAAGTATC GCCTAGCATT      2580

AGCTGCACCA AGCTCCTGAG ATACCGAAGA GCTAATAGTG ACGTGGTTAA AGTTAAACTT      2640

CCACGTTTCG ATAAGAAACG TCGCATGTGT CTGCCTGGGT ATGACACCAT ATACCTAGAT      2700

TCGAAGTTTG TGAGTCGCGT TTTCGATTAT GTCGTGTGTA ATTGCTCTGC CGTGAACTCA      2760

AAAACTTTCG AGTGGGTGTG GAGTTTCATT AAGTCTAGTA AGTCGAGGGT GATTATTAGC      2820

GGTAAAATAA TTCACAAGGA TGTGAATTTG ACCTCAAGT ACGTCGAGAG TTTCGCCGCG      2880

GTTATGTTGG CCTCTGGCGT GCGCAGTAGA CTAGCGTCCG AGTACCTTGC TAAGAACCTT      2940

AGTCATTTTT CGGGAGATTG CTCCTTTATT GAAGCCACGT CTTTCGTGTT GCGTGAGAAA      3000

ATCAGAAACA TGACTCTGAA TTTTAACGAA AGACTTTTAC AGTTAGTGAA GCGCGTTGCC      3060

TTTGCGACCT TGGACGTGAG TTTTCTAGAT TTAGATTCAA CTCTTGAATC AATAACTGAT      3120

TTTGCCGAGT GTAAGGTAGC GATTGAACTC GACGAGTTGG GTTGCTTGAG AGCGGAGGCC      3180

GAGAATGAAA AAATCAGGAA TCTGGCGGGA GATTCGATTG CGGCTAAACT CGCGAGCGAG      3240

ATAGTGGTCG ATATTGACTC TAAGCCTTCA CCGAAGCAGG TGGGTAATTC GTCATCCGAA      3300

AACGCCGATA AGCGGGAAGT TCAGAGGCCC GGTTTGCGTG GTGGTTCTAG AAACGGGGTT      3360

GTTGGGGAGT TCCTTCACTT CGTCGTGGAT TCTGCCTTGC GTCTTTTCAA ATACGCGACG      3420

GATCAACAAC GGATCAAGTC TTACGTGCGT TTCTTGGACT CGGCGGTCTC ATTCTTGGAT      3480

TACAACTACG ATAATCTATC GTTTATACTG CGAGTGCTTT CGGAAGGTTA TTCGTGTATG      3540

TTCGCGTTTT TGGCGAATCG CGGCGACTTA TCTAGTCGTG TCCGTAGCGC GGTGTGTGCT      3600

GTGAAAGAAG TTGCTACCTC ATGCGCGAAC GCGAGCGTTT CTAAAGCCAA GGTTATGATT      3660

ACCTTCGCAG CGGCCGTGTG TGCTATGATG TTTAATAGCT GCGGTTTTTC AGGCGACGGT      3720

CGGGAGTATA AATCGTATAT ACATCGTTAC ACGCAAGTAT TGTTTGACAC TATCTTTTTT      3780

GAGGACAGCA GTTACCTACC CATAGAAGTT CTGAGTTCGG CGATATGCGG TGCTATCGTC      3840

ACACTTTTCT CCTCGGGCTC GTCCATAAGT TTAAACGCCT TCTTACTTCA AATTACCAAA      3900

GGATTCTCCC TAGAGGTTGT CGTCCGGAAT GTTGTGCGAG TCACGCATGG TTTGAGCACC      3960

ACAGCGACCG ACGGCGTCAT ACGTGGGGTT TTCTCCCAAA TTGTGTCTCA CTTACTTGTT      4020

GGAAATACGG GTAATGTGGC TTACCAGTCA GCTTTCATTG CCGGGGTGGT GCCTCTTTTA      4080

GTTAAAAAGT GTGTGAGCTT AATCTTCATC TTGCGTGAAG ATACTTATTC CGGTTTTATT      4140

AAGCACGGAA TCAGTGAATT CTCTTTCCTT AGTAGTATTC TGAAGTTCTT GAAGGGTAAG      4200

CTTGTGGACG AGTTGAAATC GATTATTCAA GGGGTTTTTG ATTCCAACAA GCACGTGTTT      4260

AAAGAAGCTA CTCAGGAAGC GATTCGTACG ACGGTCATGC AAGTGCCTGT CGCTGTAGTG      4320

GATGCCCTTA AGAGCGCCGC GGGAAAAATT TATAACAATT TTACTAGTCG ACGTACCTTT      4380

GGTAAGGATG AAGGCTCCTC TAGCGACGGC GCATGTGAAG AGTATTTCTC ATGCGACGAA      4440

GGTGAAGGTC CGGGTCTGAA AGGGGGTTCC AGCTATGGCT TCTCAATTTT AGCGTTCTTT      4500

TCACGCATTA TGTGGGGAGC TCGTCGGCTT ATTGTTAAGG TGAAGCATGA GTGTTTTGGG      4560

AAACTTTTTG AATTTCTATC GCTCAAGCTT CACGAATTCA GGACTCGCGT TTTTGGGAAG      4620

AATAGAACGG ACGTGGGAGT TTACGATTTT TTGCCCACGG GCATCGTGGA AACGCTCTCA      4680
```

-continued

```
TCGATAGAAG AGTGCGACCA AATTGAAGAA CTTCTCGGCG ACGACCTGAA AGGTGACAAG    4740

GATGCTTCGT TGACCGATAT GAATTACTTT GAGTTCTCAG AAGACTTCTT AGCCTCTATC    4800

GAGGAGCCGC CTTTCGCTGG ATTGCGAGGA GGTAGCAAGA ACATCGCGAT TTTGGCGATT    4860

TTGGAATACG CGCATAATTT GTTTCGCATT GTCGCAAGCA AGTGTTCGAA ACGACCTTTA    4920

TTTCTTGCTT TCGCCGAACT CTCAAGCGCC CTTATCGAGA AATTTAAGGA GGTTTTCCCT    4980

CGTAAGAGCC AGCTCGTCGC TATCGTGCGC GAGTATACTC AGAGATTCCT CCGAAGTCGC    5040

ATGCGTGCGT TGGGTTTGAA TAACGAGTTC GTGGTAAAAT CTTTCGCCGA TTTGCTACCC    5100

GCATTAATGA AGCGGAAGGT TTCAGGTTCG TTCTTAGCTA GTGTTTATCG CCCACTTAGA    5160

GGTTTCTCAT ATATGTGTGT TTCAGCGGAG CGACGTGAAA AGTTTTTTGC TCTCGTGTGT    5220

TTAATCGGGT TAAGTCTCCC TTTCTTCGTG CGCATCGTAG GAGCGAAAGC GTGCGAAGAA    5280

CTCGTGTCCT CAGCGCGTCG CTTTTATGAG CGTATTAAAA TTTTTCTAAG GCAGAAGTAT    5340

GTCTCTCTTT CTAATTTCTT TTGTCACTTG TTTAGCTCTG ACGTTGATGA CAGTTCCGCA    5400

TCTGCAGGGT TGAAAGGTGG TGCGTCGCGA ATGACGCTCT TCCACCTTCT GGTTCGCCTT    5460

GCTAGTGCCC TCCTATCGTT AGGGTGGGAA GGGTTAAAGC TACTCTTATC GCACCACAAC    5520

TTGTTATTTT TGTGTTTTGC ATTGGTTGAC GATGTGAACG TCCTTATCAA AGTTCTTGGG    5580

GGTCTTTCTT TCTTTGTGCA ACCAATCTTT TCCTTGTTTG CGGCGATGCT TCTACAACCG    5640

GACAGGTTTG TGGAGTATTC CGAGAAACTT GTTACAGCGT TTGAATTTTT CTTAAAATGT    5700

TCGCCTCGCG CGCCTGCACT ACTCAAAGGG TTTTTTGAGT GCGTGGCGAA CAGCACTGTG    5760

TCAAAAACCG TTCGAAGACT TCTTCGCTGT TTCGTGAAGA TGCTCAAACT TCGAAAAGGG    5820

CGAGGGTTGC GTGCGGATGG TAGGGGTCTC CATCGGCAGA AAGCCGTACC CGTCATACCT    5880

TCTAATCGGG TCGTGACCGA CGGGGTTGAA AGACTTTCGG TAAAGATGCA AGGAGTTGAA    5940

GCGTTGCGTA CCGAATTGAG AATCTTAGAA GATTTAGATT CTGCCGTGAT CGAAAAACTC    6000

AATAGACGCA GAAATCGTGA CACTAATGAC GACGAATTTA CGCGCCCTGC TCATGAGCAG    6060

ATGCAAGAAG TCACCACTTT CTGTTCGAAA GCCAACTCTG CTGGTTTGGC CCTGGAAAGG    6120

GCAGTGCTTG TGGAAGACGC TATAAAGTCG GAGAAACTTT CTAAGACGGT TAATGAGATG    6180

GTGAGGAAAG GGAGTACCAC CAGCGAAGAA GTGGCCGTCG CTTTGTCGGA CGATGAAGCC    6240

GTGGAAGAAA TCTCTGTTGC TGACGAGCGA GACGATTCGC CTAAGACAGT CAGGATAAGC    6300

GAATACCTAA ATAGGTTAAA CTCAAGCTTC GAATTCCCGA AGCCTATTGT TGTGGACGAC    6360

AACAAGGATA CCGGGGGTCT AACGAACGCC GTGAGGGAGT TTTATTATAT GCAAGAACTT    6420

GCTCTTTTCG AAATCCACAG CAAACTGTGC ACCTACTACG ATCAACTGCG CATAGTCCAC    6480

TTCGATCGTT CCGTAGCACC ATGCAGCGAA GATGCTCAGC TGTACGTACG GAAGAACGGC    6540

TCAACGATAG TGCAGGGTAA AGAGGTACGT TTGCACATTA AGGATTTCCA CGATCACGAT    6600

TTCCTGTTTC ACGGAAAAAT TTCTATTAAC AAGCGGCGGC GAGGCGGAAA TGTTTTATAT    6660

CACGACAACC TCGCGTTCTT GGCGAGTAAT TTGTTCTTAG CCGGCTACCC CTTTTCAAGG    6720

AGCTTCGTCT TCACGAATTC GTCGGTCGAT ATTCTCCTCT ACGAAGCTCC ACCCGGAGGT    6780

GGTAAGACGA CGACGCTGAT TGACTCGTTC TTGAAGGTCT TCAAGAAAGG TGAGGTTTCC    6840

ACCATGATCT TAACCGCCAA CAAAAGTTCG CAGGTTGAGA TCCTAAAGAA AGTGGAGAAG    6900

GAAGTGTCTA ACATTGAATG CCAGAAACGT AAAGACAAAA GATCTCCGAA AAAGAGCATT    6960

TACACCATCG ACGCTTATTT AATGCATCAC CGTGGTTGTG ATGCAGACGT TCTTTTCATC    7020

GATGAGTGTT TCATGGTTCA TGCGGGTAGC GTACTAGCTT GCATTGAGTT CACGAGGTGT    7080
```

-continued

```
CATAAAGTAA TGATCTTCGG GGATAGCCGG CAGATTCACT ACATTGAAAG GAACGAATTG     7140

GACAAGTGTT TGTATGGGGA TCTCGACAGG TTCGTGGACC TGCAGTGTCG GGTTTATGGT     7200

AATATTTCGT ACCGTTGTCC ATGGGATGTG TGCGCTTGGT TAAGCACAGT GTATGGCAAC     7260

CTAATCGCCA CCGTGAAGGG TGAAAGCGAA GGTAAGAGCA GCATGCGCAT TAACGAAATT     7320

AATTCAGTCG ACGATTAGT CCCCGACGTG GGTTCCACGT TTCTGTGTAT GCTTCAGTCG      7380

GAGAAGTTGG AAATCAGCAA GCACTTTATT CGCAAGGGTT TGACTAAACT TAACGTTCTA    7440

ACGGTGCATG AGGCGCAAGG TGAGACGTAT GCGCGTGTGA ACCTTGTGCG ACTTAAGTTT    7500

CAGGAGGATG AACCCTTTAA ATCTATCAGG CACATAACCG TCGCTCTTTC TCGTCACACC    7560

GACAGCTTAA CTTATAACGT CTTAGCTGCT CGTCGAGGTG ACGCCACTTG CGATGCCATC    7620

CAGAAGGCTG CGGAATTGGT GAACAAGTTT CGCGTTTTTC CTACATCTTT TGGTGGTAGT    7680

GTTATCAATC TCAACGTGAA GAAGGACGTG GAAGATAACA GTAGGTGCAA GGCTTCGTCG    7740

GCACCATTGA GCGTAATCAA CGACTTTTTG AACGAAGTTA ATCCCGGTAC TGCGGTGATT    7800

GATTTTGGTG ATTTGTCCGC GGACTTCAGT ACTGGGCCTT TTGAGTGCGG TGCCAGCGGT    7860

ATTGTGGTGC GGGACAACAT CTCCTCCAGC AACATCACTG ATCACGATAA GCAGCGTGTT    7920

TAGCGTAGTT CGGTCGCAGG CGATTCCGCG TAGAAAACCT TCTCTACAAG AAAATTTGTA    7980

TTCGTTTGAA GCGCGGAATT ATAACTTCTC GACTTGCGAC CGTAACACAT CTGCTTCAAT    8040

GTTCGGAGAG GCTATGGCGA TGAACTGTCT TCGTCGTTGC TTCGACCTAG ATGCCTTTTC    8100

GTCCCTGCGT GATGATGTGA TTAGTATCAC ACGTTCAGGC ATCGAACAAT GGCTGGAGAA    8160

ACGTACTCCT AGTCAGATTA AAGCATTAAT GAAGGATGTT GAATCGCCTT TGGAAATTGA    8220

CGATGAAATT TGTCGTTTTA AGTTGATGGT GAAGCGTGAC GCTAAGGTGA AGTTAGACTC    8280

TTCTTGTTTA ACTAAACACA GCGCCGCTCA AAATATCATG TTTCATCGCA AGAGCATTAA    8340

TGCTATCTTC TCTCCTATCT TTAATGAGGT GAAAAACCGA ATAATGTGCT GTCTTAAGCC    8400

TAACATAAAG TTTTTTACGG AGATGACTAA CAGGGATTTT GCTTCTGTTG TCAGCAACAT    8460

GCTTGGTGAC GACGATGTGT ACCATATAGG TGAAGTTGAT TTCTCAAAGT ACGACAAGTC    8520

TCAAGATGCT TTCGTGAAGG CTTTTGAAGA AGTAATGTAT AAGGAACTCG GTGTTGATGA    8580

AGAGTTGCTG GCTATCTGGA TGTGCGGCGA GCGGTTATCG ATAGCTAACA CTCTCGATGG    8640

TCAGTTGTCC TTCACGATCG AGAATCAAAG GAAGTCGGGA GCTTCGAACA CTTGGATTGG    8700

TAACTCTCTC GTCACTTTGG GTATTTTAAG TCTTTACTAC GACGTTAGAA ATTTCGAGGC    8760

GTTGTACATC TCGGGCGATG ATTCTTTAAT TTTTTCTCGC AGCGAGATTT CGAATTATGC    8820

CGACGACATA TGCACTGACA TGGGTTTTGA GACAAAATTT ATGTCCCCAA GTGTCCCGTA    8880

CTTTTGTTCT AAATTTGTTG TTATGTGTGG TCATAAGACG TTTTTTGTTC CCGACCCGTA    8940

CAAGCTTTTT GTCAAGTTGG GAGCAGTCAA AGAGGATGTT TCAATGGATT TCCTTTTCGA    9000

GACTTTTACC TCCTTTAAAG ACTTAACCTC CGATTTTAAC GACGAGCGCT TAATTCAAAA    9060

GCTCGCTGAA CTTGTGGCTT TAAAATATGA GGTTCAAACC GGCAACACCA CCTTGGCGTT    9120

AAGTGTGATA CATTGTTTGC GTTCGAATTT CCTCTCGTTT AGCAAGTTAT ATCCTCGCGT    9180

GAAGGGATGG CAGGTTTTTT ACACGTCGGT TAAGAAAGCG CTTCTCAAGA GTGGGTGTTC    9240

TCTCTTCGAC AGTTTCATGA CCCCTTTTGG TCAGGCTGTC ATGGTTTGGG ATGATGAGTA    9300

GCGCTAACTT GTGCGCAGTT TCTTTGTTCG TGACATACAC CTTGTGTGTC ACCGTGCGTT    9360

TATAATGAAT CAGGTTTTGC AGTTTGAATG TTTGTTTCTG CTGAATCTCG CGGTTTTTGC    9420

TGTGACTTTC ATTTTCATTC TTCTGGTCTT CCGCGTGATT AAGTCTTTTC GCCAGAAGGG    9480
```

-continued

```
TCACGAAGCA CCTGTTCCCG TTGTTCGTGG CGGGGGTTTT TCAACCGTAG TGTAGTCAAA      9540

AGACGCGCAT ATGGTAGTTT TCGGTTTGGA CTTTGGCACC ACATTCTCTA CGGTGTGTGT      9600

GTACAAGGAT GGACGAGTTT TTTCATTCAA GCAGAATAAT TCGGCGTACA TCCCCACTTA      9660

CCTCTATCTC TTCTCCGATT CTAACCACAT GACTTTTGGT TACGAGGCCG AATCACTGAT      9720

GAGTAATCTG AAAGTTAAAG GTTCGTTTTA TAGAGATTTA AAACGTTGGG TGGGTTGCGA      9780

TTCGAGTAAC CTCGACGCGT ACCTTGACCG TTTAAAACCT CATTACTCGG TCCGCTTGGT      9840

TAAGATCGGC TCTGGCTTGA ACGAAACTGT TTCAATTGGA AACTTCGGGG GCACTGTTAA      9900

GTCTGAGGCT CATCTGCCAG GGTTGATAGC TGTGTTTATT AAGGCTGTCA TTAGTTGCGC      9960

GGAGGGCGCG TTTGCGTGCA CTTGCACCGG GGTTATTTGT TCAGTACCTG CCAATTATGA     10020

TAGCGTTCAA AGGAATTTCA CTGATCAGTG TGTTTCACTC AGCGGTTATC AGTGCGTATA     10080

TATGATCAAT GAACCTTCAG CGGCTGCGCT ATCTGCGTGT AATTCGATTG GAAAGAAGTC     10140

CGCAAATTTG GCTGTTTACG ATTTCGGTGG TGGGACCTTC GACGTGTCTA TCATTTCATA     10200

CCGCAACAAT ACTTTTGTTG TGCGAGCTTC TGGAGGCGAT CTAAATCTCG GTGGAAGGGA     10260

TGTTGATCGT GCGTTTCTCA CGCACCTCTT CTCTTTAACA TCGCTGGAAC CTGACCTCAC     10320

TTTGGATATC TCGAATCTGA AGAATCTTT  ATCAAAAACG GACGCAGAGA TAGTTTACAC     10380

TTTGAGAGGT GTCGATGGAA GAAAAGAAGA CGTTAGAGTA AACAAAAACA TTCTTACGTC     10440

GGTGATGCTC CCCTACGTGA ACAGAACGCT TAAGATATTA GAGTCAACCT TAAAATCGTA     10500

TGCTAAGAGT TAGAATGAGA GTGCGCGAGT TAAGTGCGAT TTAGTGCTGA TAGGAGGATC     10560

TTCATATCTT CCTGGCCTGG CAGACGTACT AACGAAGCAT CAGAGCGTTG ATCGTATCTT     10620

AAGAGTTTCG GATCCTCGGG CTGCCGTGGC CGTCGGTTGC GCATTATATT CTTCATGCCT     10680

CTCAGGATCT GGGGGGTTGC TACTGATCGA CTGTGCAGCT CACACTGTCG CTATAGCGGA     10740

CAGAAGTTGT CATCAAATCA TTTGCGCTCC AGCGGGGGCA CCGATCCCCT TTTCAGGAAG     10800

CATGCCTTTG TACTTAGCCA GGGTCAACAA GAACTCGCAG CGTGAAGTCG CCGTGTTTGA     10860

AGGGGAGTAC GTTAAGTGCC CTAAGAACAG AAAGATCTGT GGAGCAAATA TAAGATTTTT     10920

TGATATAGGA GTGACGGGTG ATTCGTACGC ACCCGTTACC TTCTATATGG ATTTCTCCAT     10980

TTCAAGCGTA GGAGCCGTTT CATTCGTGGT GAGAGGTCCT GAGGGTAAGC AAGTGTCACT     11040

CACTGGAACT CCAGCGTATA ACTTTTCGTC TGTGGCTCTC GGATCACGCA GTGTCCGAGA     11100

ATTGCATATT AGTTTAAATA ATAAAGTTTT TCTCGGTTTG CTTCTACATA GAAAGGCGGA     11160

TCGACGAATA CTTTTCACTA AGGATGAAGC GATTCGATAC GCCGATTCAA TTGATATCGC     11220

GGATGTGCTA AAGGAATATA AAAGTTACGC GGCCACTGCC TTACCACCAG ACGAGGATGT     11280

CGAATTACTC CTGGGAAAGT CTGTTCAAAA AGTTTTACGG GGAAGCAGAC TGGAAGAAAT     11340

ACCTCTCTAG GAGCATAGCA GCACACTCAA GTGAAATTAA AACTCTACCA GACATTCGAT     11400

TGTACGGCGG TAGGGTTGTA AAGAAGTCCG AATTCGAATC AGCACTTCCT AATTCTTTTG     11460

AACAGGAATT AGGACTGTTC ATACTGAGCG AACGGAAGT  GGGATGGAGC AAATTATGCG     11520

GAATAACGGT GGAAGAAGCA GCATACGATC TTACGAATCC CAAGGCTTAT AAATTCACTG     11580

CCGAGACATG TAGCCCGGAT GTAAAAGGTG AAGGACAAAA ATACTCTATG GAAGACGTGA     11640

TGAATTTCAT GCGTTTATCA AATCTGGATG TTAACGACAA GATGCTGACG GAACAGTGTT     11700

GGTCGCTGTC CAATTCATGC GGTGAATTGA TCAACCCAGA CGACAAAGGG CGATTCGTGG     11760

CTCTCACCTT TAAGGACAGA GACACAGCTG ATGACACGGG TGCCGCCAAC GTGGAATGTC     11820

GCGTGGGCGA CTATCTAGTT TACGCTATGT CCCTGTTTGA GCAGAGGACC CAAAAATCGC     11880
```

-continued

```
AGTCTGGCAA CATCTCTCTG TACGAAAAGT ACTGTGAATA CATCAGGACC TACTTAGGGA     11940
GTACAGACCT GTTCTTCACA GCGCCGGACA GGATTCCGTT ACTTACGGGC ATCCTATACG     12000
ATTTTTGTAA GGAATACAAC GTTTTCTACT CGTCATATAA GAGAAACGTC GATAATTTCA     12060
GATTCTTCTT GGCGAATTAT ATGCCTTTGA TATCTGACGT CTTTGTCTTC CAGTGGGTAA     12120
AACCCGCGCC GGATGTTCGG CTGCTTTTTG AGTTAAGTGC AGCGGAACTA ACGCTGGAGG     12180
TTCCCACACT GAGTTTGATA GATTCTCAAG TTGTGGTAGG TCATATCTTA AGATACGTAG     12240
AATCCTACAC ATCAGATCCA GCCATCGACG CGTTAGAAGA CAAACTGGAA GCGATACTGA     12300
AAAGTAGCAA TCCCCGTCTA TCGACAGCGC AACTATGGGT TGGTTTCTTT TGTTACTATG     12360
GTGAGTTTCG TACGGCTCAA AGTAGAGTAG TGCAAAGACC AGGCGTATAC AAAACACCTG     12420
ACTCAGTGGG TGGATTTGAA ATAAACATGA AAGATGTTGA GAAATTCTTC GATAAACTTC     12480
AGAGAGAATT GCCTAATGTA TCTTTGCGGC GTCAGTTTAA CGGAGCTAGA GCGCATGAGG     12540
CTTTCAAAAT ATTTAAAAAC GGAAATATAA GTTTCAGACC TATATCGCGT TTAAACGTGC     12600
CTAGAGAGTT CTGGTATCTG AACATAGACT ACTTCAGGCA CGCGAATAGG TCCGGGTTAA     12660
CCGAAGAAGA AATACTCATC CTAAACAACA TAAGCGTTGA TGTTAGGAAG TTATGCGCTG     12720
AGAGAGCGTG CAATACCCTA CCTAGCGCGA AGCGCTTTAG TAAAAATCAT AAGAGTAATA     12780
TACAATCATC ACGCCAAGAG CGGAGGATTA AAGACCCATT GGTAGTCCTG AAAGACACTT     12840
TATATGAGTT CCAACACAAG CGTGCCGGTT GGGGGTCTCG AAGCACTCGA GACCTCGGGA     12900
GTCGTGCTGA CCACGCGAAA GGAAGCGGTT GATAAGTTTT TTAATGAACT AAAAAACGAA     12960
AATTACTCAT CAGTTGACAG CAGCCGATTA AGCGATTCGG AAGTAAAAGA AGTGTTAGAG     13020
AAAAGTAAAG AAAGTTTCAA AAGCGAACTG GCCTCCACTG ACGAGCACTT CGTCTACCAC     13080
ATTATATTTT TCTTAATCCG ATGTGCTAAG ATATCGACAA GTGAAAAGGT GAAGTACGTT     13140
GGTAGTCATA CGTACGTGGT CGACGGAAAA ACGTACACCG TTCTTGACGC TTGGGTATTC     13200
AACATGATGA AAAGTCTCAC GAAGAAGTAC AAACGAGTGA ATGGTCTGCG TGCGTTCTGT     13260
TGCGCGTGCG AAGATCTATA TCTAACCGTC GCACCAATAA TGTCAGAACG CTTTAAGACT     13320
AAAGCCGTAG GGATGAAAGG TTTGCCTGTT GGAAAGGAAT ACTTAGGCGC CGACTTTCTT     13380
TCGGAACTA GCAAACTGAT GAGCGATCAC GACAGGGCGG TCTCCATCGT TGCAGCGAAA      13440
AACGCTGTCG ATCGTAGCGC TTTCACGGGT GGGGAGAGAA AGATAGTTAG TTTGTATGAT     13500
CTAGGGAGGT ACTAAGCACG GTGTGCTATA GTGCGTGCTA TAATAATAAA CACTAGTGCT     13560
TAAGTCGCGC AGAAGAAAAC GCTATGGAGT TGATGTCCGA CAGCAACCTT AGCAACCTGG     13620
TGATAACCGA CGCCTCTAGT CTAAATGGTG TCGACAAGAA GCTTTTATCT GCTGAAGTTG     13680
AAAAAATGTT GGTGCAGAAA GGGGCTCCTA ACGAGGGTAT AGAAGTGGTG TTCGGTCTAC     13740
TCCTTTACGC ACTCGCGGCA AGAACCACGT CTCCTAAGGT TCAGCGCGCA GATTCAGACG     13800
TTATATTTTC AAATAGTTTC GGAGAGAGGA ATGTGGTAGT AACAGAGGGT GACCTTAAGA     13860
AGGTACTCGA CGGGTGTGCG CCTCTCACTA GGTTCACTAA TAAACTTAGA ACGTTCGGTC     13920
GTACTTTCAC TGAGGCTTAC GTTGACTTTT GTATCGCGTA TAAGCACAAA TTACCCCAAC     13980
TCAACGCCGC GGCGGAATTG GGGATTCCAG CTGAAGATTC GTACTTAGCT GCAGATTTTC     14040
TGGGTACTTG CCCGAAGCTC TCTGAATTAC AGCAAAGTAG GAAGATGTTC GCGAGTATGT     14100
ACGCTCTAAA AACTGAAGGT GGAGTGGTAA ATACACCAGT GAGCAATCTG CGTCAGCTAG     14160
GTAGAAGGGA AGTTATGTAA TGGAAGATTA CGAAGAAAAA TCCGAATCGC TCATACTGCT     14220
ACGCACGAAT CTGAACACTA TGCTTTTAGT GGTCAAGTCC GATGCTAGTG TAGAGCTGCC     14280
```

```
TAAACTACTA ATTTGCGGTT ACTTACGAGT GTCAGGACGT GGGGAGGTGA CGTGTTGCAA    14340

CCGTGAGGAA TTAACAAGAG ATTTTGAGGG CAATCATCAT ACGGTGATCC GTTCTAGAAT    14400

CATACAATAT GACAGCGAGT CTGCTTTTGA GGAATTCAAC AACTCTGATT GCGTAGTGAA    14460

GTTTTTCCTA GAGACTGGTA GTGTCTTTTG GTTTTTCCTT CGAAGTGAAA CCAAAGGTAG    14520

AGCGGTGCGA CATTTGCGCA CCTTCTTCGA AGCTAACAAT TTCTTCTTTG GATCGCATTG    14580

CGGTACCATG GAGTATTGTT TGAAGCAGGT ACTAACTGGA ACTGAATCTA TAATCGATTC    14640

TTTTTGCGAA GAAAGAAATC GTTAAGATGA GGGTTATAGT GTCTCCTTAT GAAGCTGAAG    14700

ACATTCTGAA AAGATCGACT GACATGTTAC GAAACATAGA CAGTGGGGTC TTGAGCACTA    14760

AAGAATGTAT CAAGGCATTC TCGACGATAA CGCGAGACCT ACATTGTGCG AAGGCTTCCT    14820

ACCAGTGGGG TGTTGACACT GGGTTATATC AGCGTAATTG CGCTGAAAAA CGTTTAATTG    14880

ACACGGTGGA GTCAAACATA CGGTTGGCTC AACCTCTCGT GCGTGAAAAA GTGGCGGTTC    14940

ATTTTTGTAA GGATGAACCA AAAGAGCTAG TAGCATTCAT CACGCGAAAG TACGTGGAAC    15000

TCACGGGCGT GGGAGTGAGA GAAGCGGTGA AGAGGGAAAT GCGCTCTCTT ACCAAAACAG    15060

TTTTAAATAA AATGTCTTTG GAAATGGCGT TTTACATGTC ACCACGAGCG TGGAAAAACG    15120

CTGAATGGTT AGAACTAAAA TTTTCACCTG TGAAAATCTT TAGAGATCTG CTATTAGACG    15180

TGGAAACGCT CAACGAATTG TGCGCCGAAG ATGATGTTCA CGTCGACAAA GTAAATGAGA    15240

ATGGGGACGA AAATCACGAC CTCGAACTCC AAGACGAATG TTAAACATTG GTTAAGTTTA    15300

ACGAAAATGA TTAGTAAATA ATAAATCGAA CGTGGGTGTA TCTACCTGAC GTATCAACTT    15360

AAGCTGTTAC TGAGTAATTA AACCAACAAG TGTTGGTGTA ATGTGTATGT TGATGTAGAG    15420

AAAAATCCGT TTGTAGAACG GTGTTTTTCT CTTCTTTATT TTTAAAAAAA AAATAAAAAA    15480

AAAAAAAAAA AAGCGGCCGC                                                15500
```

Another DNA molecule of the present invention (GLRaV-2 ORF1a) includes nucleotides 4–7923 of SEQ. ID. No. 1 and is believed to code for a large, grapevine leafroll virus polyprotein containing the conserved domains characteristic of two papain-like proteases, a methyltransferase, and a helicase. This DNA molecule comprises the nucleotide sequence corresponding to SEQ. ID. No. 2 as follows:

```
ACATTGCGAG AGAACCCCAT TAGCGTCTCC GGGGTGAACT TGGGAAGGTC TGCCGCCGCT     60

CAGGTTATTT ATTTCGGCAG TTTCACGCAG CCCTTCGCGT TGTATCCGCG CCAAGAGAGC    120

GCGATCGTAA AAACGCAACT TCCACCGGTC AGTGTAGTGA AGGTGGAGTG CGTAGCTGCG    180

GAGGTAGCTC CCGACAGGGG CGTGGTCGAC AAGAAACCTA CGTCTGTTGG CGTTCCCCCG    240

CAGCGCGGTG TGCTTTCTTT TCCGACGGTG GTTCGGAACC GCGGCGACGT GATAATCACA    300

GGGGTGGTGC ATGAAGCCCT GAAGAAAATT AAAGACGGGC TCTTACGCTT CCGCGTAGGC    360

GGTGACATGC GTTTTCGAG ATTTTTCTCA TCGAACTACG GCTGCAGATT CGTCGCGAGC     420

GTGCGTACGA ACACTACAGT TTGGCTAAAT TGCACGAAAG CGAGTGGTGA GAAATTCTCA    480

CTCGCCGCCG CGTGCACGGC GGATTACGTG GCGATGCTGC GTTATGTGTG TGGCGGGAAA    540

TTTCCACTCG TCCTCATGAG TAGAGTTATT TACCCGGATG GGCGCTGTTA CTTGGCCCAT    600

ATGAGGTATT TGTGCGCCTT TTACTGTCGC CCGTTTAGAG AGTCGGATTA TGCCCTCGGA    660

ATGTGGCCTA CGGTGGCGCG TCTCAGGGCA TGCGTTGAGA AGAACTTCGG TGTCGAAGCT    720

TGTGGCATAG CTCTTCGTGG CTATTACACC TCTCGCAATG TTTATCACTG TGATTATGAC    780

TCTGCTTATG TAAAATATTT TAGAAACCTT TCCGGCCGCA TTGGCGGTGG TTCGTTCGAT    840

CCGACATCTT TAACCTCCGT AATAACGGTG AAGATTAGCG GTCTTCCAGG TGGTCTTCCT    900
```

-continued

```
AAAAATATAG CGTTTGGTGC CTTCCTGTGC GATATACGTT ACGTCGAACC GGTAGACTCG      960
GGCGGCATTC AATCGAGCGT TAAGACGAAA CGTGAAGATG CGCACCGAAC CGTAGAGGAA     1020
CGGGCGGCCG GCGGATCCGT CGAGCAACCG CGACAAAAGA GGATAGATGA GAAAGGTTGC     1080
GGCAGAGTTC CTAGTGGAGG TTTTTCGCAT CTCCTGGTCG GCAACCTTAA CGAAGTTAGG     1140
AGGAAGGTAG CTGCCGGACT TCTACGCTTT CGCGTTGGCG GTGATATGGA TTTTCATCGC     1200
TCGTTCTCCA CCCAAGCGGG CCACCGCTTG CTGGTGTGGC GCCGCTCGAG CCGGAGCGTG     1260
TGCCTTGAAC TTTACTCACC ATCTAAAAAC TTTTTGCGTT ACGATGTCTT GCCCTGTTCT     1320
GGAGACTATG CAGCGATGTT TTCTTTCGCG GCGGGCGGCC GTTTCCCTTT AGTTTTGATG     1380
ACTAGAATTA GATACCCGAA CGGGTTTTGT TACTTGGCTC ACTGCCGGTA CGCGTGCGCG     1440
TTTCTCTTAA GGGGTTTTGA TCCGAAGCGT TTCGACATCG GTGCTTTCCC CACCGCGGCC     1500
AAGCTCAGAA ACCGTATGGT TTCGGAGCTT GGTGAAAGAA GTTAGGTTT GAACTTGTAC     1560
GGCGCATATA CGTCACGCGG CGTCTTTCAC TGCGATTATG ACGCTAAGTT TATAAAGGAT     1620
TTGCGTCTTA TGTCAGCAGT TATAGCTGGA AAGGACGGGG TGGAAGAGGT GGTACCTTCT     1680
GACATAACTC CTGCCATGAA GCAGAAAACG ATCGAAGCCG TGTATGATAG ATTATATGGC     1740
GGCACTGACT CGTTGCTGAA ACTGAGCATC GAGAAAGACT TAATCGATTT CAAAAATGAC     1800
GTGCAGAGTT TGAAGAAAGA TCGGCCGATT GTCAAAGTGC CCTTTTACAT GTCGGAAGCA     1860
ACACAGAATT CGCTGACGCG TTTCTACCCT CAGTTCGAAC TTAAGTTTTC GCACTCCTCG     1920
CATTCAGATC ATCCCGCCGC CGCCGCTTCT AGACTGCTGG AAAATGAAAC GTTAGTGCGC     1980
TTATGTGGTA ATAGCGTTTC AGATATTGGA GGTTGTCCTC TTTTCCATTT GCATTCCAAG     2040
ACGCAAAGAC GGGTTCACGT ATGTAGGCCT GTGTTGGATG GCAAGGATGC GCAGCGTCGC     2100
GTGGTGCGTG ATTTGCAGTA TTCCAACGTG CGTTTGGGAG ACGATGATAA AATTTTGGAA     2160
GGGCCACGCA ATATCGACAT TTGCCACTAT CCTCTGGGCG CGTGTGACCA CGAAAGTAGT     2220
GCTATGATGA TGGTGCAGGT GTATGACGCG TCCCTTTATG AGATATGTGG CGCCATGATC     2280
AAGAAGAAAA GCCGCATAAC GTACTTAACC ATGGTCACGC CCGGCGAGTT TCTTGACGGA     2340
CGCGAATGCG TCTACATGGA GTCGTTAGAC TGTGAGATTG AAGTTGATGT GCACGCGGAC     2400
GTCGTAATGT ACAAATTCGG TAGTTCTTGC TATTCGCACA AGCTTTCAAT CATCAAGGAC     2460
ATCATGACCA CTCCGTACTT GACACTAGGT GGTTTTCTAT TCAGCGTGGA GATGTATGAG     2520
GTGCGTATGG GCGTGAATTA CTTCAAGATT ACGAAGTCCG AAGTATCGCC TAGCATTAGC     2580
TGCACCAAGC TCCTGAGATA CCGAAGAGCT AATAGTGACG TGGTTAAAGT TAAACTTCCA     2640
CGTTTCGATA AGAAACGTCG CATGTGTCTG CCTGGGTATG ACACCATATA CCTAGATTCG     2700
AAGTTTGTGA GTCGCGTTTT CGATTATGTC GTGTGTAATT GCTCTGCCGT GAACTCAAAA     2760
ACTTTCGAGT GGGTGTGGAG TTTCATTAAG TCTAGTAAGT CGAGGGTGAT TATTAGCGGT     2820
AAAATAATTC ACAAGGATGT GAATTTGGAC CTCAAGTACG TCGAGAGTTT CGCCGCGGTT     2880
ATGTTGGCCT CTGGCGTGCG CAGTAGACTA GCGTCCGAGT ACCTTGCTAA GAACCTTAGT     2940
CATTTTTCGG GAGATTGCTC CTTTATTGAA GCCACGTCTT TCGTGTTGCG TGAGAAAATC     3000
AGAAACATGA CTCTGAATTT TAACGAAAGA CTTTTACAGT TAGTGAAGCG CGTTGCCTTT     3060
GCGACCTTGG ACGTGAGTTT TCTAGATTTA GATTCAACTC TTGAATCAAT AACTGATTTT     3120
GCCGAGTGTA AGGTAGCGAT TGAACTCGAC GAGTTGGGTT GCTTGAGAGC GGAGGCCGAG     3180
AATGAAAAAA TCAGGAATCT GGCGGGAGAT TCGATTGCGG CTAAACTCGC GAGCGAGATA     3240
GTGGTCGATA TTGACTCTAA GCCTTCACCG AAGCAGGTGG GTAATTCGTC ATCCGAAAAC     3300
```

-continued

```
GCCGATAAGC GGGAAGTTCA GAGGCCCGGT TTGCGTGGTG GTTCTAGAAA CGGGGTTGTT    3360

GGGGAGTTCC TTCACTTCGT CGTGGATTCT GCCTTGCGTC TTTTCAAATA CGCGACGGAT    3420

CAACAACGGA TCAAGTCTTA CGTGCGTTTC TTGGACTCGG CGGTCTCATT CTTGGATTAC    3480

AACTACGATA ATCTATCGTT TATACTGCGA GTGCTTTCGG AAGGTTATTC GTGTATGTTC    3540

GCGTTTTTGG CGAATCGCGG CGACTTATCT AGTCGTGTCC GTAGCGCGGT GTGTGCTGTG    3600

AAAGAAGTTG CTACCTCATG CGCGAACGCG AGCGTTTCTA AAGCCAAGGT TATGATTACC    3660

TTCGCAGCGG CCGTGTGTGC TATGATGTTT AATAGCTGCG GTTTTTCAGG CGACGGTCGG    3720

GAGTATAAAT CGTATATACA TCGTTACACG CAAGTATTGT TTGACACTAT CTTTTTGTAG    3780

GACAGCAGTT ACCTACCCAT AGAAGTTCTG AGTTCGGCGA TATGCGGTGC TATCGTCACA    3840

CTTTTCTCCT CGGGCTCGTC CATAAGTTTA AACGCCTTCT TACTTCAAAT TACCAAAGGA    3900

TTCTCCCTAG AGGTTGTCGT CCGGAATGTT GTGCGAGTCA CGCATGGTTT GAGCACCACA    3960

GCGACCGACG GCGTCATACG TGGGGTTTTC TCCCAAATTG TGTCTCACTT ACTTGTTGGA    4020

AATACGGGTA ATGTGGCTTA CCAGTCAGCT TTCATTGCCG GGGTGGTGCC TCTTTTAGTT    4080

AAAAAGTGTG TGAGCTTAAT CTTCATCTTG CGTGAAGATA CTTATTCCGG TTTTATTAAG    4140

CACGGAATCA GTGAATTCTC TTTCCTTAGT AGTATTCTGA AGTTCTTGAA GGGTAAGCTT    4200

GTGGACGAGT TGAAATCGAT TATTCAAGGG GTTTTTGATT CCAACAAGCA CGTGTTTAAA    4260

GAAGCTACTC AGGAAGCGAT TCGTACGACG GTCATGCAAG TGCCTGTCGC TGTAGTGGAT    4320

GCCCTTAAGA GCGCCGCGGG AAAAATTTAT AACAATTTTA CTAGTCGACG TACCTTTGGT    4380

AAGGATGAAG GCTCCTCTAG CGACGGCGCA TGTGAAGAGT ATTTCTCATG CGACGAAGGT    4440

GAAGGTCCGG GTCTGAAAGG GGGTTCCAGC TATGGCTTCT CAATTTTAGC GTTCTTTTCA    4500

CGCATTATGT GGGGAGCTCG TCGGCTTATT GTTAAGGTGA AGCATGAGTG TTTTGGGAAA    4560

CTTTTTGAAT TTCTATCGCT CAAGCTTCAC GAATTCAGGA CTCGCGTTTT TGGGAAGAAT    4620

AGAACGGACG TGGGAGTTTA CGATTTTTTG CCCACGGGCA TCGTGGAAAC GCTCTCATCG    4680

ATAGAAGAGT GCGACCAAAT TGAAGAACTT CTCGGCGACG ACCTGAAAGG TGACAAGGAT    4740

GCTTCGTTGA CCGATATGAA TTACTTTGAG TTCTCAGAAG ACTTCTTAGC CTCTATCGAG    4800

GAGCCGCCTT TCGCTGGATT GCGAGGAGGT AGCAAGAACA TCGCGATTTT GGCGATTTTG    4860

GAATACGCGC ATAATTTGTT TCGCATTGTC GCAAGCAAGT GTTCGAAACG ACCTTTATTT    4920

CTTGCTTTCG CCGAACTCTC AAGCGCCCTT ATCGAGAAAT TTAAGGAGGT TTTCCCTCGT    4980

AAGAGCCAGC TCGTCGCTAT CGTGCGCGAG TATACTCAGA GATTCCTCCG AAGTCGCATG    5040

CGTGCGTTGG GTTTGAATAA CGAGTTCGTG GTAAAATCTT TCGCCGATTT GCTACCCGCA    5100

TTAATGAAGC GGAAGGTTTC AGGTTCGTTC TTAGCTAGTG TTTATCGCCC ACTTAGAGGT    5160

TTCTCATATA TGTGTGTTTC AGCGGAGCGA CGTGAAAAGT TTTTTGCTCT CGTGTGTTTA    5220

ATCGGGTTAA GTCTCCCTTT CTTCGTGCGC ATCGTAGGAG CGAAAGCGTG CGAAGAACTC    5280

GTGTCCTCAG CGCGTCGCTT TTATGAGCGT ATTAAAATTT TCTAAGGCA GAAGTATGTC    5340

TCTCTTTCTA ATTTCTTTTG TCACTTGTTT AGCTCTGACG TTGATGACAG TTCCGCATCT    5400

GCAGGGTTGA AAGGTGGTGC GTCGCGAATG ACGCTCTTCC ACCTTCTGGT TCGCCTTGCT    5460

AGTGCCCTCC TATCGTTAGG GTGGGAAGGG TTAAAGCTAC TCTTATCGCA CCACAACTTG    5520

TTATTTTTGT GTTTTGCATT GGTTGACGAT GTGAACGTCC TTATCAAAGT TCTTGGGGGT    5580

CTTTCTTTCT TTGTGCAACC AATCTTTTCC TTGTTTGCGG CGATGCTTCT ACAACCGGAC    5640

AGGTTTGTGG AGTATTCCGA GAAACTTGTT ACAGCGTTTG AATTTTTCTT AAAATGTTCG    5700
```

-continued

```
CCTCGCGCGC CTGCACTACT CAAAGGGTTT TTTGAGTGCG TGGCGAACAG CACTGTGTCA    5760
AAAACCGTTC GAAGACTTCT TCGCTGTTTC GTGAAGATGC TCAAACTTCG AAAAGGGCGA    5820
GGGTTGCGTG CGGATGGTAG GGGTCTCCAT CGGCAGAAAG CCGTACCCGT CATACCTTCT    5880
AATCGGGTCG TGACCGACGG GGTTGAAAGA CTTTCGGTAA AGATGCAAGG AGTTGAAGCG    5940
TTGCGTACCG AATTGAGAAT CTTAGAAGAT TTAGATTCTG CCGTGATCGA AAAACTCAAT    6000
AGACGCAGAA ATCGTGACAC TAATGACGAC GAATTTACGC GCCCTGCTCA TGAGCAGATG    6060
CAAGAAGTCA CCACTTTCTG TTCGAAAGCC AACTCTGCTG GTTTGGCCCT GGAAAGGGCA    6120
GTGCTTGTGG AAGACGCTAT AAAGTCGGAG AAACTTTCTA AGACGGTTAA TGAGATGGTG    6180
AGGAAAGGGA GTACCACCAG CGAAGAAGTG GCCGTCGCTT TGTCGGACGA TGAAGCCGTG    6240
GAAGAAATCT CTGTTGCTGA CGAGCGAGAC GATTCGCCTA AGACAGTCAG GATAAGCGAA    6300
TACCTAAATA GGTTAAACTC AAGCTTCGAA TTCCCGAAGC CTATTGTTGT GGACGACAAC    6360
AAGGATACCG GGGGTCTAAC GAACGCCGTG AGGGAGTTTT ATTATATGCA AGAACTTGCT    6420
CTTTTCGAAA TCCACAGCAA ACTGTGCACC TACTACGATC AACTGCGCAT AGTCAACTTC    6480
GATCGTTCCG TAGCACCATG CAGCGAAGAT GCTCAGCTGT ACGTACGGAA GAACGGCTCA    6540
ACGATAGTGC AGGGTAAAGA GGTACGTTTG CACATTAAGG ATTTCCACGA TCACGATTTC    6600
CTGTTTGACG GAAAAATTTC TATTAACAAG CGGCGGCGAG GCGGAAATGT TTTATATCAC    6660
GACAACCTCG CGTTCTTGGC GAGTAATTTG TTCTTAGCCG GCTACCCCTT TTCAAGGAGC    6720
TTCGTCTTCA CGAATTCGTC GGTCGATATT CTCCTCTACG AAGCTCCACC CGGAGGTGGT    6780
AAGACGACGA CGCTGATTGA CTCGTTCTTG AAGGTCTTCA AGAAAGGTGA GGTTTCCACC    6840
ATGATCTTAA CCGCCAACAA AAGTTCGCAG GTTGAGATCC TAAAGAAAGT GGAGAAGGAA    6900
GTGTCTAACA TTGAATGCCA GAAACGTAAA GACAAAAGAT CTCCGAAAAA GAGCATTTAC    6960
ACCATCGACG CTTATTTAAT GCATCACCGT GGTTGTGATG CAGACGTTCT TTTCATCGAT    7020
GAGTGTTTCA TGGTTCATGC GGGTAGCGTA CTAGCTTGCA TTGAGTTCAC GAGGTGTCAT    7080
AAAGTAATGA TCTTCGGGGA TAGCCGGCAG ATTCACTACA TTGAAAGGAA CGAATTGGAC    7140
AAGTGTTTGT ATGGGGATCT CGACAGGTTC GTGGACCTGC AGTGTCGGGT TTATGGTAAT    7200
ATTTCGTACC GTTGTCCATG GGATGTGTGC GCTTGGTTAA GCACAGTGTA TGGCAACCTA    7260
ATCGCCACCG TGAAGGGTGA AAGCGAAGGT AAGAGCAGCA TGCGCATTAA CGAAATTAAT    7320
GCAGTCGACG ATTTAGTCCC CGACGTGGGT TCCACGTTTC TGTGTATGCT TCAGTCGGAG    7380
AAGTTGGAAA TCAGCAAGCA CTTTATTCGC AAGGGTTTGA CTAAACTTAA CGTTCTAACG    7440
GTGCATGAGG CGCAAGGTGA GACGTATGCG CGTGTGAACC TTGTGCGCAT TAAGTTTCAG    7500
GAGGATGAAC CCTTTAAATC TATCAGGCAC ATAACCGTCG CTCTTTCTCG TCACACCGAC    7560
AGCTTAACTT ATAACGTCTT AGCTGCTCGT CGAGGTGACG CCACTTGCGA TGCCATCCAG    7620
AAGGCTGCGG AATTGGTGAA CAAGTTTCGC GTTTTTCCTA CATCTTTTGG TGGTAGTGTT    7680
ATCAATCTCA ACGTGAAGAA GGACGTGGAA GATAACAGTA GGTGCAAGGC TTCGTCGGCA    7740
CCATTGAGCG TAATCAACGA CTTTTTGAAC GAAGTTATTC CCGGTACTGC GGTGATTGAT    7800
TTGGTGATT TGTCCGCGGA CTTCAGTACT GGGCCTTTTG AGTGCGGTGC CAGCGGTATT    7860
GTGGTGCGGG ACAACATCTC CTCCAGCAAC ATCACTGATC ACGATAAGCA GCGTGTTTAG    7920
```

The large polyprotein (papain-like proteases, methyltransferase, and helicase) has an amino acid sequence corresponding to SEQ. ID. No. 3 as follows:

```
Thr Leu Arg Glu Asn Pro Ile Ser Val Ser Gly Val Asn Leu Gly Arg
1               5                   10                  15

Ser Ala Ala Ala Gln Val Ile Tyr Phe Gly Ser Phe Thr Gln Pro Phe
                20              25              30

Ala Leu Tyr Pro Arg Gln Glu Ser Ala Ile Val Lys Thr Gln Leu Pro
            35              40              45

Pro Val Ser Val Lys Val Glu Cys Val Ala Ala Glu Val Ala Pro
    50              55              60

Asp Arg Gly Val Val Asp Lys Lys Pro Thr Ser Val Gly Val Pro Pro
65                  70              75                  80

Gln Arg Gly Val Leu Ser Phe Pro Thr Val Arg Asn Arg Gly Asp
                85              90                  95

Val Ile Ile Thr Gly Val Val His Glu Ala Leu Lys Lys Ile Lys Asp
            100             105             110

Gly Leu Leu Arg Phe Arg Val Gly Gly Asp Met Arg Phe Ser Arg Phe
            115             120             125

Phe Ser Ser Asb Tyr Gly Cys Arg Phe Val Ala Ser Val Arg Thr Asn
        130             135             140

Thr Thr Val Trp Leu Asn Cys Thr Lys Ala Ser Gly Glu Lys Phe Ser
145             150             155                     160

Leu Ala Ala Ala Cys Thr Ala Asp Tyr Val Ala Met Leu Arg Tyr Val
                165             170             175

Cys Gly Gly Lys Phe Pro Leu Val Leu Met Ser Arg Val Ile Tyr Pro
            180             185             190

Asp Gly Arg Cys Tyr Leu Ala His Met Arg Tyr Leu Cys Ala Phe Tyr
        195             200             205

Cys Arg Pro Phe Arg Glu Ser Asp Tyr Ala Leu Gly Met Trp Pro Thr
    210             215             220

Val Ala Arg Leu Arg Ala Cys Val Glu Lys Asn Phe Gly Val Glu Ala
225             230             235                     240

Cys Gly Ile Ala Leu Arg Gly Tyr Tyr Thr Ser Arg Asn Val Tyr His
            245             250             255

Cys Asp Tyr Asp Ser Ala Tyr Val Lys Tyr Phe Arg Asn Leu Ser Gly
        260             265             270

Arg Ile Gly Gly Gly Ser Phe Asp Pro Thr Ser Leu Thr Ser Val Ile
        275             280             285

Thr Val Lys Ile Ser Gly Leu Pro Gly Gly Leu Pro Lys Asn Ile Ala
    290             295             300

Phe Gly Ala Phe Leu Cys Asp Ile Arg Tyr Val Glu Pro Val Asp Ser
305             310             315                     320

Gly Gly Ile Gln Ser Ser Val Lys Thr Lys Arg Glu Asp Ala His Arg
            325             330             335

Thr Val Glu Glu Arg Ala Ala Gly Gly Ser Val Glu Gln Pro Arg Gln
            340             345             350

Lys Arg Ile Asp Glu Lys Gly Cys Gly Arg Val Pro Ser Gly Gly Phe
        355             360             365

Ser His Leu Leu Val Gly Asn Leu Asn Glu Val Arg Arg Lys Val Ala
    370             375             380

Ala Gly Leu Leu Arg Phe Arg Val Gly Gly Asp Met Asp Phe His Arg
385             390             395                     400

Ser Phe Ser Thr Gln Ala Gly His Arg Leu Leu Val Trp Arg Arg Ser
            405             410             415

Ser Arg Ser Val Cys Leu Glu Leu Tyr Ser Pro Ser Lys Asn Phe Leu
            420             425             430
```

-continued

```
Arg Tyr Asp Val Leu Pro Cys Ser Gly Asp Tyr Ala Ala Met Phe Ser
        435                 440                 445

Phe Ala Ala Gly Gly Arg Phe Pro Leu Val Leu Met Thr Arg Ile Arg
        450                 455                 460

Tyr Pro Asn Gly Phe Cys Tyr Leu Ala His Cys Arg Tyr Ala Cys Ala
465                 470                 475                 480.

Phe Leu Leu Arg Gly Phe Asp Pro Lys Arg Phe Asp Ile Gly Ala Phe
            485                 490                 495

Pro Thr Ala Ala Lys Leu Arg Asn Arg Met Val Ser Glu Leu Gly Glu
                500                 505                 510

Arg Ser Leu Gly Leu Asn Leu Tyr Gly Ala Tyr Thr Ser Arg Gly Val
            515                 520                 525

Phe His Cys Asp Tyr Asp Ala Lys Phe Ile Lys Asp Leu Arg Leu Met
    530                 535                 540

Ser Ala Val Ile Ala Gly Lys Asp Gly Val Glu Glu Val Val Pro Ser
545                 550                 555                 560

Asp Ile Thr Pro Ala Met Lys Gln Lys Thr Ile Glu Ala Val Tyr Asp
                565                 570                 575

Arg Leu Tyr Gly Gly Thr Asp Ser Leu Leu Lys Leu Ser Ile Glu Lys
            580                 585                 590

Asp Leu Ile Asp Phe Lys Asn Asp Val Gln Ser Leu Lys Lys Asp Arg
        595                 600                 605

Pro Ile Val Lys Val Pro Phe Tyr Met Ser Glu Ala Thr Gln Asn Ser
    610                 615                 620

Leu Thr Arg Phe Tyr Pro Gln Phe Glu Leu Lys Phe Ser His Ser Ser
625                 630                 635                 640

His Ser Asp His Pro Ala Ala Ala Ser Arg Leu Leu Glu Asn Glu
                645                 650                 655

Thr Leu Val Arg Leu Cys Gly Asn Ser Val Ser Asp Ile Gly Gly Cys
            660                 665                 670

Pro Leu Phe His Leu His Ser Lys Thr Gln Arg Arg Val His Val Cys
        675                 680                 685

Arg Pro Val Leu Asp Gly Lys Asp Ala Gln Arg Arg Val Val Arg Asp
    690                 695                 700

Leu Gln Tyr Ser Asn Val Arg Leu Gly Asp Asp Lys Ile Leu Glu
705                 710                 715                 720

Gly Pro Arg Asn Ile Asp Ile Cys His Tyr Pro Leu Gly Ala Cys Asp
                725                 730                 735

His Glu Ser Ser Ala Met Met Met Val Gln Val Tyr Asp Ala Ser Leu
            740                 745                 750

Tyr Glu Ile Cys Gly Ala Met Ile Lys Lys Ser Arg Ile Thr Tyr
        755                 760                 765

Leu Thr Met Val Thr Pro Gly Glu Phe Leu Asp Gly Arg Glu Cys Val
    770                 775                 780

Tyr Met Glu Ser Leu Asp Cys Glu Ile Glu Val Asp Val His Ala Asp
785                 790                 795                 800

Val Val Met Tyr Lys Phe Gly Ser Ser Cys Tyr Ser His Lys Leu Ser
                805                 810                 815

Ile Ile Lys Asp Ile Met Thr Thr Pro Tyr Leu Thr Leu Gly Gly Phe
            820                 825                 830

Leu Phe Ser Val Glu Met Tyr Glu Val Arg Met Gly Val Asn Tyr Phe
        835                 840                 845

Lys Ile Thr Lys Ser Glu Val Ser Pro Ser Ile Ser Cys Thr Lys Leu
```

-continued

Leu Arg Tyr Arg Arg Ala Asn Ser Asp Val Val Lys Val Lys Leu Pro
865                 870                 875                 880

Arg Phe Asp Lys Lys Arg Arg Met Cys Leu Pro Gly Tyr Asp Thr Ile
            885                 890                 895

Tyr Leu Asp Ser Lys Phe Val Ser Arg Val Phe Asp Tyr Val Val Cys
            900                 905                 910

Asn Cys Ser Ala Val Asn Ser Lys Thr Phe Glu Trp Val Trp Ser Phe
            915                 920                 925

Ile Lys Ser Ser Lys Ser Arg Val Ile Ile Ser Gly Lys Ile Ile His
    930                 935                 940

Lys Asp Val Asn Leu Asp Leu Lys Tyr Val Glu Ser Phe Ala Ala Val
945                 950                 955                 960

Met Leu Ala Ser Gly Val Arg Ser Arg Leu Ala Ser Glu Tyr Leu Ala
            965                 970                 975

Lys Asn Leu Ser His Phe Ser Gly Asp Cys Ser Phe Ile Glu Ala Thr
            980                 985                 990

Ser Phe Val Leu Arg Glu Lys Ile Arg Asn Met Thr Leu Asn Phe Asn
            995                 1000                1005

Glu Arg Leu Leu Gln Leu Val Lys Arg Val Ala Phe Ala Thr Leu Asp
    1010                1015                1020

Val Ser Phe Leu Asp Leu Asp Ser Thr Leu Glu Ser Ile Thr Asp Phe
1025                1030                1035                1040

Ala Glu Cys Lys Val Ala Ile Glu Leu Asp Glu Leu Gly Cys Leu Arg
            1045                1050                1055

Ala Glu Ala Glu Asn Glu Lys Ile Arg Asn Leu Ala Gly Asp Ser Ile
            1060                1065                1070

Ala Ala Lys Leu Ala Ser Glu Ile Val Asp Ile Asp Ser Lys Pro
            1075                1080                1085

Ser Pro Lys Gln Val Gly Asn Ser Ser Glu Asn Ala Asp Lys Arg
            1090                1095                1100

Glu Val Gln Arg Pro Gly Leu Arg Gly Gly Ser Arg Asn Gly Val Val
1105                1110                1115                1120

Gly Glu Phe Leu His Phe Val Val Asp Ser Ala Leu Arg Leu Phe Lys
            1125                1130                1135

Tyr Ala Thr Asp Gln Gln Arg Ile Lys Ser Tyr Val Arg Phe Leu Asp
            1140                1145                1150

Ser Ala Val Ser Phe Leu Asp Tyr Asn Tyr Asp Asn Leu Ser Phe Ile
            1155                1160                1165

Leu Arg Val Leu Ser Glu Gly Tyr Ser Cys Met Phe Ala Phe Leu Ala
    1170                1175                1180

Asn Arg Gly Asp Leu Ser Ser Arg Val Arg Ser Ala Val Cys Ala Val
1185                1190                1195                1200

Lys Glu Val Ala Thr Ser Cys Ala Asn Ala Ser Val Ser Lys Ala Lys
            1205                1210                1215

Val Met Ile Thr Phe Ala Ala Val Cys Ala Met Met Phe Asn Ser
            1220                1225                1230

Cys Gly Phe Ser Gly Asp Gly Arg Glu Tyr Lys Ser Tyr Ile His Arg
            1235                1240                1245

Tyr Thr Gln Val Leu Phe Asp Thr Ile Phe Glu Asp Ser Ser Tyr
            1250                1255                1260

Leu Pro Ile Glu Val Leu Ser Ser Ala Ile Cys Gly Ala Ile Val Thr
1265                1270                1275                1280

-continued

```
Leu Phe Ser Ser Gly Ser Ser Ile Ser Leu Asn Ala Phe Leu Leu Gln
                1285                1290                1295

Ile Thr Lys Gly Phe Ser Leu Glu Val Val Arg Asn Val Val Arg
            1300                1305                1310

Val Thr His Gly Leu Ser Thr Thr Ala Thr Asp Gly Val Ile Arg Gly
            1315                1320                1325

Val Phe Ser Gln Ile Val Ser His Leu Leu Val Gly Asn Thr Gly Asn
            1330                1335                1340

Val Ala Tyr Gln Ser Ala Phe Ile Ala Gly Val Val Pro Leu Leu Val
1345                1350                1355                1360

Lys Lys Cys Val Ser Leu Ile Phe Ile Leu Arg Glu Asp Thr Tyr Ser
                1365                1370                1375

Gly Phe Ile Lys His Gly Ile Ser Glu Phe Ser Phe Leu Ser Ser Ile
                1380                1385                1390

Leu Lys Phe Leu Lys Gly Lys Leu Val Asp Glu Leu Lys Ser Ile Ile
                1395                1400                1405

Gln Gly Val Phe Asp Ser Asn Lys His Val Phe Lys Glu Ala Thr Gln
            1410                1415                1420

Glu Ala Ile Arg Thr Thr Val Met Gln Val Pro Val Ala Val Val Asp
1425                1430                1435                1440

Ala Leu Lys Ser Ala Ala Gly Lys Ile Tyr Asn Asn Phe Thr Ser Arg
                1445                1450                1455

Arg Thr Phe Gly Lys Asp Glu Gly Ser Ser Ser Asp Gly Ala Cys Glu
                1460                1465                1470

Glu Tyr Phe Ser Cys Asp Glu Gly Glu Pro Gly Leu Lys Gly Gly
            1475                1480                1485

Ser Ser Tyr Gly Phe Ser Ile Leu Ala Phe Phe Ser Arg Ile Met Trp
            1490                1495                1500

Gly Ala Arg Arg Leu Ile Val Lys Val Lys His Glu Cys Phe Gly Lys
1505                1510                1515                1520

Leu Phe Glu Phe Leu Ser Leu Lys Leu His Glu Phe Arg Thr Arg Val
                1525                1530                1535

Phe Gly Lys Asn Arg Thr Asp Val Gly Val Tyr Asp Phe Leu Pro Thr
            1540                1545                1550

Gly Ile Val Glu Thr Leu Ser Ser Ile Glu Glu Cys Asp Gln Ile Glu
            1555                1560                1565

Glu Leu Leu Gly Asp Asp Leu Lys Gly Asp Lys Asp Ala Ser Leu Thr
1570                1575                1580

Asp Met Asn Tyr Phe Glu Phe Ser Glu Asp Phe Leu Ala Ser Ile Glu
1585                1590                1595                1600

Glu Pro Pro Phe Ala Gly Leu Arg Gly Gly Ser Lys Asn Ile Ala Ile
                1605                1610                1615

Leu Ala Ile Leu Glu Tyr Ala His Asn Leu Phe Arg Ile Val Ala Ser
                1620                1625                1630

Lys Cys Ser Lys Arg Pro Leu Phe Leu Ala Phe Ala Glu Leu Ser Ser
            1635                1640                1645

Ala Leu Ile GLu Lys Phe Lys Glu Val Phe Pro Arg Lys Ser Gln Leu
            1650                1655                1660

Val Ala Ile Val Arg Glu Tyr Thr Gln Arg Phe Leu Arg Ser Arg Met
1665                1670                1675                1680

Arg Ala Leu Gly Leu Asn Asn Glu Phe Val Val Lys Ser Phe Ala Asp
                1685                1690                1695

Leu Leu Pro Ala Leu Met Lys Arg Lys Val Ser Gly Ser Phe Leu Ala
                1700                1705                1710
```

-continued

```
Ser Val Tyr Arg Pro Leu Arg Gly Phe Ser Tyr Met Cys Val Ser Ala
         1715                1720                1725

Glu Arg Arg Glu Lys Phe Phe Ala Leu Val Cys Leu Ile Gly Leu Ser
     1730                1735                1740

Leu Pro Phe Phe Val Arg Ile Val Gly Ala Lys Ala Cys Glu Glu Leu
1745                1750                1755                1760

Val Ser Ser Ala Arg Arg Phe Tyr Glu Arg Ile Lys Ile Phe Leu Arg
             1765                1770                1775

Gln Lys Tyr Val Ser Leu Ser Asn Phe Phe Cys His Leu Phe Ser Ser
         1780                1785                1790

Asp Val Asp Asp Ser Ser Ala Ser Ala Gly Leu Lys Gly Gly Ala Ser
         1795                1800                1805

Arg Met Thr Leu Phe His Leu Leu Val Arg Leu Ala Ser Ala Leu Leu
     1810                1815                1820

Ser Leu Gly Trp Glu Gly Leu Lys Leu Leu Ser His His Asn Leu
1825                1830                1835                1840

Leu Phe Leu Cys Phe Ala Leu Val Asp Asp Val Asn Val Leu Ile Lys
             1845                1850                1855

Val Leu Gly Gly Leu Ser Phe Val Gln Pro Ile Phe Ser Leu Phe
         1860                1865                1870

Ala Ala Met Leu Leu Gln Pro Asp Arg Phe Val Glu Tyr Ser Glu Lys
         1875                1880                1885

Leu Val Thr Ala Phe Glu Phe Phe Leu Lys Cys Ser Pro Arg Ala Pro
     1890                1895                1900

Ala Leu Leu Lys Gly Phe Phe Glu Cys Val Ala Asn Ser Thr Val Ser
1905                1910                1915                1920

Lys Thr Val Arg Arg Leu Leu Arg Cys Phe Val Lys Met Leu Lys Leu
             1925                1930                1935

Arg Lys Gly Arg Gly Leu Arg Ala Asp Gly Arg Gly Leu His Arg Gln
         1940                1945                1950

Lys Ala Val Pro Val Ile Pro Ser Asn Arg Val Val Thr Asp Gly Val
         1955                1960                1965

Glu Arg Leu Ser Val Lys Met Gln Gly Val Glu Ala Leu Arg Thr Glu
     1970                1975                1980

Leu Arg Ile Leu Glu Asp Leu Asp Ser Ala Val Ile Glu Lys Leu Asn
1985                1990                1995                2000

Arg Arg Arg Asn Arg Asp Thr Asn Asp Asp Glu Phe Thr Arg Pro Ala
             2005                2010                2015

His Glu Gln Met Gln Glu Val Thr Thr Phe Cys Ser Lys Ala Asn Ser
         2020                2025                2030

Ala Gly Leu Ala Leu Glu Arg Ala Val Leu Val Glu Asp Ala Ile Lys
         2035                2040                2045

Ser Glu Lys Leu Ser Lys Thr Val Asn Glu Met Val Arg Lys Gly Ser
     2050                2055                2060

Thr Thr Ser Glu Glu Val Ala Val Ala Leu Ser Asp Asp Glu Ala Val
2065                2070                2075                2080

Glu Glu Ile Ser Val Ala Asp Glu Arg Asp Asp Ser Pro Lys Thr Val
             2085                2090                2095

Arg Ile Ser Glu Tyr Leu Asn Arg Leu Asn Ser Ser Phe Glu Phe Pro
         2100                2105                2110

Lys Pro Ile Val Val Asp Asp Asn Lys Asp Thr Gly Gly Leu Thr Asn
         2115                2120                2125

Ala Val Arg Glu Phe Tyr Tyr Met Gln Glu Leu Ala Leu Phe Glu Ile
```

-continued

His Ser Lys Leu Cys Thr Tyr Tyr Asp Gln Leu Arg Ile Val Asn Phe
2145                 2150                 2155                 2160

Asp Arg Ser Val Ala Pro Cys Ser Glu Asp Ala Gln Leu Tyr Val Arg
            2165                 2170                 2175

Lys Asn Gly Ser Thr Ile Val Gln Gly Lys Glu Val Arg Leu His Ile
            2180                 2185                 2190

Lys Asp Phe His Asp His Asp Phe Leu Phe Asp Gly Lys Ile Ser Ile
            2195                 2200                 2205

Asn Lys Arg Arg Arg Gly Gly Asn Val Leu Tyr His Asp Asn Leu Ala
            2210                 2215                 2220

Phe Leu Ala Ser Asn Leu Phe Leu Ala Gly Tyr Pro Phe Ser Arg Ser
2225                 2230                 2235                 2240

Phe Val Phe Thr Asn Ser Ser Val Asp Ile Leu Leu Tyr Glu Ala Pro
            2245                 2250                 2255

Pro Gly Gly Gly Lys Thr Thr Leu Ile Asp Ser Phe Leu Lys Val
            2260                 2265                 2270

Phe Lys Lys Gly Glu Val Ser Thr Met Ile Leu Thr Ala Asn Lys Ser
            2275                 2280                 2285

Ser Gln Val Glu Ile Leu Lys Lys Val Glu Lys Glu Val Ser Asn Ile
            2290                 2295                 2300

Glu Cys Gln Lys Arg Lys Asp Lys Arg Ser Pro Lys Lys Ser Ile Tyr
2305                 2310                 2315                 2320

Thr Ile Asp Ala Tyr Leu Met His His Arg Gly Cys Asp Ala Asp Val
            2325                 2330                 2335

Leu Phe Ile Asp Glu Cys Phe Met Val His Ala Gly Ser Val Leu Ala
            2340                 2345                 2350

Cys Ile Glu Phe Thr Arg Cys His Lys Val Met Ile Phe Gly Asp Ser
            2355                 2360                 2365

Arg Gln Ile His Tyr Ile Glu Arg Asn Glu Leu Asp Lys Cys Leu Tyr
            2370                 2375                 2380

Gly Asp Leu Asp Arg Phe Val Asp Leu Gln Cys Arg Val Tyr Gly Asn
2385                 2390                 2395                 2400

Ile Ser Tyr Arg Cys Pro Trp Asp Val Cys Ala Trp Leu Ser Thr Val
            2405                 2410                 2415

Tyr Gly Asn Leu Ile Ala Thr Val Lys Gly Glu Ser Glu Gly Lys Ser
            2420                 2425                 2430

Ser Met Arg Ile Asn Glu Ile Asn Ser Val Asp Leu Val Pro Asp
            2435                 2440                 2445

Val Gly Ser Thr Phe Leu Cys Met Leu Gln Ser Gln Lys Leu Glu Ile
2450                 2455                 2460

Ser Lys His Phe Ile Arg Lys Gly Leu Thr Lys Leu Asn Val Leu Thr
2465                 2470                 2475                 2480

Val His Glu Ala Gln Gly Glu Thr Tyr Ala Arg Val Asn Leu Val Arg
            2485                 2490                 2495

Leu Lys Phe Gln Glu Asp Glu Pro Phe Lys Ser Ile Arg His Ile Thr
            2500                 2505                 2510

Val Ala Leu Ser Arg His Thr Asp Ser Leu Thr Tyr Asn Val Leu Ala
            2515                 2520                 2525

Ala Arg Arg Gly Asp Ala Thr Cys Asp Ala Ile Gln Lys Ala Ala Glu
            2530                 2535                 2540

Leu Val Asn Lys Phe Arg Val Pro Thr Ser Phe Gly Gly Ser Val
2545                 2550                 2555                 2560

-continued

```
Ile Asn Leu Asn Val Lys Lys Asp Val Glu Asp Asn Ser Arg Cys Lys
             2565                2570                2575

Ala Ser Ser Ala Pro Leu Ser Val Ile Asn Asp Phe Leu Asn Glu Val
         2580                2585                2590

Asn Pro Gly Thr Ala Val Ile Asp Phe Gly Asp Leu Ser Ala Asp Phe
     2595                2600                2605

Ser Thr Gly Pro Phe Glu Cys Gly Ala Ser Gly Ilt Val Val Arg Asp
    2610                2615                2620

Asn Ile Ser Ser Ser Asn Ile Thr Asp His Asp Lys Gln Arg Val
2625                2630                2635
``` and has a molecular weight of about 290 to 300 kDa, preferably 294 kDa.

Another such DNA molecule (GLRaV-2 ORF1b) includes nucleotides 7922–9301 of SEQ. ID. No. 1 and codes for a grapevine leafroll virus RNA-dependent RNA polymerase (RdRP). This DNA molecule comprises the nucleotide sequence corresponding to SEQ. ID. No. 4 as follows:

```
AGCGTAGTTC GGTCGCAGGC GATTCCGCGT AGAAAACCTT CTCTACAAGA AAATTTGTAT      60

TCGTTTGAAG CGCGGAATTA TAACTTCTCG ACTTGCGACC GTAACACATC TGCTTCAATG     120

TTCGGAGAGG CTATGGCGAT GAACTGTCTT CGTCGTTGCT TCGACCTAGA TGCCTTTTCG     180

TCCCTGCGTG ATGATGTGAT TAGTATCACA CGTTCAGGCA TCGAACAATG GCTGGAGAAA     240

CGTACTCCTA GTCAGATTAA AGCATTAATG AAGGATGTTG AATCGCCTTT GGAAATTGAC     300

GATGAAATTT GTCGTTTTAA GTTGATGGTG AAGCGTGACG CTAAGGTGAA GTTAGACTCT     360

TCTTGTTTAA CTAAACACAG CGCCGCTCAA AATATCATGT TTCATCGCAA GAGCATTAAT     420

GCTATCTTCT CTCCTATCTT TAATGAGGTG AAAAACCGAA TAATGTGCTG TCTTAAGCCT     480

AACATAAAGT TTTTTACGGA GATGACTAAC AGGGATTTTG CTTCTGTTGT CAGCAACATG     540

CTTGGTGACG ACGATGTGTA CCATATAGGT GAAGTTGATT TCTCAAAGTA CGACAAGTCT     600

CAAGATGCTT TCGTGAAGGC TTTTGAAGAA GTAATGTATA AGGAACTCGG TGTTGATGAA     660

GAGTTGCTGG CTATCTGGAT GTGCGGCGAG CGGTTATCGA TAGCTAACAC TCTCGATGGT     720

CAGTTGTCCT TCACGATCGA GAATCAAAGG AAGTCGGGAG CTTCGAACAC TTGGATTGGT     780

AACTCTCTCG TCACTTTGGG TATTTTAAGT CTTTACTACG ACGTTAGAAA TTTCGAGGCG     840

TTGTACATCT CGGGCGATGA TTCTTTAATT TTTTCTCGCA GCGAGATTTC GAATTATGCC     900

GACGACATAT GCACTGACAT GGGTTTTGAG ACAAAATTTA TGTCCCCAAG TGTCCCGTAC     960

TTTTGTTCTA AATTTGTTGT TATGTGTGGT CATAAGACGT TTTTTGTTCC CGACCCGTAC    1020

AAGCTTTTTG TCAAGTTGGG AGCAGTCAAA GAGGATGTTT CAATGGATTT CCTTTTCGAG    1080

ACTTTTACCT CCTTTAAAGA CTTAACCTCC GATTTTAACG ACGAGCGCTT AATTCAAAAG    1140

CTCGCTGAAC TTGTGGCTTT AAAATATGAG GTTCAAACCG GCAACACCAC CTTGGCGTTA    1200

AGTGTGATAC ATTGTTTGCG TTCGAATTTC CTCTCGTTTA GCAAGTTATA TCCTCGCGTG    1260

AAGGGATGGC AGGTTTTTTA CACGTCGGTT AAGAAAGCGC TTCTCAAGAG TGGGTGTTCT    1320

CTCTTCGACA GTTTCATGAC CCCTTTTGGT CAGGCTGTCA TGGTTTGGGA TGATGAGTAG    1380
```

The RNA-dependent RNA polymerase has an amino acid sequence corresponding to SEQ. ID. No. 5 as follows:

```
Ser Val Val Arg Ser Gln Ala Ile Pro Arg Arg Lys Pro Ser Leu Gln
1               5                   10                  15

Glu Asn Leu Tyr Ser Phe Glu Ala Arg Asn Tyr Asn Phe Ser Thr Cys
                20                  25                  30

Asp Arg Asn Thr Ser Ala Ser Met Phe Gly Glu Ala Met Ala Met Asn
                35                  40                  45

Cys Leu Arg Arg Cys Phe Asp Leu Asp Ala Phe Ser Ser Leu Arg Asp
                50                  55                  60

Asp Val Ile Ser Ile Thr Arg Ser Gly Ile Glu Gln Trp Leu Glu Lys
65                  70                  75                  80

Arg Thr Pro Ser Gln Ile Lys Ala Leu Met Lys Asp Val Glu Ser Pro
                85                  90                  95

Leu Glu Ile Asp Asp Glu Ile Cys Arg Phe Lys Leu Met Val Lys Arg
                100                 105                 110

Asp Ala Lys Val Lys Leu Asp Ser Ser Cys Leu Thr Lys His Ser Ala
                115                 120                 125

Ala Gln Asn Ile Met Phe His Arg Lys Ser Ile Asn Ala Ile Phe Ser
                130                 135                 140

Pro Ile Phe Asn Glu Val Lys Asn Arg Ile Met Cys Cys Leu Lys Pro
145                 150                 155                 160

Asn Ile Lys Phe Phe Thr Glu Met Thr Asn Arg Asp Phe Ala Ser Val
                165                 170                 175

Val Ser Asn Met Leu Gly Asp Asp Val Tyr His Ile Gly Glu Val
                180                 185                 190

Asp Phe Ser Lys Tyr Asp Lys Ser Gln Asp Ala Phe Val Lys Ala Phe
                195                 200                 205

Glu Glu Val Met Tyr Lys Glu Leu Gly Val Asp Glu Glu Leu Leu Ala
                210                 215                 220

Ile Trp Met Cys Gly Glu Arg Leu Ser Ile Ala Asn Thr Leu Asp Gly
225                 230                 235                 240

Gln Leu Ser Phe thr Ile Glu Asn Gln Arg Lys Ser Gly Ala Ser Asn
                245                 250                 255

Thr Trp Ile Gly Asn Ser Leu Val Thr Leu Gly Ile Leu Ser Leu Tyr
                260                 265                 270

Tyr Asp Val Arg Asn Phe Glu Ala Leu Tyr Ile Ser Gly Asp Asp Ser
                275                 280                 285

Leu Ile Phe Ser Arg Ser Glu Ile Ser Asn Tyr Ala Asp Asp Ile Cys
                290                 295                 300

Thr Asp Met Gly Phe Glu Thr Lys Phe Met Ser Pro Ser Val Pro Tyr
305                 310                 315                 320

Phe Cys Ser Lys Phe Val Val Met Cys Gly His Lys Thr Phe Phe Val
                325                 330                 335

Pro Asp Pro Tyr Lys Leu Phe Val Lys Leu Gly Ala Val Lys Glu Asp
```

-continued

```
                340                    345                    350
Val Ser Met Asp Phe Leu Phe Glu Thr Phe Thr Ser Phe Lys Asp Leu
        355                    360                    365

Thr Ser Asp Phe Asn Asp Glu Arg Leu Ile Gln Lys Leu Ala Glu Leu
        370                    375                    380

Val Ala Leu Lys Tyr Glu Val Gln Thr Gly Asn Thr Thr Leu Ala Leu
385                     390                    395                 400

Ser Val Ile His Cys Leu Arg Ser Asn Phe Leu Ser Phe Ser Lys Leu
                405                    410                    415

Tyr Pro Arg Val Lys Gly Trp Gln Val Phe Tyr Thr Ser Val Lys Lys
                420                    425                    430

Ala Leu Leu Lys Ser Gly Cys Ser Leu Phe Asp Ser Phe Met Thr Pro
        435                    440                    445

Phe Gly Gln Ala Val Met Val Trp Asp Asp Glu
450                     455
``` and a molecular weight from about 50 to about 54 kDa, preferably about 52 kDa.

Another such DNA molecule (GLRAV-2 ORF2) includes nucleotides 9365-9535 SEQ. ID. No. 1 and codes for a small, grapevine leafroll virus hydrophobic protein or polypeptide. This DNA molecule comprises the nucleotide sequence corresponding to SEQ. ID. No. 6 as follows:

```
ATGAATCAGG TTTTGCAGTT TGAATGTTTG TTTCTGCTGA ATCTCGCGGT TTTTGCTGTG    60

ACTTTCATTT TCATTCTTCT GGTCTTCCGC GTGATTAAGT CTTTTCGCCA GAAGGGTCAC   120

GAAGCACCTG TTCCCGTTGT TCGTGGCGGG GGTTTTTCAA CCGTAGTGTA G            171
```

The small hydrophobic protein or polypeptide has an amino acid sequence corresponding to SEQ. ID. No. 7 as follows:

```
Met Asn Gln Val Leu Gln Phe Glu Cys Leu Phe Leu Leu Asn Leu Ala
1               5                   10                  15

Val Phe Ala Val Thr Phe Ile Phe Ile Leu Leu Val Phe Arg Val Ile
                20                  25                  30

Lys Ser Phe Arg Gln Lys Gly His Glu Ala Pro Val Pro Val Val Arg
        35                  40                  45

Gly Gly Gly Phe Ser Thr Val Val
        50                  55
``` and a molecular weight from about 5 to about 7 kDa, preferably about 6 kDa.

Another such DNA molecule (GLRaV-2 ORF3) includes nucleotides 9551–11350 of SEQ. ID. No. 1 and encodes for a grapevine leafroll virus heat shock 70 protein. This DNA molecule comprises the nucleotide sequence corresponding to SEQ. ID. No. 8 as follows:

```
ATGGTAGTTT TCGGTTTGGA CTTTGGCACC ACATTCTCTA CGGTGTGTGT GTACAAGGAT    60
GGACGAGTTT TTTCATTCAA GCAGAATAAT TCGGCGTACA TCCCCACTTA CCTCTATCTC   120
TTCTCCGATT CTAACCACAT GACTTTTGGT TACGAGGCCG AATCACTGAT GAGTAATCTG   180
AAAGTTAAAG GTTCGTTTTA TAGAGATTTA AAACGTTGGG TGGGTTGCGA TTCGAGTAAC   240
CTCGACGCGT ACCTTGACCG TTTAAAACCT CATTACTCGG TCCGCTTGGT TAAGATCGGC   300
TCTGGCTTGA ACGAAACTGT TTCAATTGGA AACTTCGGGG GCACTGTTAA GTCTGAGGCT   360
CATCTGCCAG GGTTGATAGC TCTCTTTATT AAGGCTGTCA TTAGTTGCGC GGAGGGCGCG   420
TTTGCGTGCA CTTGCACCGG GGTTATTTGT TCAGTACCTG CCAATTATGA TAGCGTTCAA   480
AGGAATTTCA CTGATCAGTG TGTTTCACTC AGCGGTTATC AGTGCGTATA TATGATCAAT   540
GAACCTTCAG CGGCTGCGCT ATCTGCGTGT AATTCGATTG GAAAGAAGTC CGCAAATTTG   600
GCTGTTTACG ATTTCGGTGG TGGGACCTTC GACGTGTCTA TCATTTCATA CCGCAACAAT   660
ACTTTTGTTG TGCGAGCTTC TGGAGGCGAT CTAAATCTCG GTGGAAGGGA TGTTGATCGT   720
GCGTTTCTCA CGCACCTCTT CTCTTTAACA TCGCTGGAAC CTGACCTCAC TTTGGATATC   780
TCGAATCTGA AGAATCTTTT ATCAAAAACG GACGCAGAGA TAGTTTACAC TTTGAGAGGT   840
GTCGATGGAA GAAAAGAAGA CGTTAGAGTA AACAAAAACA TTCTTACGTC GGTGATGCTC   900
CCCTACGTGA ACAGAACGCT TAAGATATTA GAGTCAACCT TAAAATCGTA TGCTAAGAGT   960
ATGAATGAGA GTGCGCGAGT TAAGTGCGAT TTAGTGCTGA TAGGAGGATC TTCATATCTT  1020
CCTGGCCTGG CAGACGTACT AACGAAGCAT CAGAGCGTTG ATCGTATCTT AAGAGTTTCG  1080
GATCCTCGGG CTGCCGTGGC CGTCGGTTGC GCATTATATT CTTCATGCCT CTCAGGATCT  1140
GGGGGGTTGC TACTGATCGA CTGTGCAGCT CACACTGTCG CTATAGCGGA CAGAAGTTGT  1200
CATCAAATCA TTTGCGCTCC AGCGGGGGCA CCGATCCCCT TTTCAGGAAG CATGCCTTTG  1260
TACTTAGCCA GGGTCAACAA GAACTCGCAG CGTGAAGTCG CCGTGTTTGA AGGGGAGTAC  1320
GTTAAGTGCC CTAAGAACAG AAAGATCTGT GGAGCAAATA TAAGATTTTT TGATATAGGA  1380
GTGACGGGTG ATTCGTACGC ACCCGTTACC TTCTATATGG ATTTCTCCAT TTCAAGCGTA  1440
GGAGCCGTTT CATTCGTGGT GAGAGGTCCT GAGGGTAAGC AAGTGTCACT CACTGGAACT  1500
CCAGCGTATA ACTTTTCGTC TGTGGCTCTC GGATCACGCA GTGTCCGAGA ATTGCATATT  1560
AGTTTAAATA ATAAAGTTTT TCTCGGTTTG CTTCTACATA GAAAGGCGGA TCGACGAATA  1620
CTTTTCACTA AGGATGAAGC GATTCGATAC GCCGATTCAA TTGATATCGC GGATGTGCTA  1680
AAGGAATATA AAAGTTACGC GGCCAGTGCC TTACCACCAG ACGAGGATGT CGAATTACTC  1740
CTGGGAAAGT CTGTTCAAAA AGTTTTACGG GGAAGCAGAC TGGAAGAAAT ACCTCTCTAG  1800
```

The heat shock 70 protein is believed to function as a chaperone protein and has an amino acid sequence corresponding to SEQ. ID. No. 9 as follows:

```
Met Val Val Phe Gly Leu Asp Phe Gly Thr Thr Phe Ser Thr Val Cys
1               5                   10                  15

Val Tyr Lys Asp Gly Arg Val Phe Ser Phe Lys Gln Asn Asn Ser Ala
            20                  25                  30

Tyr Ile Pro Thr Tyr Leu Tyr Leu Phe Ser Asp Ser Asn His Met Thr
        35                  40                  45

Phe Gly Tyr Glu Ala Glu Ser Leu Met Ser Asn Leu Lys Val Lys Gly
    50                  55                  60

Ser Phe Tyr Arg Asp Leu Lys Arg Trp Val Gly Cys Asp Ser Ser Asn
```

-continued

```
             65                  70                  75                  80
Leu Asp Ala Tyr Leu Asp Arg Leu Lys Pro His Tyr Ser Val Arg Leu
                 85                  90                  95
Val Lys Ile Gly Ser Gly Leu Asn Glu Thr Val Ser Ile Gly Asn Phe
                100                 105                 110
Gly Gly Thr Val Lys Ser Glu Ala His Leu Pro Gly Leu Ile Ala Leu
                115                 120                 125
Phe Ile Lys Ala Val Ile Ser Cys Ala Glu Gly Ala Phe Ala Cys Thr
    130                 135                 140
Cys Thr Gly Val Ile Cys Ser Val Pro Ala Asn Tyr Asp Ser Val Gln
145                 150                 155                 160
Arg Asn Phe Thr Asp Gln Cys Val Ser Leu Ser Gly Tyr Gln Cys Val
                165                 170                 175
Tyr Met Ile Asn Glu Pro Ser Ala Ala Ala Leu Ser Ala Cys Asn Ser
                180                 185                 190
Ile Gly Lys Lys Ser Ala Asn Leu Ala Val Tyr Asp Phe Gly Gly Gly
                195                 200                 205
Thr Phe Asp Val Ser Ile Ile Ser Tyr Arg Asn Asn Thr Phe Val Val
            210                 215                 220
Arg Ala Ser Gly Gly Asp Leu Asn Leu Gly Gly Arg Asp Val Asp Arg
225                 230                 235                 240
Ala Phe Leu Thr His Leu Phe Ser Leu Thr Ser Leu Glu Pro Asp Leu
                245                 250                 255
Thr Leu Asp Ile Ser Asn Leu Lys Glu Ser Leu Ser Lys Thr Asp Ala
                260                 265                 270
Glu Ile Val Tyr Thr Leu Arg Gly Val Asp Gly Arg Lys Glu Asp Val
                275                 280                 285
Arg Val Asn Lys Asn Ile Leu Thr Ser Val Met Leu Pro Tyr Val Asn
        290                 295                 300
Arg Thr Leu Lys Ile Leu Glu Ser Thr Leu Lys Ser Tyr Ala Lys Ser
305                 310                 315                 320
Met Asn Glu Ser Ala Arg Val Lys cys Asp Leu Val Leu Ile Gly Gly
                325                 330                 335
Ser Ser Tyr Leu Pro Gly Leu Ala Asp Val Leu Thr Lys His Gln Ser
                340                 345                 350
Val Asp Arg Ile Leu Arg Val Ser Asp Pro Arg Ala Ala Val Ala Val
                355                 360                 365
Gly Cys Ala Leu Tyr Ser Ser Cys Leu Ser Gly Ser Gly Gly Leu Leu
                370                 375                 380
Leu Ile Asp Cys Ala Ala His Thr Val Ala Ile Ala Asp Arg Ser Cys
385                 390                 395                 400
His Gln Ile Ile Cys Ala Pro Ala Gly Ala Pro Ile Pro Phe Ser Gly
                405                 410                 415
Ser Met Pro Leu Tyr Leu Ala Arg Val Asn Lys Asn Ser Gln Arg Glu
                420                 425                 430
Val Ala Val Phe Glu Gly Glu Tyr Val Lys Cys Pro Lys Asn Arg Lys
                435                 440                 445
Ile Cys Gly Ala Asn Ile Arg Phe Phe Asp Ile Gly Val Thr Gly Asp
            450                 455                 460
Ser Tyr Ala Pro Val Thr Phe Tyr Met Asp Phe Ser Ile Ser Ser Val
465                 470                 475                 480
Gly Ala Val Ser Phe Val Val Arg Gly Pro Glu Gly Lys Gln Val Ser
                485                 490                 495
```

```
Leu Thr Gly Thr Pro Ala Tyr Asn Phe Ser Ser Val Ala Leu Gly Ser
            500                 505                 510

Arg Ser Val Arg Glu Leu His Ile Ser Leu Asn Asn Lys Val Phe Leu
            515                 520                 525

Gly Leu Leu His Arg Lys Ala Asp Arg Arg Ile Leu Phe Thr Lys
    530                 535                 540

Asp Glu Ala Ile Arg Tyr Ala Asp Ser Ile Asp Ile Ala Asp Val Leu
545                 550                 555                 560

Lys Glu Tyr Lys Ser Tyr Ala Ala Ser Ala Leu Pro Pro Asp Glu Asp
                565                 570                 575

Val Glu Leu Leu Leu Gly Lys Ser Val Gln Lys Val Leu Arg Gly Ser
            580                 585                 590

Arg Leu Glu Glu Ile Pro Leu
            595
``` and a molecular weight from about 63 to about 67 kDa, preferably about 65 kDa.

Another such DNA molecule (GLRaV-2 ORF4) includes nucleotides 11277–12932 of SEQ. ID. No. 1 and codes for a putative grapevine leafroll virus heat shock 90 protein. This DNA molecule comprises a nucleotide sequence corresponding to SEQ. ID. No. 10 as follows:

```
ATGTCGAATT ACTCCTGGGA AAGTCTGTTC AAAAAGTTTT ACGGGAAGC AGACTGGAAG      60
AAATACCTCT CTAGGAGCAT AGCAGCACAC TCAAGTGAAA TTAAAACTCT ACCAGACATT    120
CGATTGTACG GCGGTAGGGT TGTAAAGAAG TCCGAATTCG AATCAGCACT TCCTAATTCT    180
TTTGAACAGG AATTAGGACT GTTCATACTG AGCGAACGGG AAGTGGGATG GAGCAAATTA    240
TGCGGAATAA CGGTGGAAGA AGCAGCATAC GATCTTACGA ATCCCAAGGC TTATAAATTC    300
ACTGCCGAGA CATGTAGCCC GGATGTAAAA GGTGAAGGAC AAAAATACTC TATGGAAGAC    360
GTGATGAATT TCATGCGTTT ATCAAATCTG GATGTTAACG ACAAGATGCT GACGGAACAG    420
TGTTGGTCGC TGTCCAATTC ATGCGGTGAA TTGATCAACC CAGACGACAA AGGGCGATTC    480
GTGGCTCTCA CCTTTAAGGA CAGAGACACA GCTGATGACA CGGGTGCCGC CAACGTGGAA    540
TGTCGCGTGG GCGACTATCT AGTTTACGCT ATGTCCCTGT TGAGCAGAG GACCCAAAAA     600
TCGCAGTCTG GCAACATCTC TCTGTACGAA AAGTACTGTG AATACATCAG GACCTACTTA    660
GGGAGTACAG ACCTGTTCTT CACAGCGCCG GACAGGATTC CGTTACTTAC GGGCATCCTA    720
TACGATTTTT GTAAGGAATA CAACGTTTTC TACTCGTCAT ATAAGAGAAA CGTCGATAAT    780
TTCAGATTCT TCTTGGCGAA TTATATGCCT TTGATATCTG ACGTCTTTGT CTTCCAGTGG    840
GTAAAACCCG CGCCGGATGT TCGGCTGCTT TTTGAGTTAA GTGCAGCGGA ACTAACGCTG    900
GAGGTTCCCA CACTGAGTTT GATAGATTCT CAAGTTGTGG TAGGTCATAT CTTAAGATAC    960
GTAGAATCCT ACACATCAGA TCCAGCCATC GACGCGTTAG AAGACAAACT GGAAGCGATA   1020
CTGAAAAGTA GCAATCCCCG TCTATCGACA GCGCAACTAT GGGTTGGTTT CTTTTGTTAC   1080
TATGGTGAGT TTCGTACGGC TCAAAGTAGA GTAGTGCAAA GACCAGGCGT ATACAAAACA   1140
CCTGACTCAG TGGGTGGATT TGAAATAAAC ATGAAAGATG TTGAGAAATT CTTCGATAAA   1200
CTTCAGAGAG AATTGCCTAA TGTATCTTTG CGGCGTCAGT TTAACGGAGC TAGAGCGCAT   1260
GAGGCTTTCA AAATATTTAA AAACGGAAAT ATAAGTTTCA GACCTATATC GCGTTTAAAC   1320
GTGCCTAGAG AGTTCTGGTA TCTGAACATA GACTACTTCA GGCACGCGAA TAGGTCCGGG   1380
TTAACCGAAG AAGAAATACT CATCCTAAAC AACATAAGCG TTGATGTTAG GAAGTTATGC   1440
GCTGAGAGAG CGTGCAATAC CCTACCTAGC GCGAAGCGCT TTAGTAAAAA TCATAAGAGT   1500
```

-continued

```
AATATACAAT CATCACGCCA AGAGCGGAGG ATTAAAGACC CATTGGTAGT CCTGAAAGAC    1560

ACTTTATATG AGTTCCAACA CAAGCGTGCC GGTTGGGGGT CTCGAAGCAC TCGAGACCTC    1620

GGGAGTCGTG CTGACCACGC GAAAGGAAGC GGTTGA                              1656
```

The heat shock 90 protein has an amino acid sequence corresponding to SEQ. ID. No. 11 as follows:

```
Met Ser Asn Tyr Ser Trp Glu Ser Leu Phe Lys Lys Phe Tyr Gly Glu
1               5                   10                  15

Ala Asp Trp Lys Lys Tyr Leu Ser Arg Ser Ile Ala Ala His Ser Ser
            20                  25                  30

Glu Ile Lys Thr Leu Pro Asp Ile Arg Leu Tyr Gly Gly Arg Val Val
            35              40                  45

50                  55                  60

Leu Gly Leu Phe Ile Leu Ser Glu Arg Glu Val Gly Trp Ser Lys Leu
65                  70                  75                  80

Cys Gly Ile Thr Val Glu Glu Ala Ala Tyr Asp Leu Thr Asn Pro Lys
                85                  90                  95

Ala Tyr Lys Phe Thr Ala Glu Thr Cys Ser Pro Asp Val Lys Gly Glu
            100                 105                 110

Gly Gln Lys Tyr Ser Met Glu Asp Val Met Asn Phe Met Arg Leu Ser
        115                 120                 125

Asn Leu Asp Val Asn Asp Lys Met Leu Thr Glu Gln Cys Trp Ser Leu
130                 135                 140

Ser Asn Ser Cys Gly Glu Leu Ile Asn Pro Asp Asp Lys Gly Arg Phe
145                 150                 155                 160

Val Ala Leu Thr Phe Lys Asp Arg Asp Thr Ala Asp Asp Thr Gly Ala
                165                 170                 175

Ala Asn Val Glu Cys Arg Val Gly Asp Tyr Leu Val Tyr Ala Met Ser
            180                 185                 190

Leu Phe Glu Gln Arg Thr Gln Lys Ser Gln Ser Gly Asn Ile Ser Leu
        195                 200                 205

Tyr Glu Lys Tyr Cys Glu Tyr Ile Arg Thr Tyr Leu Gly Ser Thr Asp
    210                 215                 220

Leu Phe Thr Ala Pro Asp Arg Ile Pro Leu Leu Thr Gly Ile Leu
225                 230                 235                 240

Tyr Asp Phe Cys Lys Glu Tyr Asn Val Phe Tyr Ser Ser Tyr Lys Arg
                245                 250                 255

Asn Val Asp Asn Phe Arg Phe Phe Leu Ala Asn Tyr Met Pro Leu Ile
            260                 265                 270

Ser Asp Val Phe Val Phe Gln Trp Val Lys Pro Ala Pro Asp Val Arg
        275                 280                 285

Leu Leu Phe Glu Leu Ser Ala Ala Glu Leu Thr Leu Glu Val Pro Thr
    290                 295                 300

Leu Ser Leu Ile Asp Ser Gln Val Val Gly His Ile Leu Arg Tyr
305                 310                 315                 320

Val Glu Ser Tyr Thr ser Asp Pro Ala Ile Asp Ala Leu Glu Asp Lys
                325                 330                 335

Leu Glu Ala Ile Leu Lys Ser Ser Asn Pro Arg Leu Ser Thr Ala Gln
            340                 345                 350

Leu Trp Val Gly Phe Phe Cys Tyr Tyr Gly Glu Phe Arg Thr Ala Gln
        355                 360                 365
```

-continued

```
Ser Arg Val Val Gln Arg Pro Gly Val Tyr Lys Thr Pro Asp Ser Val
    370                 375                 380

Gly Gly Phe Glu Ile Asn Met Lys Asp Val Glu Lys Phe Phe Asp Lys
385                 390                 395                 400

Leu Gln Arg Glu Leu Pro Asn Val Ser Leu Arg Arg Gln Phe Asn Gly
                405                 410                 415

Ala Arg Ala His Glu Ala Phe Lys Ile Phe Lys Asn Gly Asn Ile Ser
                420                 425                 430

Phe Arg Pro Ile Ser Arg Leu Asn Val Pro Arg Glu Phe Trp Tyr Leu
            435                 440                 445

Asn Ile Asp Tyr Phe Arg His Ala Asn Arg Ser Gly Leu Thr Glu Glu
            450                 455                 460

Glu Ile Leu Ile Leu Asn Asn Ile Ser Val Asp Val Arg Lys Leu Cys
465                 470                 475                 480

Ala Glu Arg Ala Cys Asn Thr Leu Pro Ser Ala Lys Arg Phe Ser Lys
                485                 490                 495

Asn His Lys Ser Asn Ile Gln Ser Ser Arg Gln Glu Arg Arg Ile Lys
                500                 505                 510

Asp Pro Leu Val Val Leu Lys Asp Thr Leu Tyr Glu Phe Gln His Lys
            515                 520                 525

Arg Ala Gly Trp Gly Ser Arg Ser Thr Arg Asp Leu Gly Ser Arg Ala
        530                 535                 540

Asp His Ala Lys Gly Ser Gly
545                 550
``` and a molecular weight from about 61 to about 65 kDa, preferably about 63 kDa.

Yet another DNA molecule of the present invention (GLRaV-2 ORF5) includes nucleotides 12844-13515 of SEQ. ID. No. 1 and codes for a diverged coat protein. This DNA molecule comprises a nucleotide sequence corresponding to SEQ. ID. No. 12 as follows:

```
ATGAGTTCCA ACACAAGCGT GCCGGTTGGG GGTCTCGAAG CACTCGAGAC CTCGGGAGTC    60
GTGCTGACCA CGCGAAAGGA AGCGGTTGAT AAGTTTTTTA ATGAACTAAA AAACGAAAAT   120
TACTCATCAG TTGACAGCAG CCGATTAAGC GATTCGGAAG TAAAAGAAGT GTTAGAGAAA   180
AGTAAAGAAA GTTTCAAAAG CGAACTGGCC TCCACTGACG AGCACTTCGT CTACCACATT   240
ATATTTTTCT TAATCCGATG TGCTAAGATA TCGACAAGTG AAAAGGTGAA GTACGTTGGT   300
AGTCATACGT ACGTGGTCGA CGGAAAAACG TACACCGTTC TTGACGCTTG GGTATTCAAC   360
ATGATGAAAA GTCTCACGAA GAAGTACAAA CGAGTGAATG GTCTGCGTGC GTTCTGTTGC   420
GCGTGCGAAG ATCTATATCT AACCGTCGCA CCAATAATGT CAGAACGCTT TAAGACTAAA   480
GCCGTAGGGA TGAAAGGTTT GCCTGTTGGA AAGGAATACT TAGGCGCCGA CTTTCTTTCG   540
GGAACTAGCA AACTGATGAG CGATCACGAC AGGGCGGTCT CCATCGTTGC AGCGAAAAAC   600
GCTGTCGATC GTAGCGCTTT CACGGGTGGG GAGAGAAAGA TAGTTAGTTT GTATGATCTA   660
GGGAGGTACT AA                                                      672
```

The diverged coat protein has an amino acid sequence corresponding to SEQ. ID. No. 13 as follows:

```
Met Ser Ser Asn Thr Ser Val Pro Val Gly Gly Leu Glu Ala Leu Glu
1               5                   10                  15

Thr Ser Gly Val Val Leu Thr Thr Arg Lys Glu Ala Val Asp Lys Phe
            20                  25                  30

Phe Asn Glu Leu Lys Asn Glu Asn Tyr Ser Ser Val Asp Ser Ser Arg
        35                  40                  45

Leu Ser Asp Ser Glu Val Lys Glu Val Leu Glu Lys Ser Lys Glu Ser
    50                  55                  60

Phe Lys Ser Glu Leu Ala Ser Thr Asp Glu His Phe Val Tyr His Ile
65              70                  75                  80

Ile Phe Phe Leu Ile Arg Cys Ala Lys Ile Ser Thr Ser Glu Lys Val
                85                  90                  95

Lys Tyr Val Gly Ser His Thr Tyr Val Val Asp Gly Lys Thr Tyr Thr
            100                 105                 110

Val Leu Asp Ala Trp Val Phe Asn Met Met Lys Ser Leu Thr Lys Lys
        115                 120                 125

Tyr Lys Arg Val Asn Gly Leu Arg Ala Phe Cys Cys Ala Cys Glu Asp
    130                 135                 140

Leu Tyr Leu Thr Val Ala Pro Ile Met Ser Glu Arg Phe Lys Thr Lys
145             150                 155                 160

Ala Val Gly Met Lys Gly Leu Pro Val Gly Lys Glu Tyr Leu Gly Ala
            165                 170                 175

Asp Phe Leu Ser Gly Thr Ser Lys Leu Met Ser Asp His Asp Arg Ala
        180                 185                 190

Val Ser Ile Val Ala Ala Lys Asn Ala Val Asp Arg Ser Ala Phe Thr
    195                 200                 205

Gly Gly Glu Arg Lys Ile Val Ser Leu Tyr Asp Leu Gly Arg Tyr
    210                 215                 220
``` and a molecular weight from about 23 to about 27 kDa, preferably about 25 kDa.

Another such DNA molecule ((GTLRaV-2 ORF6) includes nucleotides 13584–14180 of SEQ. ID. No. 1 and codes for a grapevine leafroll virus coat protein. This DNA molecule comprises a nucleotide sequence corresponding to SEQ. ID. No. 14 as follows:

```
ATGGAGTTGA TGTCCGACAG CAACCTTAGC AACCTGGTGA TAACCGACGC CTCTAGTCTA   60

AATGGTGTCG ACAAGAAGCT TTTATCTGCT GAAGTTGAAA AAATGTTGGT GCAGAAAGGG  120

GCTCCTAACG AGGGTATAGA AGTGGTGTTC GGTCTACTCC TTTACGCACT CGCGGCAAGA  180

ACCACGTCTC CTAAGGTTCA GCGCGCAGAT TCAGACGTTA TATTTTCAAA TAGTTTCGGA  240

GAGAGGAATG TGGTAGTAAC AGAGGGTGAC CTTAAGAAGG TACTCGACGG GTGTGCGCCT  300

CTCACTAGGT TCACTAATAA ACTTAGAACG TTCGGTCGTA CTTTCACTGA GGCTTACGTT  360

GACTTTTGTA TCGCGTATAA GCACAAATTA CCCCAACTCA ACGCCGCGGC GGAATTGGGG  420

ATTCCAGCTG AAGATTCGTA CTTAGCTGCA GATTTTCTGG GTACTTGCCC GAAGCTCTCT  480

GAATTACAGC AAAGTAGGAA GATGTTCGCG AGTATGTACG CTCTAAAAAC TGAAGGTGGA  540

GTGGTAAATA CACCAGTGAG CAATCTGCGT CAGCTAGGTA GAAGGGAAGT TATGTAA     597
```

The coat protein has an amino acid sequence corresponding to SEQ. ID. No. 15 as follows:

Met Glu Leu Met Ser Asp Ser Asn Leu Ser Asn Leu Val Ile Thr Asp
1             5                  10                 15

Ala Ser Ser Leu Asn Gly Val Asp Lys Lys Leu Leu Ser Ala Glu Val
                20              25              30

Glu Lys Met Leu Val Gln Lys Gly Ala Pro Asn Glu Gly Ile Glu Val
        35              40                      45

Val Phe Gly Leu Leu Leu Tyr Ala Leu Ala Ala Arg Thr Thr Ser Pro
    50              55                      60

Lys Val Gln Arg Ala Asp Ser Asp Val Ile Phe Ser Asn Ser Phe Gly
65              70                  75                      80

Glu Arg Asn Val Val Thr Glu Gly Asp Leu Lys Lys Val Leu Leu Asp
                85              90                  95

Gly Cys Ala Pro Leu Thr Arg Phe Thr Asn Lys Leu Arg Thr Phe Gly
                100             105                 110

Arg Thr Phe Thr Glu Ala Tyr Val Asp Phe Cys Ile Ala Tyr Lys His
        115                 120                 125

Lys Leu Pro Gln Leu Asn Ala Ala Glu Leu Gly Ile Pro Ala Glu
    130                 135             140

Asp Ser Tyr Leu Ala Ala Asp Phe Leu Gly Thr Cys Pro Lys Leu Ser
145             150                 155                     160

Glu Leu Gln Gln Ser Arg Lys Met Phe Ala Ser Met Tyr Ala Leu Lys
                165                 170                 175

Thr Glu Gly Gly Val Val Asn Thr Pro Val Ser Asn Leu Arg Gln Leu
            180                 185                 190

Gly Arg Arg Glu Val Met
            195 and a molecular weight from about 20 to about 24 kDa, preferably about 22 kDa.

Another such DNA molecule (GLRaV-2 ORF7) includes nucleotides 14180–14665 of SEQ. ID. No. 1 and codes for a second undefined grapevine leafroll virus protein or polypeptide. This DNA molecule comprises a nucleotide sequence corresponding to SEQ. ID. No. 16 as follows:

```
ATGGAAGATT ACGAAGAAAA ATCCGAATCG CTCATACTGC TACGCACGAA TCTGAACACT    60
ATGCTTTTAG TGGTCAAGTC CGATGCTAGT GTAGAGCTGC CTAAACTACT AATTTGCGGT   120
TACTTACGAG TGTCAGGACG TGGGGAGGTG ACGTGTTGCA ACCGTGAGGA ATTAACAAGA   180
GATTTTGAGG GCAATCATCA TACGGTGATC CGTTCTAGAA TCATACAATA TGACAGCGAG   240
TCTGCTTTTG AGGAATTCAA CAACTCTGAT TGCGTAGTGA AGTTTTTCCT AGAGACTGGT   300
AGTGTCTTTT GGTTTTTCCT TCGAAGTGAA ACCAAAGGTA GAGCGGTGCG ACATTTGCGC   360
ACCTTCTTCG AAGCTAACAA TTTCTTCTTT GGATCGCATT GCGGTACCAT GGAGTATTGT   420
TTGAAGCAGG TACTAACTGA AACTGAATCT ATAATCGATT CTTTTTGCGA AGAAAGAAAT   480
CGTTAA                                                              486
```

The second undefined grapevine leafroll virus protein or polypeptide has a deduced amino acid sequence corresponding to SEQ. ID. No. 17 as follows:

Met Glu Asp Tyr Glu Glu Lys Ser Glu Ser Leu Ile Leu Leu Arg Thr
1             5                  10                 15

Asn Leu Asn Thr Met Leu Leu Val Val Lys Ser Asp Ala Ser Val Glu
                20              25              30

Leu Pro Lys Leu Leu Ile Cys Gly Tyr Leu Arg Val Ser Gly Arg Gly

-continued

```
                    35                  40                       45
Glu Val Thr Cys Cys Asn Arg Glu Glu Leu Thr Arg Asp Phe Glu Gly
     50                      55                  60

Asn His His Thr Val Ile Arg Ser Arg Ile Ile Gln Tyr Asp Ser Glu
 65                  70                  75                  80

Ser Ala Phe Glu Glu Phe Asn Asn Ser Asp Cys Val Val Lys Phe Phe
             85                      90                  95

Leu Glu Thr Gly Ser Val Phe Trp Phe Leu Arg Ser Glu Thr Lys
            100                 105                 110

Gly Arg Ala Val Arg His Leu Arg Thr Phe Phe Glu Ala Asn Asn Phe
            115                 120                 125

Phe Phe Gly Ser His Cys Gly Thr Met Glu Tyr Cys Leu Lys Gln Val
            130                 135                 140

Leu Thr Glu Thr Glu Ser Ile Ile Asp Ser Phe Cys Glu Glu Arg Asn
145                 150                 155                 160

Arg
``` and a molecular weight from about 17 to about 21 kDa, preferably about 19 kDa.

Yet another such DNA molecule (GLRaV-2 ORF8) includes nucleotides 14667–15284 of SEQ. ID. No. 1 and codes for a third undefined grapevine leafroll virus protein or polypeptide. This DNA molecule comprises a nucleotide sequence corresponding to SEQ. ID. No. 18 as follows:

```
ATGAGGGTTA TAGTGTCTCC TTATGAAGCT GAAGACATTC TGAAAAGATC GACTGACATG    60
TTACGAAACA TAGACAGTGG GGTCTTGAGC ACTAAAGAAT GTATCAAGGC ATTCTCGACG   120
ATAACGCGAG ACCTACATTG TGCGAAGGCT TCCTACCAGT GGGGTGTTGA CACTGGGTTA   180
TATCAGCGTA ATTGCGCTGA AAAAGCTTTA ATTGACACGG TGGAGTCAAA CATACGGTTG   240
GCTCAACCTC TCGTGCGTGA AAAAGTGGCG GTTCATTTTT GTAAGGATGA ACCAAAAGAG   300
CTAGTAGCAT TCATCACGCG AAAGTACGTG GAACTCACGG GCGTGGGAGT GAGAGAAGCG   360
GTGAAGAGGG AAATGCGCTC TCTTACCAAA ACAGTTTTAA ATAAAATGTC TTTGGAAATG   420
GCGTTTTACA TGTCACCACG AGCGTGGAAA AACGCTGAAT GGTTAGAACT AAAATTTTCA   480
CCTGTGAAAA TCTTTAGAGA TCTGCTATTA GACGTGGAAA CGCTCAACGA ATTGTGCGCC   540
GAAGATGATG TTCACGTCGA CAAAGTAAAT GAGAATGGGG ACGAAAATCA CGACCTCGAA   600
CTCCAAGACG AATGTTAA                                                  618
```

The third undefined protein or polypeptide has a deduced amino acid sequence corresponding to SEQ. ID. No. 19 as follows:

```
Met Arg Val Ile Val Ser Pro Tyr Glu Ala Glu Asp Ile Leu Lys Arg
 1                   5                  10                  15

Ser Thr Asp Met Leu Arg Asn Ile Asp Ser Gly Val Leu Ser Thr Lys
             20                  25                  30

Glu Cys Ile Lys Ala Phe Ser Thr Ile Thr Arg Asp Leu His Cys Ala
             35                  40                  45

Lys Ala Ser Tyr Gln Trp Gly Val Asp Thr Gly Leu Tyr Gln Arg Asn
         50                  55                  60

Cys Ala Glu Lys Arg Leu Ile Asp Thr Val Glu Ser Asn Ile Arg Leu
 65                  70                  75                  80

Ala Gln Pro Leu Val Arg Glu Lys Val Ala Val His Phe Cys Lys Asp
                 85                  90                  95
```

-continued

```
Glu Pro Lys Glu Leu Val Ala Phe Ile Thr Arg Lys Tyr Val Glu Leu
            100                 105                 110

Thr Gly Val Gly Val Arg Glu Ala Val Lys Arg Glu Met Arg Ser Leu
        115                 120                 125

Thr Lys Thr Val Leu Asn Lys Met Ser Leu Glu Met Ala Phe Tyr Met
    130                 135                 140

Ser Pro Arg Ala Trp Lys Asn Ala Glu Trp Leu Glu Leu Lys Phe Ser
145                 150                 155                 160

Pro Val Lys Ile Phe Arg Asp Leu Leu Leu Asp Val Glu Thr Leu Asn
                165                 170                 175

Glu Leu Cys Ala Glu Asp Asp Val His Val Asp Lys Val Asn Glu Asn
            180                 185                 190

Gly Asp Glu Asn His Asp Leu Glu Leu Gln Asp Glu Cys
        195                 200                 205
``` and a molecular weight from about 22 to about 26 kDa, preferably about 24 kDa.

Another DNA molecule of the present invention (GLRaV-2 3' UTR) includes nucleotides 15285–15500 of SEQ. ID. No. 1 and comprises a nucleotide sequence corresponding to SEQ. ID. No. 23 as follows:

conjugated to a signal (or leader) sequence at the N-terminal end of the protein which co-translationally or post-translationally directs transfer of the protein. The nucleotide sequence may also be altered so that the encoded polypeptide is conjugated to a linker or other sequence for ease of synthesis, purification, or identification of the polypeptide.

```
ACATTGGTTA AGTTTAACGA AAATGATTAG TAAATAATAA ATCGAACGTG GGTGTATCTA   60

CCTGACGTAT CAACTTAAGC TGTTACTGAG TAATTAAACC AACAAGTGTT GGTGTAATGT  120

GTATGTTGAT GTAGAGAAAA ATCCGTTTGT AGAACGGTGT TTTTCTCTTC TTTATTTTTA  180

AAAAAAAAAT AAAAAAAAAA AAAAAAAAGC GGCCGC                              216
```

Also encompassed by the present invention are fragments of the DNA molecules of the present invention. Suitable fragments capable of imparting grapevine leafroll resistance to grape plants are constructed by using appropriate restriction sites, revealed by inspection of the DNA molecule's sequence, to: (i) insert an interposon (Felley et al., "Interposon Mutagenesis of Soil and Water Bacteria: a Family of DNA Fragments Designed for in vitro Insertion Mutagenesis of Gram-negative Bacteria," *Gene,* 52:147–15 (1987), which is hereby incorporated by reference) such that truncated forms of the grapevine leafroll virus coat polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Suitable DNA molecules are those that hybridize to a DNA molecule comprising a nucleotide sequence of at least 15 continuous bases of SEQ. ID. No. 1 under stringent conditions characterized by a hybridization buffer comprising 0.9M sodium citrate ("SSC") buffer at a temperature of 37° C. and remaining bound when subject to washing with SSC buffer at 37° C.; and preferably in a hybridization buffer comprising 20% formamide in 0.9M saline/0.9M SSC buffer at a temperature of 42° C. and remaining bound when subject to washing at 42° C. with 0.2×SSC buffer at 42° C.

Variants may also (or alternatively) be modified by, for example, the deletion or addition of nucleotides that have minimal influence on the properties, secondary structure and hydropathic nature of the encoded polypeptide. For example, the nucleotides encoding a polypeptide may be The protein or polypeptide of the present invention is preferably produced in purified form (preferably, at least about 80%, more preferably 90%, pure) by conventional techniques. Typically, the protein or polypeptide of the present invention is isolated by lysing and sonication. After washing, the lysate pellet is resuspended in buffer containing Tris-HCl. During dialysis, a precipitate forms from this protein solution. The solution is centrifuged, and the pellet is washed and resuspended in the buffer containing Tris-HCl. Proteins are resolved by electrophoresis through an SDS 12% polyacrylamide gel.

The DNA molecule encoding the grapevine leafroll virus (type 2) protein or polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference), and any derivatives thereof. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA, in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various grapevine leafroll virus (type 2) proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various grapevine leafroll virus (type 2) proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a grapevine leafroll virus (type 2) to transform grape plants in order to impart grapevine leafroll resistance to the plants. The mechanism by which resistance is imparted is not known. In one hypothetical mechanism, the transformed plant can express a protein or polypeptide of grapevine leafroll virus (type 2), and, when the transformed plant is inoculated by a grapevine leafroll virus, such as GLRaV-1, GLRaV-2, GLRav-3, GLRaV-4, GLRaV-5, or GLRaV-6, or combinations of these, the expressed protein or polypeptide prevents translation of the viral DNA.

In this aspect of the present invention the subject DNA molecule incorporated in the plant can be constitutively expressed. Alternatively, expression can be regulated by a promoter which is activated by the presence of grapevine leafroll virus. Suitable promoters for these purposes include those from genes expressed in response to grapevine leafroll virus infiltration.

The isolated DNA molecules of the present invention can be utilized to impart grapevine leafroll virus resistance for a wide variety of grapevine plants. The DNA molecules are particularly well suited to imparting resistance to Vitis scion or rootstock cultivars. Scion cultivars which can be protected include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gramay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R #1), Harrnony, Kober 5BB, LN33, Millardet & de Grasset 41B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, Vitis rupestris Constantia, *Vitis California*, and *Vitis girdiana.*

There exists an extensive similarity in the hsp70-related sequence regions of GLRaV-2 and other closteroviruses, such as tristeza virus and beet yellows virus. Consequently, the GLRaV-2 hsp70-related gene can also be used to produce transgenic plants or cultivars other than grape, such as citrus or sugar beet, which are resistant to closteroviruses other than grapevine leafroll, such as tristeza virus and beet yellows virus.

Suitable citrus cultivars include lemon, lime, orange, grapefruit, pineapple, tangerine, and the like, such as Joppa, Maltaise Ovale, Parson (Parson Brown), Pera, Pineapple, Queen, Shamouti, Valencia, Tenerife, Imperial Doblefina, Washington Sanguine, Moro, Sanguinello Moscato, Spanish Sanguinelli, Tarocco, Atwood, Australian, Bahia, Baiana, Cram, Dalmau, Eddy, Fisher, Frost Washington, Gillette, LengNavelina, Washington, Satsuma Mandarin, Dancy, Robinson, Ponkan, Duncan, Marsh, Pink Marsh, Ruby Red, Red Seedless, Smooth Seville, Orlando Tangelo, Eureka, Lisbon, Meyer Lemon, Rough Lemon, Sour Orange, Persian Lime, West Indian Lime, Bearss, Sweet Lime, Troyer Citrange, and Citrus Trifoliata. Each of these citrus cultivars is suitable for producing transgenic citrus plants resistant to tristeza virus.

The economically important species of sugar beet is *Beta vulgaris* L., which has four important cultivar types: sugar beet, table beet, fodder beet, and Swiss chard. Each of these beet cultivars is suitable for producing transgenic beet plants resistant to beet yellows virus, as described above.

Because GLRaV-2 has been known to infect tobacco plants (e.g., *Nicotiana benthamiana*), it is also desirable to produce transgenic tobacco plants which are resistant to grapevine leafroll viruses, such as GLRaV-2.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart grapevine leafroll virus resistance. Transformed cells can be regenerated into whole plants such that the protein or polypeptide imparts resistance to grapevine leafroll virus in the intact transgenic plants. In either case, the plant cells transformed with the recombinant DNA expression system of the present invention are grown and caused to express that DNA molecule to produce one of the above-described grapevine leafroll virus proteins or polypeptides and, thus, to impart grapevine leafroll virus resistance.

In producing transgenic plants, the DNA construct in a vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

One technique of transforming plants with the DNA molecules in accordance with the present invention is by contacting the tissue of such plants with an inoculum of a bacteria transformed with a vector comprising a gene in accordance with the present invention which imparts grapevine leafroll resistance. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. Agrobacterium tumefaciens (e.g., strains C58, LBA4404, or EHA105) is particularly useful due to its well-known ability to transform plants.

Heterologous genetic sequences can be introduced into appropriate plant cells, by means of the Ti plasmid of *A.*

*tumefaciens* or the Ri plasmid of *A. rhizogenes*. The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports*, 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Once a grape plant tissue, citrus plant tissue, beet plant tissue, or tobacco plant tissue is transformed in accordance with the present invention, the transformed tissue is regenerated to form a transgenic plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop tissue culture and are screened for marker gene activity.

The DNA molecules of the present invention can be made capable of transcription to a messenger RNA, which, although encoding for a grapevine leafroll virus (type 2) protein or polypeptide, does not translate to the protein. This is known as RNA-mediated resistance. When a Vitis scion or rootstock cultivar, or a citrus, beet, or i-tobacco cultivar, is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

A portion of one or more DNA molecules of the present invention as well as other DNA molecules can be used in a transgenic grape plant, citrus plant, beet plant, or tobacco plant in accordance with U.S. patent application Ser. No. 09/025,635, which is hereby incorporated herein by reference.

The grapevine leafroll virus (type 2) protein or polypeptide of the present invention can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature,* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.,* 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, New York:Academic Press, pp. 98–118 (1983), which is hereby incorporated by reference.

The present invention also relates to probes found either in nature or prepared synthetically by recombinant DNA procedures or other biological procedures. Suitable probes are molecules which bind to grapevine leafroll (type 2) viral antigens identified by the monoclonal antibodies of the present invention. Such probes can be, for example, proteins, peptides, lectins, or nucleic acid probes.

The antibodies or binding portions thereof or probes can be administered to grapevine leafroll virus infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by grapevine leafroll virus. In either case, the antibody or binding portion thereof or probe will bind to the virus and help prevent the usual leafroll response.

Antibodies raised against the GLRaV-2 proteins or polypeptides of the present invention or binding portions of these antibodies can be utilized in a method for detection of grapevine leafroll virus in a sample of tissue, such as tissue (e.g., scion or rootstock) from a grape plant or tobacco plant. Antibodies or binding portions thereof suitable for use in the detection method include those raised against a helicase, a methyltransferase, a papain-like protease, an RNA-dependent RNA polymerase, a heat shock 70 protein, a heat shock 90 protein, a coat protein, a diverged coat protein, or other proteins or polypeptides in accordance with the present invention. Any reaction of the sample with the antibody is detected using an assay system which indicates the presence of grapevine leafroll virus in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, grapevine leafroll virus can be detected in such a sample using a nucleotide sequence of the DNA molecule, or a fragment thereof, encoding for a protein or polypeptide of the present invention. The nucleotide sequence is provided as a probe in a nucleic acid hybridization assay or a gene amplification detection procedure (e.g., using a polymerase chain reaction procedure). The nucleic acid probes of the present invention may be used in any nucleic acid hybridization assay system known in the art, including, but not limited to, Southern blots (Southern, E. M., "Detection of Specific Sequences Among DNA Fragments Separated by Gel Electrophoresis," *J. Mol. Biol.,* 98:503–17 (1975), which is hereby incorporated by reference), Northern blots (Thomas, P. S., "Hybridization of Denatured RNA and Small DNA Fragments Transferred to Nitrocellulose," *Proc. Nat'l Acad. Sci. USA,* 77:5201–05 (1980), which is hereby incorporated by reference), and Colony blots (Grunstein, M., et al., "Colony Hybridization: A Method for the Isolation of Cloned cDNAs that Contain a Specific Gene," *Proc. Nat'l Acad. Sci. USA,* 72:3961–65 (1975), which is hereby incorporated by reference). Alternatively, the probes can be used in a gene amplification detection procedure (e.g., a polymerase chain reaction). Erlich, H. A., et. al., "Recent Advances in the Polymerase Chain Reaction," *Science* 252:1643–51 (1991), which is hereby incorporated by reference. Any reaction with the probe is detected so that the presence of a grapevine leafroll virus in the sample is indicated. Such detection is facilitated by providing the probe of the present invention with a label. Suitable labels include a radioactive compound, a fluorescent compound, a chemiluminescent compound, an enzymatic compound, or other equivalent nucleic acid labels.

Depending upon the desired scope of detection, it is possible to utilize probes having nucleotide sequences that correspond with conserved or variable regions of the ORF or UTR. For example, to distinguish a grapevine leafroll virus from other related viruses (e.g., other closteroviruses), it is desirable to use probes which contain nucleotide sequences that correspond to sequences more highly conserved among all grapevine leafroll viruses. Also, to distinguish between different grapevine leafroll viruses (i.e., GLRaV-2 from GLRaV-1, GLRaV-3, GLRaV-4, GLRaV-5, and GLRaV-6), it is desirable to utilize probes containing nucleotide sequences that correspond to sequences less highly conserved among the different grapevine leafroll viruses.

Nucleic acid (DNA or RNA) probes of the present invention will hybridize to complementary GLRaV-2 nucleic acid under stringent conditions. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° C. + (18.5 \times \text{Log}[Na+]) \\ + (58.4° C. \times \%[G+C]) \\ - (820/\#bp \text{ in duplex}) \\ - (0.5 \times \% \text{ formamide})$$

Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions

EXAMPLES

The following examples are provided to illustrate embodiments of the present invention but are by no means intended to limit its scope.

Example 1
Northern Hybridization

Specificity of the selected clones was confirmed by Northern hybridization.

Northern hybridization was performed after electrophoresis of the dsRNA of GLRaV-2 in 1% agarose non-denaturing condition gel. The agarose gel was denatured by soaking in 50 mM NaOH containing 0.4 M NaCl for 30 min, and then neutralized with 0.1 M Tris-HCl (PH7.5) containing 0.5 M NaCl for another 30 min. RNA was sandwich blotted overnight onto Genescreen™ plus membrane (Dupont NEN Research Product) in 10×SSC buffer and hybridized as described by the manufacturer's instructions (DuPont, NEN).

Example 2
Sequencing and Computer Assisted Nucleotide and

Amino Acid Sequence Analysis DNA inserts were sequenced in pBluescript SK+ by using T3 and T7 universal primers for the terminal region sequence and additional oligonucleotide primers designed according to the known sequence for the internal region sequence. Purification of plasmid DNA was performed by a modified mini alkaline-lysis/PEG precipitation procedure described by the manufacturer (Applied Biosystems, Inc.). Nucleotide sequencing was performed on both strands of cDNA by using ABI TaqDyeDeoxy Terminator Cycle Sequencing Kit (Applied Biosystems, Inc.). Automatic sequencing was performed on an ABI373 Automated Sequencer (Applied Biosynstems, Inc.) at Cornell University, Geneva, N.Y.

The nucleotide sequences of GLRaV-2 were assembled and analyzed with the programs of EditSeq and SeqMan, respectively, of DNASTAR package (Madison, WI). Amino acid sequences deduced from nucleotide sequences and its encoding open reading frames were conducted using the MapDraw program. Multiple alignments of amino acid sequences, identification of consensus amino acid sequences, and generation of phylogenetic trees were performed using the Clustal method in the MegAlign program. The nucleotide and amino acid sequences of other closteroviruses were obtained with the Entrez Program; and sequence comparisons with nonredundant databases were searched with the Blast Program from the National Center for Biotechnology Information.

Example 3
Isolation of dsRNA

Several vines of GLRaV-2 infected *Vitis vinifera* cv Pinot Noir that originated from a central New York vineyard served as the source for dsRNA isolation and cDNA cloning. dsRNA was extracted from phloem tissue of infected grapevines according to the method described by Hu et al., "Characterization of Closterovirus-Like Particles Associated with Grapevine Leafroll Disease," *J. Phytopathology* 128:1–14 (1990), which is hereby incorporated by reference. Purification of the high molecular weight dsRNA (ca 15 kb) was carried out by electrophoretic separation of the total dsRNA on a 0.7% low melting point agarose gel and extraction by phenol/chloroform following the method described by Sambrook et al., *Molecular Cloning: A Laboratory Manual,* 2nd ed., Cold Sping Harbor Laboratory Press, New York (1989), which is hereby incorporated by reference. Concentration of dsRNA was estimated with UV fluorescent density of an ethidium bromide stained dsRNA band in comparison with a known concentration of DNA marker.

Example 4
cDNA Synthesis and Cloning cDNA synthesis was performed following the method initially described by Jelkmann et al., "Cloning of Four Plant Viruses From Small Quantities of Double-Stranded RNA," *Phytopathology* 79:1250–53 (1989) and modified by Ling et al., "The Coat Protein Gene of Grapevine Leafroll Associated Closterovirus-3: Cloning, Nucleotide Sequencing and Expression in Transgenic Plants," *Arch. Virology* 142:1101–16 (1997), both of which are hereby incorporated by reference. About 100 ng of high molecular weight dsRNA purified from low melting agarose gel was denatured in 20 mM methylmercuric hydroxide and incubated at room temperature for 10 min with 350 ng of random primers. First strand cDNA was synthesized by using avian myeloblastosis virus (AMV) reverse transcriptase. Second strand cDNA was obtained by using RNase H and *E. coli* DNA polymerase I. Double-stranded cDNA was blunt ended with T4 DNA polymerase and ligated with EcoR I adapters. The cDNA, which had EcoR I adapters at the ends, was activated by kinase reaction and ligated into Lambda ZAP II/EcoR I prepared arms following the manufacturer's instruction (Stratagene). The recombinant DNA was then packaged in vitro to Gigapack® II packaging extract (Stratagene). The packaged phage particles were amplified and titered according to the manufacturer's instruction.

Two kinds of probes were used to identify GLRaV-2 specific clones from the library. One type was prepared from the synthesized cDNA that was amplified by PCR after ligation to the specific EcoR I Uni-Amp™ adapters (Clontech); and the other type was DNA inserts or PCR products from already sequenced clones. Clones from the cDNA library were selected by colony-lifting hybridization onto the colony/plaque Screen membrane (NEN Research Product) with the probe described above. The probe was prepared by labeling with $^{32}$P [(α-dATP] using Klenow fragment of *E. coli* DNA polymerase I. Prehybridization, hybridization, and washing steps were carried out at 65° C. according to the manufacturer's instruction (Dupont, NEN Research Product). Selected plaques were converted to recombinant pBluescript by in vivo excision method according to the manufacturer's instruction (Stratagene).

To obtain clones representing the extreme 3'-terminus of GLRaV-2, dsRNA was polyadenylated by yeast poly(A) polymerase. Using poly(A)-tailed dsRNA as template, cDNA was amplified by RT-PCR with oligo(dT)18 and a specific primer, CP-1/T7R, which is derived from the clone CP-1 and has a nucleotide sequence according to SEQ. ID. No. 20 as follows:

TGCTGGAGCT TGAGGTTCTG C 21

The resulting PCR product (3'-PCR) was cloned into a TA vector (Invitrogen) and sequenced.

As shown in FIG. 1A, a high molecular weight dsRNA of ca. 15 kb was consistently identified from GLRaV-2 infected grapevines, but not from healthy vines. In addition, several low molecular weight dsRNAs were also detected from infected tissue. The yield of dsRNA of GLRaV-2 was estimated between 5–10 ng/15 g phloem tissue, which was much lower than that of GLRaV-3 (Hu et al., "Characterization of Closterovirus-Like Particles Associated with Grapevine Leafroll Disease," *J. Phytopathology* 128:1–14 (1990), which is hereby incorporated by reference). Only the high molecular weight dsRNA that was purified from low melting point agarose gel was used for cDNA synthesis, cloning and establishment of the Lambda/ZAP II cDNA library.

Figure 1B:
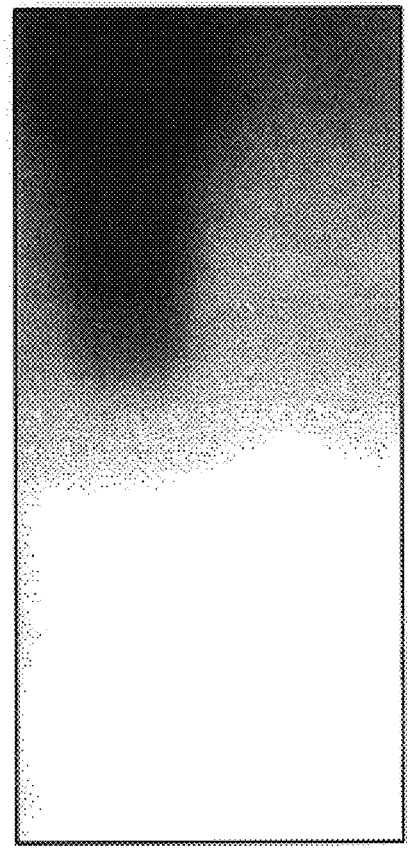
Figure 2:
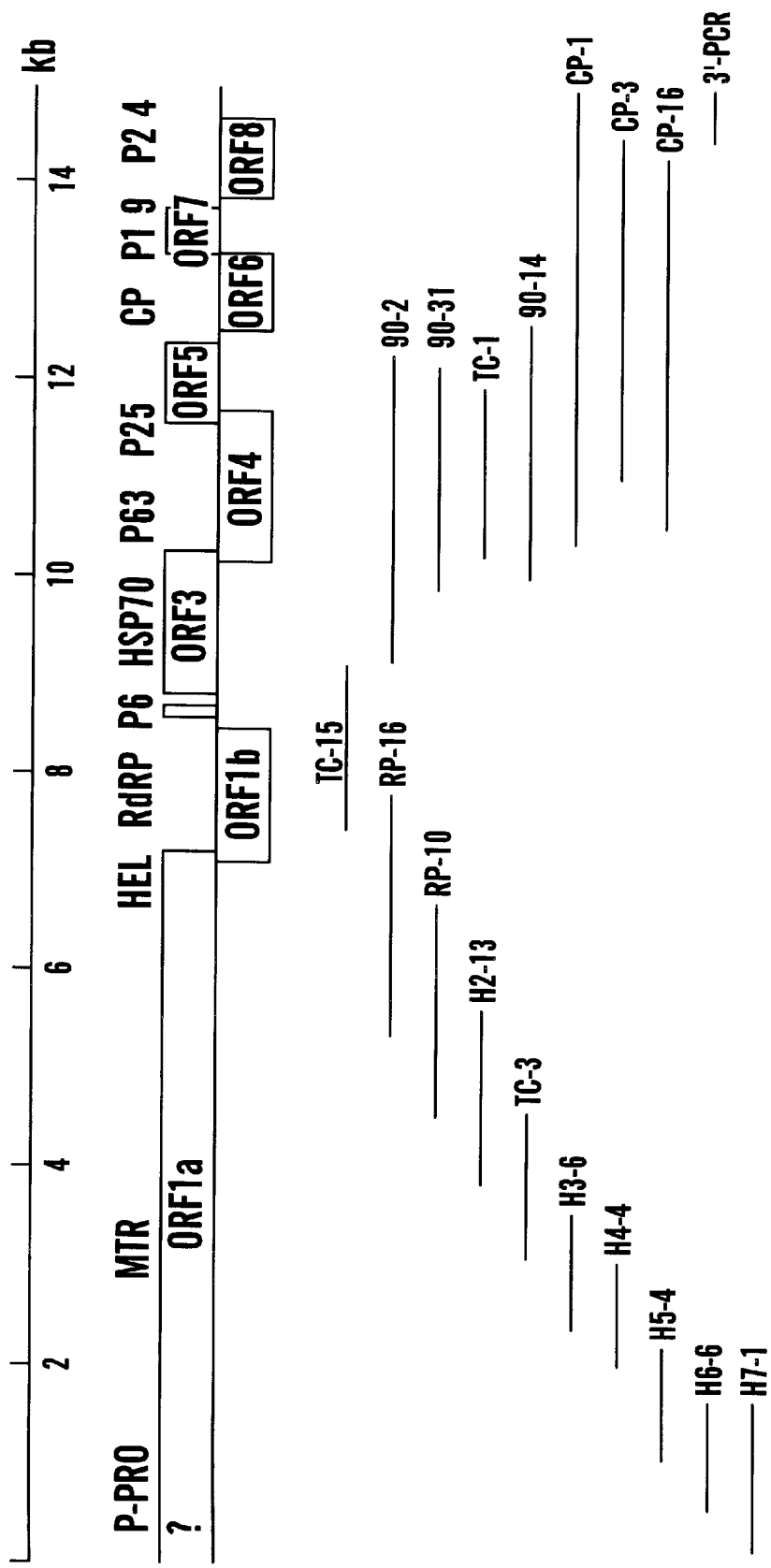
FIG. 2 displays the genome organization of GLRaV-2 and its sequencing strategy. Boxes represent ORFs encoded by deduced amino acid sequences of GLRaV-2, numbered lines represent nucleotide coordinates, beginning from 5'-terminal of RNA in kilobases (kb). The lines below GLRaV-2 RNA genome represent the cDNA clones used to determine the nucleotide sequences.

Two kinds of probes were used for screening the cDNA library. The initial clones were identified by hybridization with Uni-Amp™ PCR-amplified cDNA as probes. The specificity of these clones (e.g., TC-1) ranging from 200 to 1,800 bp in size was confirmed by Northern hybridization to dsRNA of GLRaV-2 as shown in FIG. 1B. Additionally, over 40 different clones ranging form 800 to 7,500 bp in size were identified following hybridization with the probes generated from GLRaV-2 specific cDNA clones or from PCR products. Over 40 clones were then sequenced on the both strands (FIG. 2).

Example 5

Expression of the Coat Protein in *E. coli* and Immunoblotting

To determine that ORF6 was the coat protein gene of GLRaV-2, the complete ORF6 DNA molecule was subcloned from a PCR product and inserted into the fusion protein expression vector pMAL-C2 (New England Biolabs, Inc.). The specific primers used for the PCR reaction were CP-96F and CP-96R, in which an EcoR I or BamH I site was included to facilitate cloning. CP-96F was designed to include the start codon of the CP and comprises a nucleotide sequence according to SEQ. ID. NO. 21 as follows:

CGGAATTCAC CATGGAGTTG ATGTCCGACA G        31

CP-96R was 66 nucleotides downstream of the stop codon of the CP and comprises the nucleotide sequence corresponding to SEQ. ID. No. 22 as follows:

AGCGGATCCA TGGCAGATTC GTGCGTAGCA GTA        33

The coat protein was expressed as a fusion protein with maltose binding protein (MBP) of *E. coli* under the control of a "tac" promoter and suppressed by the "lac" repressor. The MBP-CP fusion protein was induced by adding 0.3 mM isopropyl-p-D-thio-gloactopyranoside (IPTG) and purified by a one step affinity column according to the manufacturer's instruction (New England, Biolabs, Inc ). The MBP-CP fusion protein or the coat protein cleaved from the fusion protein was tested to react with specific antiserum of GLRaV-2 (kindly provided by Dr. Charles Greif of INRA, Colmar, France) on Western blot according to the method described by Hu et al., "Characterization of Closterovirus-Like Particles Associated with Grapevine Leafroll Disease," *J. Phytopathology* 128:1–14 (1990), which is hereby incorporated by reference. In contrast, the non-recombinant plasmids or uninduced cells did not react to the antiserum of GLRaV-2.

Example 6

Sequence Analysis and Genome Organization of GLRaV-2

A total of 15,500 bp of the RNA genome of GLRaV-2 was sequenced and deposited in GenBank (accession number AF039204). About 85% of the total RNA genome was revealed from at least two different clones. The sequence in the coat protein gene region was determined and confirmed from several different overlapping clones. The genome organization of GLRaV-2, shown in FIG. 2, includes nine open reading frames (e.g., ORF1a, 1b-8).

ORF1a and ORF1b: Analysis of the amino acid sequence of the N-terminal portion of GLRaV-2 ORF1a encoded product revealed two putative papain-like protease domains, which showed significant similarity to the papain-like leader protease of BYV (Agranovsky et al., "Beet Yellows Closterovirus: Complete Genome Structure and Identification of a Papain-like Thiol Protease," *Virology* 198:311–24 (1994), which is hereby incorporated by reference). Thus, it allowed prediction of the catalytic cysteine and histidine residues for the putative GLRaV-2 protease. Upon alignment of the sequence of the papain-like protease of BYV with that of GLRaV-2, the cleavage site at residues Gly-Gly (amino acid 588-589) of BYV aligned with the corresponding alanine-glycine (Ala-Gly) and Gly-Gly dipeptide of GLRaV-2 (FIG. 3A). Cleavage at this site would result in a leader protein and a 234 kDa (2090 amino acid) C-terminal fragment consisting of MT and HEL domains. However, the region upstream of the papain-like protease domain in GLRaV-2 did not show similarity to the corresponding region of BYV. In addition, variability in the residues located at the scissible bond (Gly in the BYV and Ala in the GLRaV-2) was present. Similar variability of the cleavage site residue in the P-PRO domain has been described in LChV (Jelkmann et al., "Complete Genome Structure and Phylogenetic Analysis of Little Cherry Virus, a Mealybug-Transmissible Closterovirus. *J. General Virology* 78:2067–71 (1997), which is hereby incorporated by reference).

Database searching with the deduced amino acid sequence of the ORF1 a/1b encoded protein revealed a significant similarity to the MT, HEL and RdRP domains of the other closteroviruses. The region downstream of the P-PRO cleavage site showed a significant similarity (57.4% identity in a 266-residues alignment) to the putative methyltransferase domain of BYV and contained all the conserved motifs typical of positive-strand RNA viral type I MTs (FIG. 3B). The C-terminal portion of the ORF1a was identified as a helicase domain, the sequence of which showed a high similarity (57.1 % identity in a 315-residues alignment) to the helicase domain of BYV and contained the seven conserved motifs characteristic of the Superfamily I helicase of positive-strand RNA viruses (FIG. 3C) (Hodgman, "A New Superfamily of Replicative Proteins," *Nature* 333:22–23 (1988); Koonin and Dolja, "Evolution and Taxonomy of Positive-strand RNA Viruses: Implications of Comparative Analysis of Amino Acid Sequences," *Crit. Rev. in Biochem. and Mol. Biol.* 28:375–430 (1993), both of which are hereby incorporated by reference).

ORF1b encoded a 460 amino acid polypeptide with a molecular mass of 52,486 Da, counting from the frameshifting site. Database searching with the RdRP showed a significant similarity to the RdRP domains of positive strand RNA viruses. Comparison of the RdRP domains of GLRaV-2 and BYV showed the presence of the eight conserved motifs of RdRP (FIG. 3D).

Figure 8:
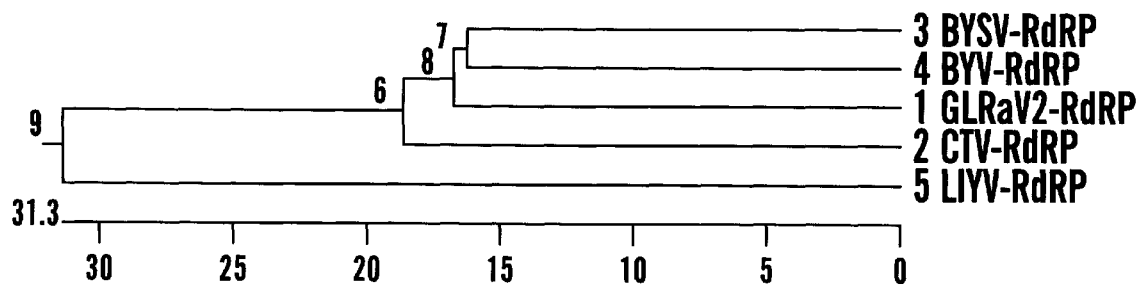
FIG. 8 is a tentative phylogenetic tree showing the relationship of RdRP of GLRaV-2 with respect to BYV, BYSV, CTV, and LIYV. The phylogenetic tree was constructed using the Clustal method with the MegAlign program in DNASTAR.

As shown in FIG. 8, a tentative phylogenetic tree of the RdRP of GLRaV-2 with respect to other closteroviruses shows that it is closely related to the monopartite closteroviruses BYV, BYSV, and CTV.

In closteroviruses, a +1 ribosomal frameshift mechanism has been suggested to be involved in the expression of ORF1b as a large fusion protein with ORF1a (Agranovsky et al., "Beet Yellows Closterovirus: Complete Genome Structure and Identification of a Papain-like Thiol Protease,"

Virology 198:311–24 (1994); Karasev et al., "Complete Sequence of the Citrus Tristeza Virus RNA Genome," Virology 208:511–20 (1995); Klaassen et al., "Genome Structure and Phylogenetic Analysis of Lettuce Infectious Yellows Virus, a Whitefly-Transmitted, Bipartite Closterovirus," Virology 208:99–110 (1995); Karasev et al., "Organization of the 3'-Terminal Half of Beet Yellow Stunt Virus Genome and Implications for the Evolution of Closteroviruses," Virology 221:199–207 (1996); Jelkmann et al., "Complete Genome Structure and Phylogenetic Analysis of Little Cherry Virus, a Mealybug-Transmissible Closterovirus," J. General Virology 78:2067–71 (1997), all of which are hereby incorporated by reference). In the overlapping ORF1a/1b region of BYV, the slippery sequence of GGGU-UUA and two hairpins structure (stem-loop and pseudoknot) are believed to result in a +1 frameshift (Agranovsky et al., "Beet Yellows Closterovirus: Complete Genome Structure and Identification of a Papain-like Thiol Protease," Virology 198:311–24 (1994), which is hereby incorporated by reference). None of these features are conserved in CTV and BYSV (Karasev et al., "Complete Sequence of the Citrus Tristeza Virus RNA Genome," Virology 208:511–20 (1995); Karasev et al., "Organization of the 3'-Terminal Half of Beet Yellow Stunt Virus Genome and Implications for the Evolution of Closteroviruses," Virology 221:199–207 (1996), both of which are hereby incorporated by reference), in which a ribosomal pausing at a terminator or at a rare codon was suggested to perform the same function. Comparisons of the nucleotide sequence of the C-terminal region of the helicase and the N-terminal region of RdRP of GLRaV-2 with the same region of other closteroviruses revealed a significant similarity to BYV, BYSV, and CTV. As shown in FIG. 4, the terminator UAG at the end of C'-terminal helicase of GLRaV-2 aligned with the terminator UAG of BYV and BYSV, and arginine CGG codon of CTV.

ORF2 encodes a small protein consisting of 171 bp (57 amino acid) with a molecular mass of 6,297 Da. As predicted, the deduced amino acid sequence includes a stretch of nonpolar amino acids, which is presumed to form a transmembrane helix. A small hydrophobic analogous protein is also present in BYV, BYSV, CTV, LIYV, and LChV (Agranovsky et al. "Nucleotide Sequence of the 3'-Terminal Half of Beet Yellows Closterovirus RNA Genome Unique Arrangement of Eight Virus Genes," J. General Virology 72:15–24 (1991); Karasev et al., "Organization of the 3'-Terminal Half of Beet Yellow Stunt Virus Genome and Implications for the Evolution of Closteroviruses," Virology 221:199–207 (1996); Pappu et al., "Nucleotide Sequence and Organization of Eight 3' Open Reading Frames of the Citrus Tristeza Closterovirus Genome," Virology 199:35–46 (1994); Klaassen et al., "Partial Characterization of the Lettuce Infectious Yellows Virus Genomic RNAs, Identification of the Coat Protein Gene and Comparison of its Amino Acid Sequence With Those of Other Filamentous RNA Plant Viruses," J. General Virology 75:1525–33 (1994); Jelkmann et al., "Complete Genome Structure and Phylogenetic Analysis of Little Cherry Virus, a Mealybug-Transmissible Closterovirus," J. General Virology 78:2067–71 (1997), all of which are hereby incorporated by reference).

ORF3 encodes a 600 amino acid polypeptide with a molecular mass of 65,111 Da, which is homologous to the HSP70 cellular heat shock protein. HSP70 is highly conserved among closteroviruses and is probably involved in ATPase activity and the protein to protein interaction for chaperone activity (Agranovsky et al. "The Beet Yellows Closterovirus p65 Homologue of HSP70 Chaperones has ATPase Activity Associated with its Conserved N-terminal Domain but Interact with Unfolded Protein Chains," J. General Virology 78:535–42 (1997); Agranovsky et al., "Bacterial Expression and Some Properties of the p65, a Homologue of Cell Heat Shock Protein HSP70 Encoded in RNA Genome of Beet Yellows Closterovirus," Doklady Akademii Nauk. 340:416–18 (1995); Karasev et al., "HSP70-Related 65-kDa Protein of Beet Yellows Closterovirus is a Microtubule-Binding Protein," FEBS Letters 304:12–14 (1992), all of which are hereby incorporated by reference). As shown in FIG. 5, alignment of the complete ORF3 of GLRaV-2 with HSP70 homolog of BYV revealed the presence of the eight conserved motifs. The percentage similarity of the HSP70 between GLRaV-2 and that of BYV, BYSV, CTV, LIYV, and LChV is 47.8%, 47.2%, 38.6%, 20.9%, and 17.7%, respectively.

ORF4 encodes a 551 amino acid protein with a molecular mass of 63,349 Da. Database searching with the ORF4 protein product did not identify similar proteins except those of its counterparts in closteroviruses, BYV (P64), BYSV (P61), CTV (P61), LIYV (P59), and LChV (P61). This protein is believed to be a putative heat shock 90 protein. As shown in FIG. 9, two conserved motifs which were present in BYV (Agranovsky et al. "Nucleotide Sequence of the 3'-Terminal Half of Beet Yellows Closterovirus RNA Genome Unique Arrangement of Eight Virus Genes," J. General Virology 72:15-24 (1991), which is hereby incorporated by reference) and CTV (Pappu et al., "Nucleotide Sequence and Organization of Eight 3' Open Reading Frames of the Citrus Tristeza Closterovirus Genome," Virology 199:35–46 (1994), which is hereby incorporated by reference) were also identified in the ORF4 of GLRaV-2.

ORF5 and ORF6 encode polypeptides with molecular mass of 24,803 Da and 21,661 Da, respectively. The start codon for both ORFs is in a favorable context for translation. ORF6 was identified as the coat protein gene of GLRaV-2 based on the sequence comparison with other closteroviruses. The calculated molecular mass of the protein product of ORF6 (21,662 Da) is in good agreement with the previously estimated 22–26 kDa based on SDS-PAGE (Zimmermann et al., "Characterization and Serological Detection of Four Closterovirus-like Particles Associated with Leafroll Disease on Grapevine," J. Phytopathology 130:205–18 (1990); Boscia et al., "Nomenclature of Grapevine Leafroll-Associated Putative Closteroviruses," Vitis 34:171–75 (1995), both of which are hereby incorporated by reference).

Database searching with the deduced amino acid sequence of the ORF6 of GLRaV-2 showed a similarity with the coat proteins of closteroviruses, BYV, BYSV, CTV, LIYV, LChV, and GLRaV-3. At the nucleotide level, the highest percentage similarity was with the coat protein of BYSV (34.8%); at the amino acid level, the highest percentage similarity was with the coat proteins of BYV (32.7%) and BYSV (32.7%). As shown in FIG. 6A, alignment of the amino acid sequence of the coat protein and coat protein duplicate of GLRaV-2 with respect to other closteroviruses revealed that the invariant amino acid residues (N. R. G. D.) were present in both ORF5 and ORF6 of GLRaV-2. Two of these amino acid residues (R and D) are believed to be involved in stabilization of molecules by salt bridge formation and proper folding in the most conserved core region of coat proteins of all filamentous plant viruses (Dolja et al., "Phylogeny of Capsid Proteins of Rod-Shaped and Filamentous RNA Plant Viruses Two Families With Distinct Patterns of Sequence and Probably Structure Conservation," Virology 184:79–86 (1991), which is hereby incorporated by reference).

Figure 6B:
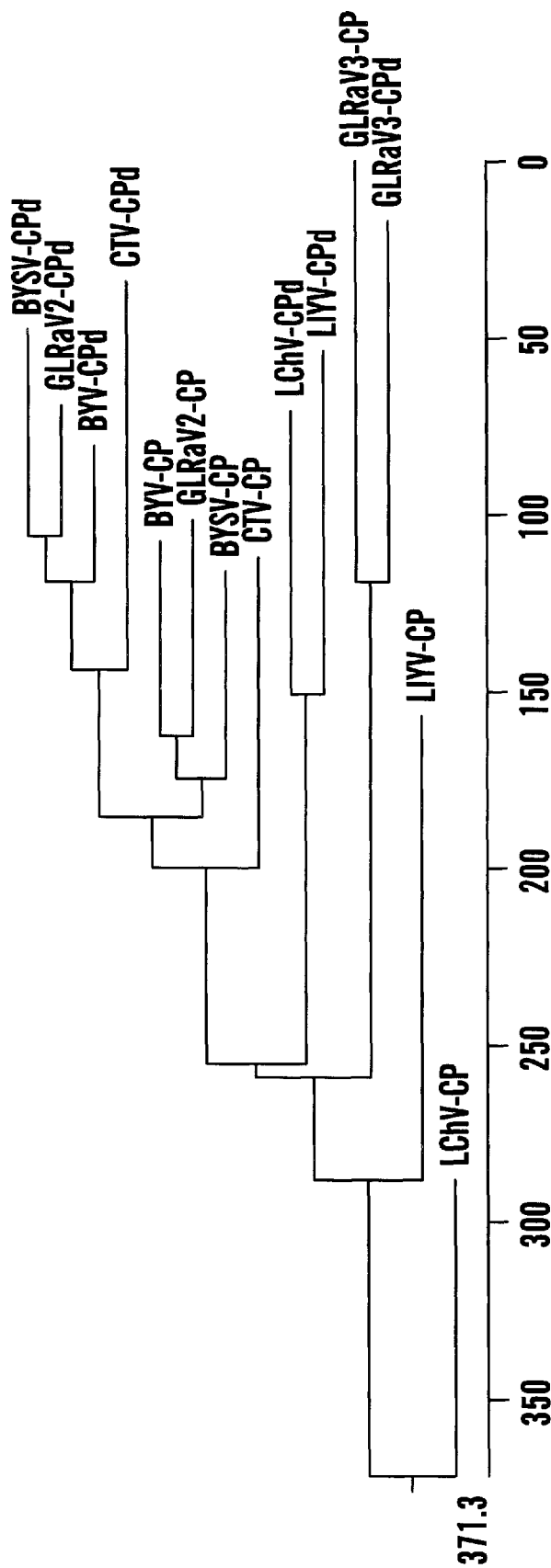

Identification of ORF6 as the coat protein gene was further confirmed by Western blot following expression of a fusion protein, consisting of a 22 kDa of ORF6 CP and a 42 kDa of maltose binding protein, produced by transformed *E. coli* as described in Example 5 supra. As shown in FIG. 6B, the putative phylogenetic tree of the coat protein and coat protein duplicate of GLRaV-2 with those of other closteroviruses showed that GLRaV-2 is more closely related to aphid transmissible closteroviruses (BYV, BYSV, and CTV) (Candresse, "Closteroviruses and Clostero-like Elongated Plant Viruses," in *Encyclopedia of Virology*, pp. 242–48, Webster and Granoff, eds., Academic Press, New York (1994), which is hereby incorporated by reference) than to whitefly (LIYV) or mealybug transmissible closteroviruses (LChV and GLRaV-3) (Raine et al., "Transmission of the Agent Causing Little Cherry Disease by the Apple Mealybug *Phenacoccus aceris* and the Dodder *Cuscuta Lupuliformis*," *Canadian J. Plant Pathology* 8:6–11 (1986); Jelkmann et al., "Complete Genome Structure and Phylogenetic Analysis of Little Cherry Virus, a Mealybug-Transmissible Closterovirus," *J. General Virology* 78:2067–71 (1997); Rosciglione and Gugerli, "Transmission of Grapevine Leafroll Disease and an Associated Closterovirus to Healthy Grapevine by the Mealybug *Planococcus ficus*," *Phytoparasitica* 17:63 (1989); Engelbrecht and Kasdorf, "Transmission of Grapevine Leafroll Disease and Associated Closteroviruses by the Vine Mealybug *planococcus-ficus*," *Phytophlactica*, 22:341–46 (1990); Cabaleiro and Segura, 1997; Petersen and Charles, "Transmission of Grapevine Leafroll-Associated Closteroviruses by *Pseudococcus longispinus* and *P. calceolariae*. *Plant Pathology* 46:509–15 (1997), all of which are hereby incorporated by reference).

Figure 7:
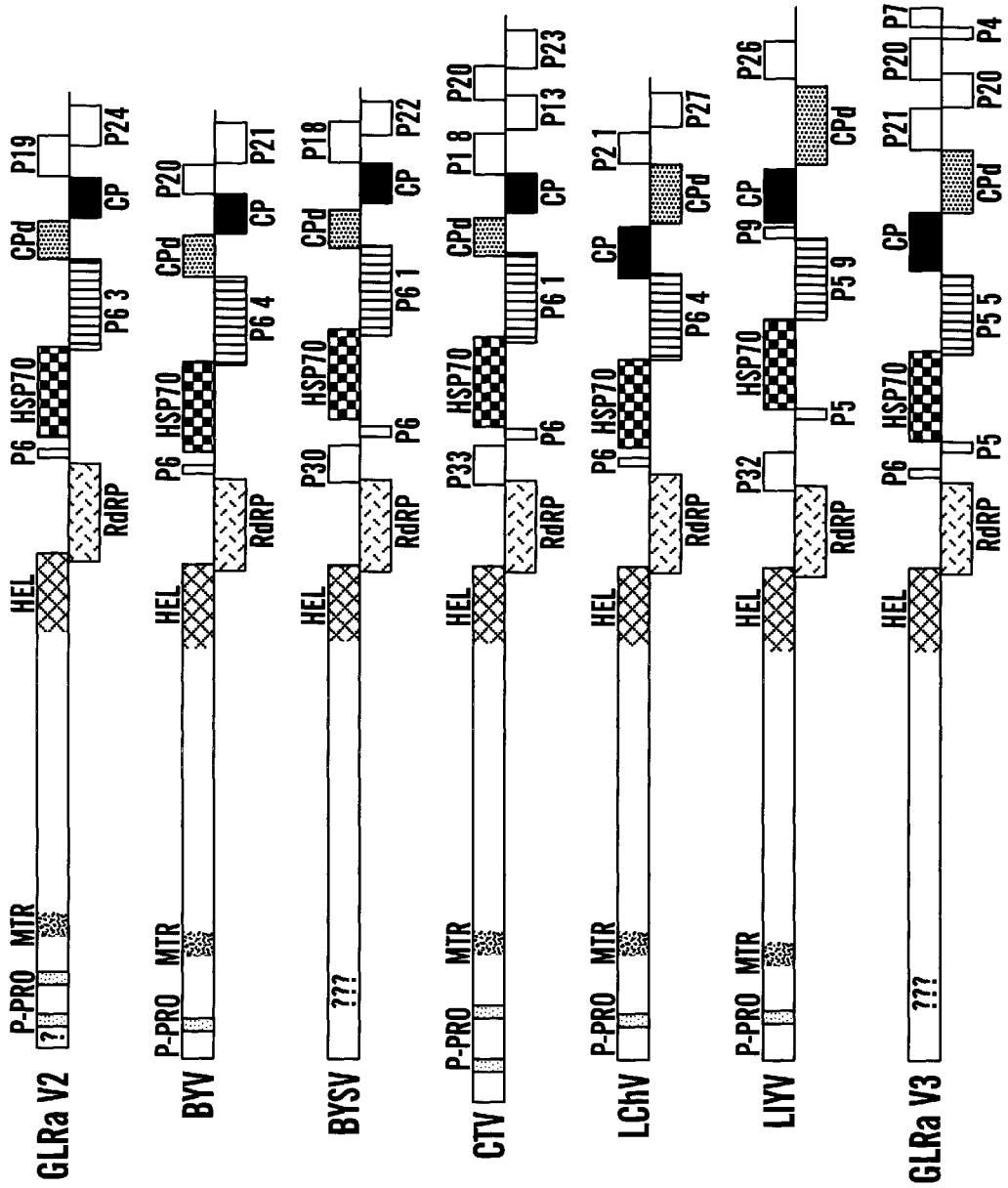
FIG. 7 is a comparison of the genome organization of GLRaV-2, BYV, BYSV, CTV, LIYV, LChV, and GLRaV-3. P-PRO, papain-like protease; MT/MTR, methyltransferase; HEL, helicase; RdRP, RNA-dependent RNA polymerase; HSP70, heat shock protein 70; CP, coat protein; CPd, coat protein duplicate.

ORF7 and ORF8 encode polypeptides of 162 amino acid with a molecular mass of 18,800 Da and of 206 amino acid with a molecular mass of 23,659 Da, respectively. Database searching with the ORF7 and ORF8 showed no significant similarity with any other proteins. Nevertheless, these genes were of similar in size and location as those observed in the sequence of other closteroviruses, BYV (P20, P21), BYSV (P18, P22), and LChV (P21, P27) (FIG. 7). However, conserved regions were not observed between the ORF7 or ORF8 and its counterparts in BYV, BYSV, and LChV.

The 3' terminal untranslated region (3'-UTR) consists of 216 nucleotides. Nucleotide sequence analysis revealed a long oligo(A) tract close to the end of the GLRaV-2 genome which is similar to that observed in the genome of BYV and BYSV (Agranovsky et al. "Nucleotide Sequence of the 3'-Terminal Half of Beet Yellows Closterovirus RNA Genome Unique Arrangement of Eight Virus Genes," *J. General Virology* 72:15–24 (1991); Karasev et al., "Organization of the 3'-Terminal Half of Beet Yellow Stunt Virus Genome and Implications for the Evolution of Closteroviruses," *Virology* 221:199–207 (1996), both of which are hereby incorporated by reference). The genome of BYV ends in CCC, BYSV, and CTV ends in CC with an additional G or A in the double-stranded replicative form of BYSV (Karasev et al., "Organization of the 3'-Terminal Half of Beet Yellow Stunt Virus Genome and Implications for the Evolution of Closteroviruses," *Virology* 221:199–207 (1996), which is hereby incorporated by reference) and CTV (Karasev et al., "Complete Sequence of the Citrus Tristeza Virus RNA Genome," *Virology* 208:511–20 (1995), which is hereby incorporated by reference), respectively. GLRaV-2 had CGC at the 3' terminus of the genome. Recently, a conserved 60 nt cis-element was identified in the 3'-UTR of three monopartite closteroviruses, which included a prominent conserved stem and loop structure (Karasev et al., 1996). As shown in FIG. 10, alignment of the 3'-UTR sequence of GLRaV-2 with the same regions of BYV, BYSV, and CTV showed the presence of the same conserved 60 nt stretch. Besides this cis-element, conserved sequences were not found in the 3' UTRs of GLRaV-2, BYV, BYSV, and CTV.

The closteroviruses studied so far (e.g., BYV, BYSV, CTV, LIYV, LChV, and GLRaV-3) have apparent similarities in genome organization, which include replication associated genes that consist of MT, HEL, and RdRP conserved domains and a five-gene array unique for closteroviruses (Dolja et al. "Molecular Biology and Evolution of Closteroviruses: Sophisticated Build-up of Large RNA Genomes," *Annual Rev. Photopathology* 32:261–85 (1994); Agranovsky "Principles of Molecular Organization, Expression, and Evolution of Closteroviruses: Over the Barriers," *Adv. in Virus Res.* 47:119–218 (1996); Jelkmann et al., "Complete Genome Structure and Phylogenetic Analysis of Little Cherry Virus, a Mealybug-Transmissible Closterovirus," *J. General Virology* 78:2067–71 (1997); Ling et al., "Nucleotide Sequence of the 3' Terminal Two-Thirds of the Grapevine Leafroll Associated Virus-3 Genome Reveals a Typical Monopartite Closterovirus," *J. General Virology* 79(5):1289–1301 (1998), all of which are hereby incorporated by reference).

The above data clearly shows that GLRaV-2 is a closterovirus. In the genome of GLRaV-2, two putative papain-like proteases were identified and an autoproteolytic cleavage process was predicted. The replication associated proteins consisting of MT, HEL, and RdRP conserved motifs were also identified, which were phylogenetically closely related to the replication associated proteins of other closteroviruses. A unique gene array including a small hydrophobic transmembrane protein, HSP70 homolog, HSP90 homolog, diverged CP and CP was also preserved in GLRaV-2. In addition, the calculated molecular mass (21,661 Da) of the coat protein (ORF6) of GLRaV-2 is in good agreement with that of the other closteroviruses (22 to 28 kDa) (Martelli and Bar-Joseph, "Closteroviruses: Classification and Nomenclature of Viruses," *Fifth Report of the International Committee on Taxonomy of Viruses*, Francki et al., eds., Springer-Verlag Wein, New York, p. 345-47 (1991); Candresse and Martelli, "Genus Closterovirus," in *Virus Taxonomy, Report of the International Committee on Taxonomy of Viruses*, Murphy et al., eds., Springer-Verlag., NY, p. 461–63 (1995), both of which are hereby incorporated by reference). Two ORFs downstream of the CP are of similar, in size and location, to those observed in the genome of BYV. Furthermore, lack of a poly(A) tail at the 3' end of GLRaV-2 is also in good agreement with other closteroviruses. Like all other closteroviruses, the expression of ORF1b is suspected to occur via a +1 ribosomal frameshift and the 3'proximal ORFs are probably expressed via formation of a nested set of subgenomic RNAs. Since the slippery sequence, stem-loop and pseudoknot structure involved in the frameshift of BYV were absent in GLRaV-2, the +1 frameshift of GLRaV-2 might be the same as proposed for CTV (Karasev et al., "Complete Sequence of the Citrus Tristeza Virus RNA Genome," *Virology* 208:511–20 (1995), which is hereby incorporated by reference) and BYSV (Karasev et al., "Organization of the 3'-Terminal Half of Beet Yellow Stunt Virus Genome and Implications for the Evolution of Closteroviruses," *Virology* 221:199–207 (1996), which is hereby incorporated by reference).

Overall, GLRaV-2 is more closely related to monopartite closteroviruses BYV, BYSV, and CTV than to GLRaV-3

(FIG. 7) (Ling et al., "Nucleotide Sequence of the 3' Terminal Two-Thirds of the Grapevine Leafroll Associated Virus-3 Genome Reveals a Typical Monopartite Closterovirus," *J. General Virology* 79(5):1289–1301 (1998), which is hereby incorporated by reference), even though the latter causes similar leafroll symptoms in grapevine (Rosciglione and Gugerli, "Maladies de l'Enroulement et du Bois Strie de la Vigne: Analyse Microscopique et Serologique (Leafroll and Stem Pitting of Grapevine: Microscopical and Serological Analysis)," *Rev Suisse Viticult Arboricult Horticulture* 18:207–11 (1986); Hu et al., "Characterization of Closterovirus-Like Particles Associated with Grapevine Leafroll Disease," *J. Phytopathology* 128:1–14 (1990), both of which are hereby incorporated by reference).

Closteroviruses are a diverse group with complex and heterogeneous genome organizations. So far, GLRaV-2 is the only closterovirus that matches with the genome organization of BYV, the type member of the genus Closterovirus. In addition, the genomic RNA of GLRaV-2 is about the same size as that of BYV; however, the transmission vector of GLRaV-2 is unknown. The genome organization of GLRaV-2 is more closely related to the aphid transmissible closteroviruses (BYV and CTV) than to whitefly (LIYV) or mealybug transmissible closteroviruses (LChV and GLRaV-3). Thus, it is possible that GLRaV-2 is transmitted by aphids. Aphid transmission experiments with GLRaV-2 should provide information that might help develop methods for further control of GLRaV-2.

A total of 15,500 nucleotides or over 95% of the estimated GLRaV-2 genome has been cloned and sequenced. GLRaV-2 and GLRaV-3 (Ling et al., "Nucleotide Sequence of the 3' Terminal Two-Thirds of the Grapevine Leafroll Associated Virus-3 Genome Reveals a Typical Monopartite Closterovirus," *J. General Virology* 79(5):1289–1301 (1998), which is hereby incorporated by reference) are the first grapevine leafroll associated closteroviruses that have been almost completely sequenced. The above data clearly justify the inclusion of GLRaV-2 into the genus Closterovirus. In addition, the information regarding the genome of GLRaV-2 would provide a better understanding of this and related GLRaVs, and add fundamental knowledge to the group of closteroviruses.

Example 7
Construction of the CP Gene of GLRaV-2 in Plant Expression Vector

Figure 11A:
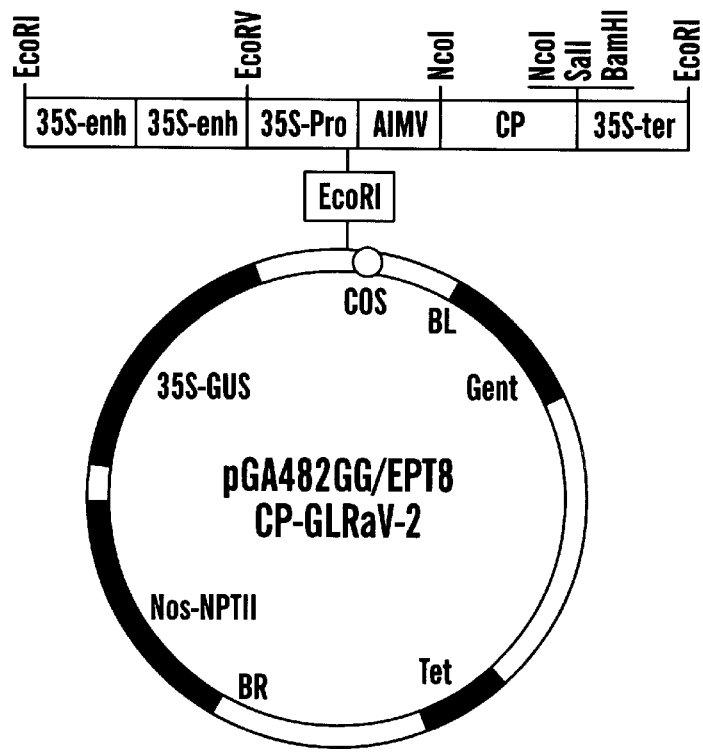
FIGS. 11A and 11B are genetic maps of the transformation vectors pGA482GG/EPT8CP-GLRaV-2 and pGA482G/EPT8CP-GLRaV-2, respectively.
Figure 11B:
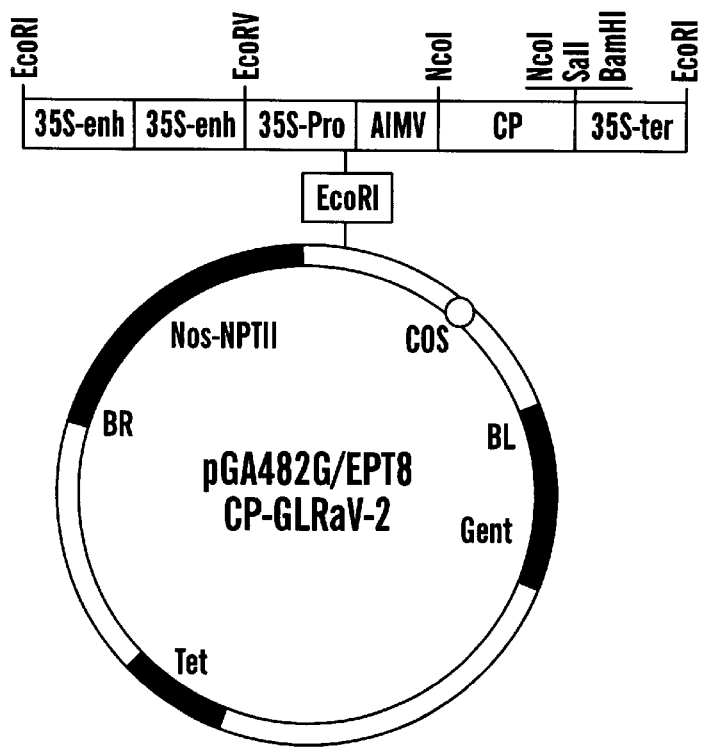
Figure 12:
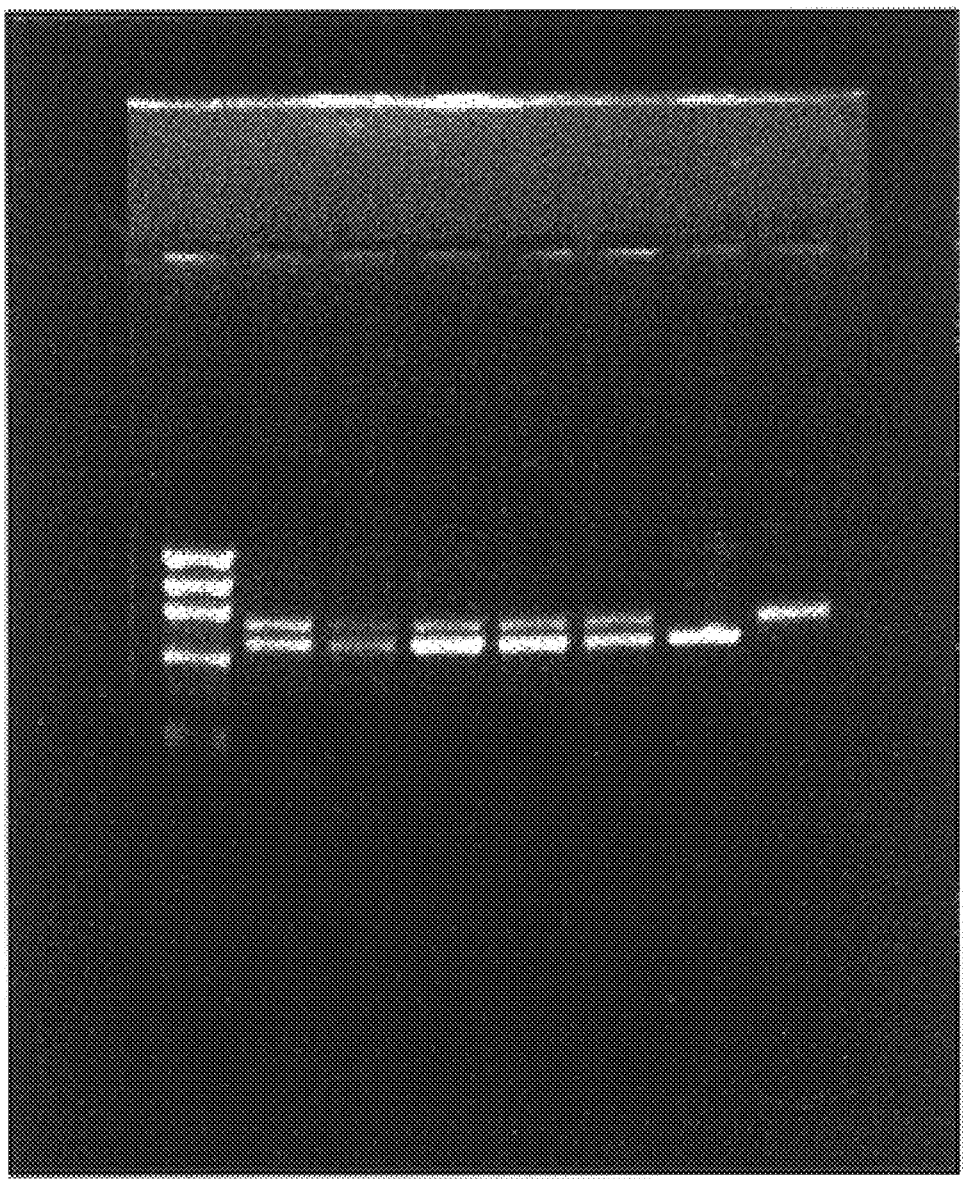
FIG. 12 is a PCR analysis of DNA molecules extracted from the leaves of putative transgenic plants using both the CP gene of GLRaV-2 and NPT II gene specific primers. An ethidium bromide-stained gel shows a 720 bp amplified DNA fragment for NPT II gene, and a 653 bp DNA fragment for the entire coding sequence of the CP gene. Lane 1, (Φ174 /Hae III DNA Marker; lanes 2-6, transgenic plants from different lines; lane 7, the cp gene of GLRaV-2 of positive control; and lane 8, NPT II gene of positive control.
Figure 13:
FIG. 13 is a comparison of resistant (right side 3 plants) and susceptible (left side 3 plants) transgenic Nicotiana benthamiana plants. Plants are shown 48 days after inoculation with GLRaV-2.

GLRaV-2 infected *Vitis vinifera*, cv Pinot Noir grapevines originated from a vineyard in central New York was used as the virus isolate, from which the cp gene of GLRaV-2 was identified. Based on the sequence information, two oligonucleotide primers have been designed. The sense primer CP-96F (SEQ. ID. No. 21) starts from the ATG initiation codon of the coat protein gene and the complementary primer CP-96R (SEQ. ID. No. 22) starts from 56 nucleotides downstream of the stop codon of the CP gene. A Nco I restriction site (11 bp in SEQ. ID. No. 21 and 13 bp in SEQ. ID. No. 22) is introduced in the beginning of both primers to facilitate the cloning. The coat protein gene of GLRaV-2 was amplified from dsRNA extracted from GLRaV-2 infected grapevine using reverse transcriptase polymerase chain reaction (RT-PCR). The PCR-amplified CP product was purified from low melting temperature agarose gel, digested with Nco I and cloned into the same enzyme digested plant expression vector pEPT8 (shown at FIG. 11). After screening, the orientation of recombinant construct was checked by using the internal restriction site of the CP gene and directly sequencing the CP gene. The recombinant construct with translatable (sense) full length coat protein gene, pEPT8CP-GLRaV2, was going through for the further cloning. The plant expression cassette, which consisted of a double cauliflower mosaic virus (CaMV) 35S-enhancer, a CaMV 35S-promoter, an alfalfa mosaic virus (ALMV) RNA4 5' leader sequence, a coat protein gene of GLRaV-2 (CP-GLRaV-2), and a CaMV 35S 3' untranslated region as a terminator, was cut using the EcoR I restriction enzyme, isolated from low melting point temperature agarose gel, and cloned into the same restriction enzyme treated binary vector pGA482GG or pGA482G (a derivative of pGA482 (An et al., "Binary Vectors," in *Plant Molecular Biology Manual*, pp. A3:1–19, Gelvin and Schilperoot, eds., Kinwer Academic Publishers, Dordrecht, Netherlands (1988), which is hereby incorporated by reference). The resulting recombinants constructs are pGA482GG/EPT8CP-GLRaV2 (shown at FIG. 11A), which contain both neomycin phosphotransferase (npt II) and β-glucuronidase (GUS) at the internal region of the T-DNA, and pGA482G/EPT8CP-GLRaV2 (shown at FIG. 11B) without GUS. These recombinants constructs were separately introduced by electroporation into disarmed avirulent *Agrobacterium tumefaciens* strain C58Z707. The *Agrobacterium tumefaciens* containing the vector was used to infect *Nicotiana benthamiana* wounded leaf disks according to the procedure essentially described by Horsch et al., "A Simple and General Method for Transferring Genes into Plants," Science 277:1229-1231 (1985), which is incorporated herein by reference.

Example 8
Analysis of Transgenic *Nicotiana benthamiana* Plants with the CP Gene of GLRaV-2

NPT II-ELISA: Double-antibody sandwich enzyme linked immnuosorbent assay (DAS-ELISA) was used to detect the npt II enzyme with an NPT II-ELISA kit (5' prime to 3' prime, Inc., Boulder, Co.).

Indirect ELISA: Polyclonal antibodies to GLRaV-2, which were prepared from the coat protein expressed in *E. coli*, were used. Plates were coated with homogenized samples in extraction buffer (1:10, w/v) (phosphate buffered saline containing 0.05% Tween 20 and 2% polyvinyl pyrrolidone) and incubated overnight at 4° C. After washing with phosphate buffered saline containing 0.05% Tween 20 (PBST), the plates were blocked with blocking buffer (phosphate buffered saline containing 2% BSA) and incubated at room temperature for 1 hr. The anti-GLRaV-2 IgG was added at 2 µg/ml after washing with PBST. After incubation at 30 C for 4 hr, the plates were washed with PBST, and the goat anti-rabbit IgG conjugate of alkaline phosphotase (Sigma) was added at 1:10,000 dilution. The absorbance was measured at 405 nm with a MicroELISA AutoReader. In addition, Western blot was also performed according to the method described by Hu et al., "Characterization of Closterovirus-like Particle Associated Grapevine Leafroll Disease," *J. Phytophathology* 128:1–14, (1990), which is incorporated herein by reference.

PCR analysis: Genomic DNA was extracted from leaves of putative transgenic and non-transgenic plants according to the method described by Cheung et al., "A Simple and Rapid DNA Microextraction Method for Plants, Animal, and Insect Suitable for RAPD and other PCR analysis," *PCR Methods and Applications* 3:69 (1996), which is incorporated herein by reference. The extracted total DNA served as the template for PCR reaction. The primers CP-96F and CP-96R (SEQ. ID. Nos. 21 and 22, respectively) for the CP gene of GLRaV-2, as well as npt II 5'- and 3'-primers were used for PCR analysis. PCR reaction was performed at the 94° C.×3 min for one cycle, followed by 30 cycles of 94° C.×1 min, 50° C.×1 min, and 72° C.×2:30 min with an additional extension at 72° C. for 10 min. The PCR product was analyzed on agarose gel.

After transformation, a total of 42 kanamycin resistant *Nicotiana benthamiana* lines ($R_0$) were obtained, of which the leaf samples were tested by NPT II enzyme activity. Among them, 37 lines were NPT II positive by ELISA, which took about 88.0% of total transformants. However, some of NPT II negative plants were obtained among these selected kanamycin resistant plants. All of the transgenic plants were self-pollinated in a greenhouse, and the seeds from these transgenic lines were germinated for further analysis.

The production of GLRaV-2 CP in transgenic plants was detected by indirect ELISA prior to inoculation, and the results showed that GLRaV-2 CP gene expression was not detectable in all transgenic plants tested. This result was further confirmed with Western blot. Using the antibody to GLRaV-2, the production of the CP was not detected in the transgenic and nontransgenic control plants. However, a protein of expected size (-22 kDa) was detected in GLRaV-2 infected positive control plants. This result was consistent with the ELISA result. The presence of the CP gene of GLRaV-2 in transgenic plants was detected from total genomic DNA extracted from plants tissue by PCR analysis (FIG. 12). The DNA product of expected size (653 bp) was amplified from twenty tested transgenic lines, but not in non-transgenic plants. The result indicated that the CP gene of GLRaV-2 was present at these transgenic lines, which was also confirmed by Northern blot analysis.

Example 9

$R_1$ and $R_2$ transgenic *Nicotiana benthamiana* Plants Are Resistant to GLRaV-2

Inoculation of transgenic plants: GLRaV-2 isolate 94/970, which was originally identified and transmitted from grapevine to *Nicotiana benthamiana* in South Africa (Goszczynski et al., "Detection of Two Strains of Grapevine Leafroll-Associated Virus 2," *Vitis* 35:133–35 (1996), which is incorporated herein by reference), was used as inoculum. The CP gene of isolate 94/970 was sequenced; and it is identical to the CP gene used in construction. *Nicotiana benthamiana* is an experimental host of GLRaV-2. The infection on it produces chlorotic and occasional necrotic lesions followed by systemic vein clearing. The vein clearing results in vein necrosis. Eventually the infected plants died, starting from the top to the bottom.

At five to seven leaf stage, two youngest apical leaves were challenged with GLRaV-2 isolate 94/970. Inoculum was prepared by grinding 1.0 g GLRaV-2 infected *Nicotiana benthamiana* leaf tissue in 5 ml of phosphate buffer (0.01M K2HPO4, PH7.0). The tested plants were dusted with carborundum and rubbed with the prepared inoculum. Non-transformed plants were simultaneously inoculated as above. The plants were observed for symptom development every other day for 60 days after inoculation. Resistant RI transgenic plants were carried on to R2 generation for further evaluation.

Transgenic progenies from 20 $R_0$ lines were initially screened for the resistance to GLRaV-2 followed by inoculation with GLRaV-2 isolate 94/970. The seedlings of the transgenic plants (NPT II positive), and nontransformed control plants were inoculated with GLRaV-2. After inoculation, the reaction of tested plants were divided into three types: highly susceptible (i.e. typical symptoms were observed two to four weeks postinoculation); tolerant (i.e. no symptom was developed in the early stage and typical symptoms was shown four to eight weeks postinoculation); and resistant (i.e. the plants remained asymptomatic eight weeks postinoculation). Based on the plant reaction, the resistant plants were obtained from fourteen different lines (listed in Table I below). In each of these fourteen lines, there was no virus detected within these plants by ELISA at 6 weeks postinoculation. In contrast, GLRaV-2 was detected in symptomatic plants by indirect ELISA. In the other six lines, although there were a few plants with some kind of delay in symptom development, all the inoculated transgenic plants died at three to eight weeks postinoculation. Based on the initial screening results, five representative lines consisting of three resistant lines (1, 4, and 19) and two susceptible lines (12 and 13) were selected for the further analysis.

TABLE 1

| | | Reaction of Tested Plants | | |
|---|---|---|---|---|
| No. Line | No. | HS | T | HR |
| line 1 | 39 | 14 | 3 | 22 |
| line 2 | 36 | 7 | 6 | 23 |
| line 3 | 38 | 11 | 4 | 23 |
| line 4 | 31 | 4 | 5 | 22 |
| line 5 | 33 | 6 | 13 | 14 |
| line 6 | 36 | 4 | 16 | 16 |
| line 7 | 32 | 5 | 9 | 18 |
| line 8 | 37 | 22 | 9 | 6 |
| line 9 | 36 | 9 | 12 | 15 |
| line 10 | 14 | 13 | 1 | 0 |
| line 11 | 13 | 11 | 2 | 0 |
| line 12 | 17 | 16 | 1 | 0 |
| line 13 | 16 | 14 | 0 | 0 |
| line 14 | 17 | 17 | 0 | 0 |
| line 15 | 32 | 30 | 2 | 0 |
| line 16 | 33 | 6 | 13 | 14 |
| line 17 | 12 | 0 | 1 | 11 |
| line 19 | 15 | 0 | 0 | 15 |
| line 20 | 19 | 3 | 0 | 16 |
| line 21 | 14 | 1 | 3 | 10 |
| control | 15 | 15 | 0 | 0 |

No Line: include transgenic lines and nontransformed control;
No: the number of transgenic and nontransformed plants;
HS: highly susceptible, typical symptoms were observed two to four weeks after inoculation;
T: tolerant, the symptoms were observed five to eight weeks after inoculation; and
HR: plants remain without asymptoms after eight weeks inoculation.

Table 2 below shows the symptom development in transgenic plants relative to non-transgenic control plants in the five selected lines in separate experiments. Non-transgenic control plants were all infected two to four weeks after inoculation, which showed typical GLRaV-2 symptoms on *Nicotiana benthamiana*, including chlorotic and local lesions followed by systemic vein clearing and vein necrosis on the leaves. Three of the tested lines (1, 4, and 19) showed some resistance that was manifested by either an absence or a delay in symptom development. Two other lines, 12 and 13, developed symptoms at nearly the same time as the non-transformed control plants. From top to bottom, the leaves of infected plants gradually became yellow, wilted, and dried, and, eventually, the whole plants died. No matter when infection occurred, the eventual result was the same. Six weeks after inoculation, all non-transgenic plants and the susceptible plants were dead. Some tolerant plants started to die. In contrast, the asymptomatic plants were flowering normally and pollinating as the non-inoculated healthy control plants (FIG. 13).

TABLE 2

| No. Line | No. | Reaction of Tested Plants | | |
|---|---|---|---|---|
| | | HS | T | HR |
| line 1 | 19 | 5 | 6 | 8 |
| line 4 | 15 | 9 | 1 | 5 |
| line 12 | 16 | 14 | 2 | 0 |
| line 13 | 18 | 13 | 5 | 0 |
| line 19 | 13 | 10 | 0 | 3 |
| non-transgenic | 24 | 23 | 1 | 0 |

No. Line: incude transgenic lines and nontransformed control;
No.: Number of transgenic and nontransformed plants tested;
HS: highly susceptible; typical symptoms were observed two to four weeks after inoculation;
T: tolerant, the symptoms were observed five to eight weeks postinoculation; and
HR: plants remain without asymptoms after eight weeks inoculation.

ELISA was performed at 6 weeks postinoculation to test the GLRaV-2 replication in the plants. Presumably, the increased level of CP reflected virus replication. The result showed that the absorbance value in symptomatic plants reached (OD) 0.7 to 3.2, compared to (OD) 0.10–0.13 prior to inoculation. In contrast, GLRaV-2 was not detected in asymptomatic plants, of which the absorbance value was the same or nearly the same as that of healthy nontransformed control plants. The data confirmed that virus replicated in symptomatic plants, but not in asymptomatic plants. The replication of GLRaV-2 was suppressed in asymptomatic plants. This result implicated that another mechanism other than the CP-mediated resistance was probably involved.

Three R2 progenies derived from transgenic resistant plants of lines 1, 4, and 19 were generated and utilized to examine the stable transmission and whether resistance was maintained in R2 generation. These results are shown in Table 3 below. NPT II analysis revealed that R2 progeny were still segregating. The CP expression in R2 progeny was still undetectable. After inoculation, all the nontransgenic plants were infected and showed GLRaV-2 symptoms on the leaves after 24 days postinoculation. In contrast, the inoculated transgenic $R_2$ progeny showed different levels of resistance from those highly susceptible to highly resistant. The tolerant and resistant plants were manifested by a delay in symptom development and absence of symptoms, respectively. At 6 weeks postinoculation, GLRaV-2 was detected in the tolerant symptomatic infected plants by indirect ELISA; but not in asymptomatic plants. This result indicated that virus replication was suppressed in these resistant plants, which was confirmed by Western blot. These resistant plants remained asymptomatic eight weeks postinoculation, and they were flowering normally and pollinating.

TABLE 3

| No. Line | No. Plants | NPT II positive/negative | Reaction of Tested Plants | | |
|---|---|---|---|---|---|
| | | | HS | T | HR |
| line 1/22 | 12 | 12/20 | 3 | 3 | 6 |
| line 1/30 | 11 | 8/3 | 7 | 2 | 2 |
| line 1/31 | 11 | 10/1 | 6 | 3 | 2 |
| line 1/35 | 10 | 10/0 | 4 | 6 | 0 |
| line 1/41 | 8 | 7/1 | 2 | 2 | 4 |
| line 4/139 | 12 | 11/1 | 4 | 4 | 3 |
| line 4/149 | 10 | 7/3 | 4 | 5 | 1 |
| line 4/152 | 10 | 8/2 | 9 | 0 | 1 |
| line 4/174 | 9 | 8/1 | 4 | 0 | 4 |

TABLE 3-continued

| No. Line | No. Plants | NPT II positive/negative | Reaction of Tested Plants | | |
|---|---|---|---|---|---|
| | | | HS | T | HR |
| line 19/650 | 11 | 10/1 | 7 | 0 | 2 |
| line 19/657 | 12 | 12/0 | 6 | 2 | 4 |
| line 19/660 | 10 | 8/2 | 3 | 6 | 1 |
| non-transformed CK | 12 | 0/12 | 12 | 0 | 0 |

HS: highly susceptible, typcial symptoms were observed two to four weeks after inoculation; T: tolerant, the symptoms were observed five to eight weeks postinoculation; and HR: plants remain asymptomatic at eight weeks postinoculation.

Example 10

Evidence for RNA-Mediated Protection in Transgenic Plants

Northern blot analysis: Total RNA was extracted from leaves prior to inoculation following the method described by Napoli et al., Plant Cell 2:279–89 (1990), which is hereby incorporatd by reference. The concentration of the extracted RNA was measured by spectrophotometer at OD 260. About 10 g of total RNA was used for each sample. The probe used was the 3' one third of GLRaV-2 CP gene, which was randomly labeled with $^{32}P(\alpha\text{-dATP})$ using Klenow fragment of DNA polymerase I.

Figure 14:
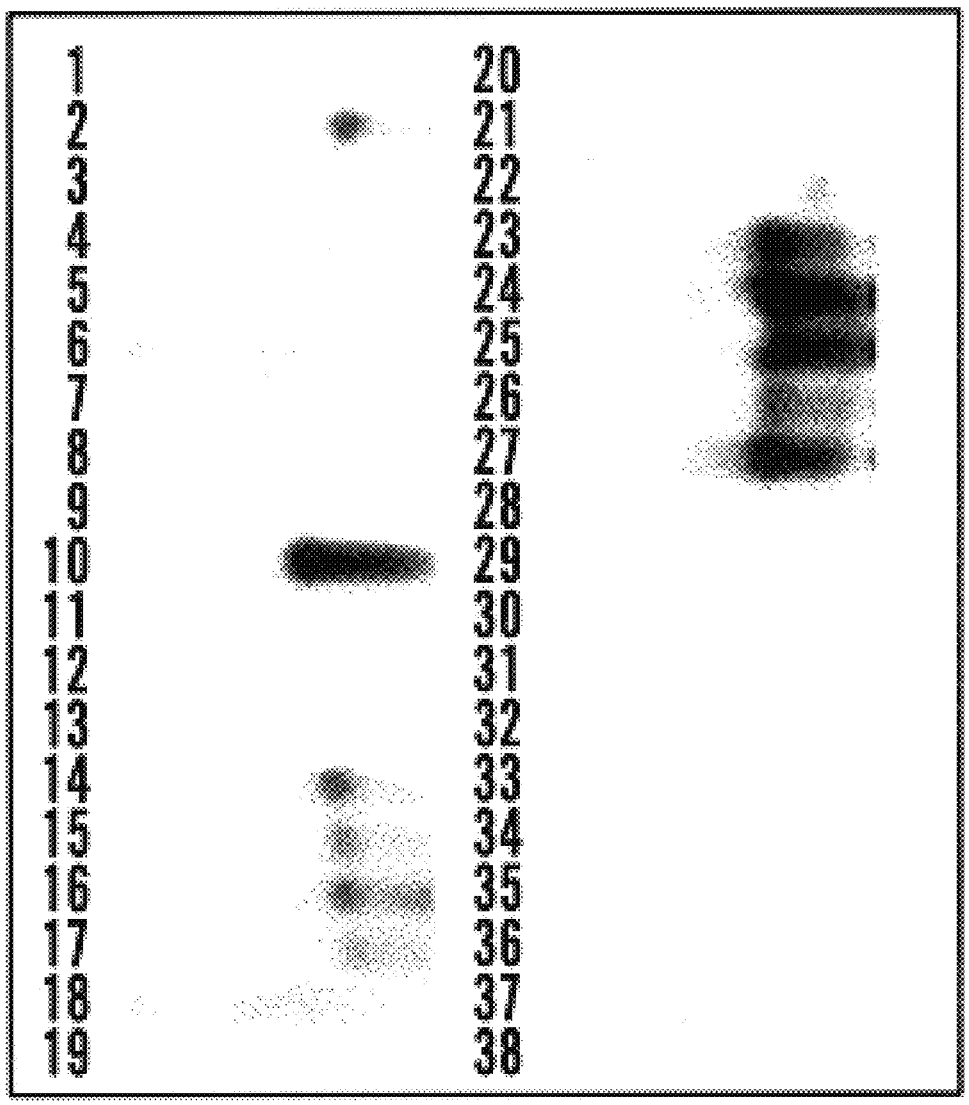
FIG. 14 is a northern blot analysis of transgenic Nicotiana benthamiana plants. An aliquot of 10 g of total RNA extracted from putative transgenic plants was denatured and loaded onto 1% agarose gel containing formaldehyde. The separated RNAs were transferred to Gene Screen Plus membrane and hybridized with a $^{32}$P-labeled DNA probe containing the 3' one third CP gene sequence. Lanes 1, 3, and 4 represent nontransformed control plants without RNA expression. The remaining lanes represent transgenic plants from different lines: lanes 2, 14–17, and 22–27 represent plants with high RNA expression level which are susceptible to GLRaV-2; all other lanes represent plants with undetectable or low RNA expression level which are resistant to GLRaV-2.

Using a DNA corresponding to the 3' one third CP gene sequence as probe, a single band was detected in the RNA extracted from susceptible plants from R1 progeny of lines 5, 12, and 13 by Northern hybridization. There was little or no signal detected in the transgenic plants from R1 progeny of line 1, 4, and 19. This RNA is not present in nontransformed control plants. The size of the hybridization signal was estimated to an approximately 0.9 kb nucleic acid, which was about the same as estimated (FIG. 14). In lines of 1, 4, and 19, the steady state level of RNA expression was also low in R2 progeny. This data showed that susceptible plants from lines 12 and 13 had high mRNA level and all transgenic plants from lines 1, 4, and 19 had low mRNA level.

Example 11

Transformation and Analysis of Transgenic Grapevines with the CP Gene of GLRaV-2

Plant materials: The rootstock cultivars Couderc 3309 (3309C) (V. riparia x V. rupestris), Vitis riparia 'Gloire de Montpellier' (Gloire), Teleki 5C (5C) (V. berlandieri x V. riparia), Millardet et De Grasset 101-14 (101-14 MGT) (V. riparia x V. rupestris), and Richter 110 (110R) (V. rupestris x V. berlandieri) were utilized. Initial embryogenic calli of Gloire were provided by Mozsar and Süle (Plant Protection Institute, Hungarian Academy of Science, Budapest). All other plant materials came from a vineyard at the New York State Agricultural Experiment Station, Geneva, N.Y. Buds were removed from the clusters and surface sterilized in 70% ethanol for 1–2 min. The buds (from the greenhouse and the field) were transferred to 1% sodium hypochlorite for 15 min, then rinsed three times in sterile, double-distilled water. Anthers were excised aseptically from flower buds with the aid of a stereo microscope. The pollen was crushed on a microscope slide under a coverslip with a drop of acetocarmine to observe the cytological stage. This was done to determine which stage was most favorable for callus induction.

Somatic embryogenesis and regeneration: Anthers were plated under aseptic conditions at a density of 40 to 50 per 9 cm diameter Petri dish containing MSE. Plates were cultured at 28° C. in the dark. Callus was initiated, and, after 60 days, embryos were induced and were transferred to hormone-free HMG medium for differentiation. Torpedo stage embryos were then transferred from HMG to MGC medium to promote embryo germination. Cultures were maintained in the dark at 26–28° C. and transferred to fresh medium at 3–4 week intervals. Elongated embryos were transferred to rooting medium in baby food jars (5–8 embryos per jar). The embryos were grown in a tissue culture room at 25° C. with a daily 16 h photoperiod (76 :mol. s) to induce shoot and root formation. After plants developed roots, they were transplanted to soil in the greenhouse.

Transformation: The protocols used for transformation were modified from those described by Scorza et.al., "Transformation of Grape (*Vitis vinifera* L.) Zygotic-derived Somatic Embryos and Regeneration of Transgenic Plants," *Plant Cell Rpt.* 14:589–92 (1995), which is hereby incorporated by reference. Overnight cultures of Agrobacterium strain C58Z707 or LBA4404 were grown in LB medium at 28° C. in a shaking incubator. Bacteria were centrifuged for 5 min at 3000–5000 rpm and resuspended in MS liquid medium (OD 1.0 at A600 nm). Calli with embryos were immersed in the bacterial suspension for 15–30 min, blotted dry, and transferred to HMG medium with or without acetosyringone (100 $\mu$M). Embryogenic calli were co-cultivated with the bacteria for 48 h in the dark at 28° C. Then, the plant material was washed in MS liquid plus cefotaxime (300 mg/ml) and carbenicillin (200 mg/ml) 2–3 times. To select transgenic embryos, the material was transferred to HMG medium containing either 20 or 40 mg/L kanamycin, 300 mg/L cefotaxime, and 200 mg/L carbenicillin. Alternatively, after co-cultivation, embryogenic calli were transferred to initiation MSE medium containing 25 mg/l kanamycin plus the same antibiotics listed above. All plant materials were incubated in continuous dark at 28° C. After growth on selection medium for 3 months, embryos were transferred to HMG or MGC without kanamycin to promote elongation of embryos. They were then transferred to rooting medium without antibiotics. Nontransformed calli were grown on the same media with and without kanamycin to verify the efficiency of the kanamycin selection process.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated RNA molecule encoding a protein or polypeptide of grapevine leafroll virus (type 2) wherein the protein or polypeptide is selected from a group consisting of a heat shock 70 protein and a coat protein.

2. An isolated DNA molecule encoding a protein or polypeptide of a grapevine leafroll virus (type 2) wherein the protein or polypeptide is a heat shock 70 protein having a molecular weight of from about 63 to about 67 kDa.

3. An isolated DNA molecule according to claim 2, wherein the protein or polypeptide comprises an amino acid sequence corresponding to SEQ. ID. No. 9.

4. An isolated DNA molecule according to claim 3, wherein the DNA molecule has a nucleotide sequence corresponding to SEQ. ID. No. 8.

5. An isolated DNA molecule encoding a coat protein from grapevine leafroll virus (type 2) having a molecular weight of from about 20 to about 24 kDa.

6. An isolated DNA molecule according to claim 5 wherein the coat protein comprises an amino acid sequence corresponding to SEQ. ID. No. 15.

7. An isolated DNA molecule encoding a protein or polypeptide of grapevine leafroll virus (type 2), wherein the DNA molecule has a nucleotide sequence corresponding to SEQ. ID. No. 14.

* * * * *